United States Patent
Senkovskyy et al.

(10) Patent No.: US 11,502,258 B2
(45) Date of Patent: Nov. 15, 2022

(54) ORGANIC ELECTRONIC DEVICE COMPRISING AN ORGANIC SEMICONDUCTOR LAYER

(71) Applicant: Novaled GmbH, Dresden (DE)

(72) Inventors: Volodymyr Senkovskyy, Dresden (DE); Regina Luschtinetz, Dresden (DE); Benjamin Schulze, Dresden (DE); Carsten Rothe, Dresden (DE)

(73) Assignee: Novaled GmbH, Dresden (DE)

( * ) Notice: Subject to any disclaimer, the term of this patent is extended or adjusted under 35 U.S.C. 154(b) by 408 days.

(21) Appl. No.: 16/615,211

(22) PCT Filed: May 18, 2018

(86) PCT No.: PCT/EP2018/063141
§ 371 (c)(1),
(2) Date: Nov. 20, 2019

(87) PCT Pub. No.: WO2018/215348
PCT Pub. Date: Nov. 29, 2018

(65) Prior Publication Data
US 2020/0161559 A1  May 21, 2020

(30) Foreign Application Priority Data
May 23, 2017 (EP) .................... 17172396

(51) Int. Cl.
*H01L 51/00* (2006.01)
*C07F 9/6521* (2006.01)
(Continued)

(52) U.S. Cl.
CPC ........ *H01L 51/0067* (2013.01); *C07F 9/6521* (2013.01); *C07F 9/65583* (2013.01);
(Continued)

(58) Field of Classification Search
None
See application file for complete search history.

(56) References Cited

U.S. PATENT DOCUMENTS

2014/0316134 A1  10/2014  Stoessel et al.
2015/0031896 A1   1/2015  Vestweber et al.
(Continued)

FOREIGN PATENT DOCUMENTS

| EP | 2750214 A2 | 7/2014 |
| JP | 2016-219487 A | 12/2016 |
| WO | WO-2018/208186 A1 * | 11/2018 |

OTHER PUBLICATIONS

Machine English translation of Vladimirovna et al. (WO-2018/208186-A1). Mar. 5, 2022.*
(Continued)

*Primary Examiner* — Jay Yang
(74) *Attorney, Agent, or Firm* — Eversheds Sutherland (US) LLP

(57) ABSTRACT

The present invention relates to a compound of formula 1 and an organic electronic device comprising an organic semiconductor layer, wherein at least one organic semiconductor layer comprises a compound of formula (1), wherein $L^1$ has the formula (2) and $L^2$ has the formula (3), wherein $L^1$ and $L^2$ are bonded at "*" via a single bond independently to the same or different arylene groups or heteroarylenes group of $Ar^1$; and wherein $X^1$, $X^2$ are independently selected from O, S and Se; $Ar^1$ is selected from substituted or unsubstituted $C_{20}$ to $C_{52}$ arylene or $C_{14}$ to $C_{64}$ heteroarylene, wherein the substituent of the substituted $C_{20}$ to $C_{52}$ arylene or $C_{14}$ to $C_{64}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl; $R^1$, $R^2$ are independently selected from substituted or unsubstituted $C_1$ to $C_{16}$ alkyl, wherein the substituent of substituted $C_1$ to $C_{16}$ alkyl is (Continued)

selected from $C_6$ to $C_{18}$ arylene or $C_2$ to $C_{12}$ heteroarylene; $R^3$, $R^4$ are independently selected from substituted or unsubstituted $C_1$ to $C_{16}$ alkyl, substituted or unsubstituted $C_6$ to $C_{18}$ arylene, $C_2$ to $C_{20}$ heteroarylene, wherein the substituent of substituted $C_1$ to $C_{16}$ alkyl, the substituent of the substituted $C_6$ to $C_{18}$ arylene, $C_2$ to $C_{20}$ heteroarylene are independently selected from $C_6$ to $C_{18}$ arylene or $C_2$ to $C_{12}$ heteroarylene; n is selected from 1 to 5, wherein n is an integer number.

25 Claims, 3 Drawing Sheets

(51) Int. Cl.
  *C07F 9/6558* (2006.01)
  *H01L 51/50* (2006.01)
(52) U.S. Cl.
  CPC ...... *C07F 9/65586* (2013.01); *H01L 51/0072* (2013.01); *H01L 51/0073* (2013.01); *H01L 51/0074* (2013.01); *H01L 51/5072* (2013.01); *H01L 51/5092* (2013.01)

(56) References Cited

U.S. PATENT DOCUMENTS

2016/0163992 A1    6/2016    Bae et al.
2018/0076395 A1    3/2018    Han et al.

OTHER PUBLICATIONS

Abstractor Dova et al. (Asian J. Org. Chem. 2016, 5(4), 537-549).*
STN search result of Dova et al. (Asian J. Org. Chem. 2016, 5(4), 537-549).*
PCT International Search Report and Written Opinion for PCT Application No. PCT/EP2018/063141 dated Aug. 29, 2018 (13 pages).
Plourde et al., "Syntheses and Characterization of Upper Rim 1,2- and 1,3-Diphosphinated Calix[4]arenes and Their Corresponding 1,5-Cyclooctadienylrhodium(I) Complexes: Comparison of the Catalytic Hydroformylation Properties of Terminal Alkenes," Organometallics, Ameircan Chemical Society, 2003, 22(14):2862-2875.
Yang et al., "Cu-Catalyzed Direct C6-Arylation of Indoles." J Am Chem Soc.. 2016, 138(28):8734-8737.

* cited by examiner

ORGANIC ELECTRONIC DEVICE COMPRISING AN ORGANIC SEMICONDUCTOR LAYER

CROSS REFERENCE TO RELATED APPLICATIONS

This application is a U.S. national stage application of PCT/EP2018/063141, filed May 18, 2018, which claims priority to European Application No. 17172396.8, filed May 23, 2017. The content of these applications is incorporated herein by reference.

TECHNICAL FIELD

The present invention relates to an organic electronic device comprising an organic semiconductor layer, an organic semiconductor layer, an organic semiconductor layer material and a method of manufacturing the same.

BACKGROUND ART

Organic electronic devices, such as organic light-emitting diodes OLEDs, which are self-emitting devices, have a wide viewing angle, excellent contrast, quick response, high brightness, excellent operating voltage characteristics, and color reproduction. A typical OLED comprises an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency and/or a long lifetime.

Performance of an organic light emitting diode may be affected by characteristics of the organic semiconductor layer, and among them, may be affected by characteristics of an organic material of the organic semiconductor layer.

Particularly, development for an organic material being capable of increasing electron mobility and simultaneously increasing electrochemical stability is needed so that the organic electronic device, such as an organic light emitting diode, may be applied to a large-size flat panel display.

JP2016219487 discloses an organic electroluminescent element comprises: a pair of an anode and a cathode; and organic layers sandwiched between the paired anode and cathode. The organic layers have a luminescent layer; at least one of the organic layers includes a compound having a structure expressed by the general formula (1) below (1)

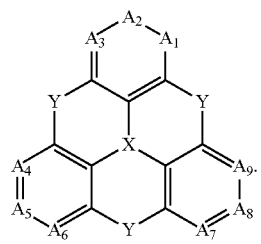

EP2750214 discloses an organic light emitting device comprising a first electrode, a second electrode, and one or more organic material layers disposed between the first electrode and the second electrode, and having an excellent life-span property by changing a dipole moment of a compound comprised in the organic material layers.

There remains a need to improve performance of organic semiconductor layers, organic semiconductor materials, as well as organic electronic devices thereof, in particular to achieve higher efficiency and/or longer lifetime through improving the characteristics of the compounds comprised therein.

In particular there is a need for organic semiconductor materials and organic semiconductor layer as well as organic electronic devices with improved conductivity and thereby reduced operating voltage.

There is a need for a reduced operating voltage and thereby reduced power consumption and increased battery life of for example mobile electronic devices, as well as for increased efficiency in such devices.

DISCLOSURE

An aspect of the present invention provides an organic electronic device comprising an organic semiconductor layer, wherein at least one organic semiconductor layer comprises a compound of formula 1:

$$L^1\text{-}Ar^1\text{-}[\text{-}L^2]_n \qquad (1),$$

wherein
$L^1$ has the formula 2:

(2)

and
$L^2$ has the formula 3:

(3)

wherein
$L^1$ and $L^2$ are bonded at "*" via a single bond independently to the same or different arylene groups or heteroarylene groups of $Ar^1$; and wherein
$X^1$, $X^2$ are independently selected from O, S and Se;
$Ar^1$ is selected from substituted or unsubstituted $C_{20}$ to $C_{52}$ arylene or $C_{14}$ to $C_{64}$ heteroarylene, wherein the substituent of the substituted $C_{20}$ to $C_{52}$ arylene or $C_{14}$ to $C_{64}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl;
$R^1$, $R^2$ are independently selected from substituted or unsubstituted $C_1$ to $C_{16}$ alkyl, wherein the substituent of substituted $C_1$ to $C_{16}$ alkyl is selected from $C_6$ to $C_{18}$ arylene or $C_2$ to $C_{12}$ heteroarylene;

$R^3$, $R^4$ are independently selected from substituted or unsubstituted $C_1$ to $C_{16}$ alkyl, substituted or unsubstituted $C_6$ to $C_{18}$ arylene, $C_2$ to $C_{20}$ heteroarylene,
wherein the substituent of substituted $C_1$ to $C_{16}$ alkyl, the substituent of the substituted $C_6$ to $C_{18}$ arylene, $C_2$ to $C_{20}$ heteroarylene are independently selected from $C_6$ to $C_{18}$ arylene or $C_2$ to $C_{12}$ heteroarylene;

n is selected from 1 to 5, wherein n is an integer number.

According to an embodiment the organic electronic device may comprise an organic semiconductor layer, wherein at least one organic semiconductor layer comprises a compound of formula 1:

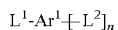 (1), wherein $L^1$ has the formula 2:

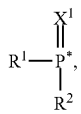 (2)

and $L^2$ has the formula 3:

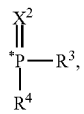 (3)

wherein $L^1$ and $L^2$ are bonded at "*" via a single bond independently to the same or different arylene groups or heteroarylene groups of $Ar^1$; and wherein $X^1$, $X^2$ are independently selected from O, S and Se;

$Ar^1$ is selected from substituted or unsubstituted $C_{20}$ to $C_{52}$ arylene or $C_{14}$ to $C_{64}$ heteroarylene, wherein the substituent of the substituted $C_{20}$ to $C_{52}$ arylene or $C_{14}$ to $C_{64}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl;

$R^1$, $R^2$ are independently selected from substituted or unsubstituted $C_1$ to $C_{16}$ alkyl, wherein the substituent of substituted $C_1$ to $C_{16}$ alkyl is selected from $C_6$ to $C_{18}$ arylene or $C_2$ to $C_{12}$ heteroarylene;

$R^3$, $R^4$ are independently selected from substituted or unsubstituted $C_1$ to $C_{16}$ alkyl, substituted or unsubstituted $C_6$ to $C_{18}$ arylene, $C_2$ to $C_{20}$ heteroarylene,
wherein the substituent of substituted $C_1$ to $C_{16}$ alkyl, the substituent of the substituted $C_6$ to $C_{18}$ arylene, $C_2$ to $C_{20}$ heteroarylene are independently selected from $C_6$ to $C_{18}$ arylene or $C_2$ to $C_{12}$ heteroarylene;

n is selected from 1 to 5, wherein n is an integer number;

wherein for formula 1 or $Ar^1$ the following structure unit is excluded:

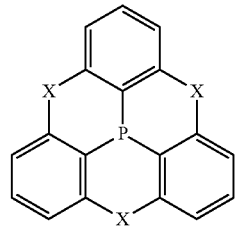

X with X=O, S or Se.

According to one embodiment of formula 1, wherein $L^1$ and $L^2$ are bonded at "*" via a single bond to the same arylene group or different arylene groups of $Ar^1$, preferably $L^1$ and $L^2$ are bonded at "*" via a single bond to the same arylene group.

According to one embodiment of formula 1, wherein $L^1$ and $L^2$ are bonded at "*" via a single bond to the same heteroarylene group or different heteroarylene groups of $Ar^1$, preferably $L^1$ and $L^2$ are bonded at "*" via a single bond to the same heteroarylene group.

According to another embodiment the compound of formula 1 is represented by formula 4:

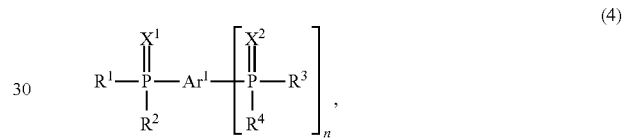 (4)

wherein $X^1$, $X^2$ are independently selected from O, S and Se;

$Ar^1$ is selected from substituted or unsubstituted $C_{20}$ to $C_{52}$ arylene or $C_{14}$ to $C_{64}$ heteroarylene, wherein the substituent of the substituted $C_{20}$ to $C_{52}$ arylene or $C_{14}$ to $C_{64}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl;

$R^1$, $R^2$ are independently selected from substituted or unsubstituted $C_1$ to $C_{16}$ alkyl,
wherein the substituent of substituted $C_1$ to $C_{16}$ alkyl is selected from $C_6$ to $C_{18}$ arylene or $C_2$ to $C_{12}$ heteroarylene;

$R^3$, $R^4$ are independently selected from substituted or unsubstituted $C_6$ to $C_{18}$ arylene, $C_2$ to $C_{20}$ heteroarylene and $C_1$ to $C_{16}$ alkyl,
wherein the substituent of the substituted $C_6$ to $C_{18}$ arylene, $C_2$ to $C_{20}$ heteroarylene and $C_1$ to $C_{16}$ alkyl is selected from $C_6$ to $C_{18}$ arylene or $C_2$ to $C_{12}$ heteroarylene;

n is selected from 1 to 5, wherein n is an integer number;

wherein the compound of formula 4 comprises at least about 4 of $C_6$ arylene rings, preferably at least about 5 of $C_6$ arylene rings to about 12 of $C_6$ arylene rings and further preferred about 5 of $C_6$ arylene rings to about 10 of $C_6$ arylene rings.

According to another embodiment of the compound of formula 1 or 4, wherein n is selected from about 1 to about 3 or preferably about 1 to about 2, wherein n is an integer number.

The compound represented by formula 1 or 4, and an organic semiconductor layer as well as organic electronic device comprising the compound of formula 1 have strong electron transport characteristics to increase charge mobility and/or stability and thereby to improve luminance efficiency, voltage characteristics, and/or life-span characteristics.

The compound represented by formula 1 and 4, and an organic semiconductor layer as well as organic electronic device comprising the compound of formula 1 and 4 have high electron mobility and a low operating voltage.

Without being bounded to a specific theory, it is assumed that the low operating voltage can be achieved for arylene and heteroarylene compounds with at least one dialkyl PO group bonded thereto. This may be due to the reduced steric hindrance of dialkyl compared to diphenyl PO groups. Thereby, a higher density of electron transporting arylene and heteroarylene groups may be achieved.

The organic semiconductor layer comprising a compound for formula 1 or 4 may be used as an electron transport layer as well as an emission layer.

According to another embodiment, the organic semiconductor layer may further comprise an emitter compound.

According to another embodiment, the organic semiconductor layer may consist of compound of formula 1 or 4.

The organic semiconductor layer may be non-emissive.

In the context of the present specification the term "essentially non-emissive" or "non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconductor layer comprising the compound of formula 1 or 4 is essentially non-emissive or non-emissive.

In the context of the present specification the term "organic electronic device" means a device that comprises an organic semiconductor layer.

The "emission layer" may also be named "emissive layer" or "light-emitting layer".

According to another embodiment, the organic semiconductor layer comprising the compound of formula 1 or 4 is free of group III to VI, rare earth and transition metal compounds.

The term "free of", "does not contain", "does not comprise" does not exclude impurities which may be present in the compounds prior to deposition. Impurities have no technical effect with respect to the object achieved by the present invention.

The operating voltage, also named U, is measured in Volt (V) at 10 milliAmpere per square centimeter (mA/cm2).

The candela per Ampere efficiency, also named cd/A efficiency, is measured in candela per ampere at 10 milliAmpere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "transition metal" means and comprises any element in the d-block of the periodic table, which comprises groups 3 to 12 elements on the periodic table.

The term "group III to VI metal" means and comprises any metal in groups III to VI of the periodic table.

The term "life-span" and "lifetime" are simultaneously used and have the same meaning.

As used herein, "weight percent", "wt.-%", "percent by weight", "% by weight", and variations thereof refer to a composition, component, substance or agent as the weight of that composition, component, substance or agent of the respective electron transport layer divided by the total weight of the composition thereof and multiplied by 100. It is understood that the total weight percent amount of all components, substances or agents of the respective electron transport layer are selected such that it does not exceed 100 wt.-%.

As used herein, "volume percent", "vol.-%", "percent by volume", "% by volume", and variations thereof refer to an elemental metal, a composition, component, substance or agent as the volume of that elemental metal, component, substance or agent of the respective electron transport layer divided by the total volume of the respective electron transport layer thereof and multiplied by 100. It is understood that the total volume percent amount of all elemental metal, components, substances or agents of the respective cathode electrode layer are selected such that it does not exceed 100 vol.-%.

All numeric values are herein assumed to be modified by the term "about", whether or not explicitly indicated. As used herein, the term "about" refers to variation in the numerical quantity that can occur. Whether or not, modified by the term "about", the claims include equivalents to the quantities.

It should be noted that, as used in this specification and the appended claims, the singular forms "a", "an", and "the" include plural referents unless the content clearly dictates otherwise.

The anode electrode and cathode electrode may be described as anode electrode/cathode electrode or anode electrode/cathode electrode or anode electrode layer/cathode electrode layer.

According to another aspect, an organic optoelectronic device comprises an anode layer and a cathode layer facing each other and at least one organic semiconductor layer between the anode layer and the cathode layer, wherein the organic semiconductor layer comprises the compound of formula 1 or 4.

According to yet another aspect, a display device comprising the organic optoelectronic device is provided.

In the present specification, when a definition is not otherwise provided, an "alkyl group" may refer to an aliphatic hydrocarbon group. The alkyl group may refer to "a saturated alkyl group" without any double bond or triple bond.

The alkyl group may be a $C_1$ to $C_{12}$ alkyl group. More specifically, the alkyl group may be a $C_1$ to $C_{10}$ alkyl group or a $C_1$ to $C_6$ alkyl group. For example, a $C_1$ to $C_4$ alkyl group comprises 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification "arylene group" may refer to a group comprising at least one hydrocarbon aromatic moiety, and all the elements of the hydrocarbon aromatic moiety may have p-orbitals which form conjugation, for example a phenyl group, a naphthyl group, an anthracenyl group, a phenanthrenyl group, a pyrenyl group, a fluorenyl group and the like.

The arylene group may include a monocyclic, polycyclic or fused ring polycyclic (i.e., rings sharing adjacent pairs of carbon atoms) functional group.

The term "heteroarylene" refers to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S. The term "heteroarylene" as used herewith shall encompass pyridine, quinoline, quinazoline, pyridine, triazine, benzimidazole, benzothiazole, benzo[4,5]thieno[3,2-d]pyrimidine, carbazole, xanthene, phenoxazine, benzoacridine, dibenzoacridine and the like.

In the present specification, the single bond refers to a direct bond.

According to another embodiment of formula 1, wherein the compound of formula 1 or 4 is free of heteroarylene groups or comprises at least about 1 to about 3 heteroarylene groups.

According to one embodiment of formula 1 or 4, wherein the compound of formula 1 or 4 comprises at least about 4 of $C_6$ arylene rings, preferably at least about 5 of $C_6$ arylene rings to about 12 of $C_6$ arylene rings or at least about 6 of $C_6$ arylene rings to about 11 of $C_6$ arylene rings and further preferred about 7 of $C_6$ arylene rings to about 10 of $C_6$ arylene rings.

The term "$C_6$-arylene ring" means single $C_6$-arylene rings and $C_6$-arylene rings which form condensed ring systems. For example, a naphthylene group would be counted as two $C_6$-arylene rings.

According to another embodiment of formula 1 or 4, wherein at least one heteroarylene group is selected from triazine, quinazoline, benzimidazole, benzothiazole, benzo[4,5]thieno[3,2-d]pyrimidine, pyrimidine and pyridine and is preferably selected from triazine and pyrimidine.

According to another embodiment of formula 1 or 4: $R^1$, $R^2$ may be independently selected from substituted or unsubstituted $C_1$ to $C_{14}$ alkyl, wherein the substituent of substituted or unsubstituted $C_1$ to $C_{14}$ alkyl is selected from $C_6$ to $C_{14}$ arylene or $C_2$ to $C_{10}$ heteroarylene.

According to another embodiment of formula 1 or 4: $R^3$, $R^4$ may be independently selected from substituted or unsubstituted $C_6$ to $C_{16}$ arylene, $C_2$ to $C_{18}$ heteroarylene and $C_1$ to $C_{14}$ alkyl, wherein the substituent of the substituted $C_6$ to $C_{16}$ arylene, $C_2$ to $C_{18}$ heteroarylene and $C_1$ to $C_{14}$ alkyl is selected from $C_6$ to $C_{14}$ arylene or $C_2$ to $C_{10}$ heteroarylene.

According to another embodiment of formula 1 or 4: $Ar^1$ are independently selected from substituted or unsubstituted $C_{22}$ to $C_{48}$ arylene or $C_{15}$ to $C_{60}$ heteroarylene, wherein the substituent of the substituted $C_{22}$ to $C_{48}$ arylene or $C_{15}$ to $C_{60}$ heteroarylene is selected from $C_1$ to $C_{10}$ alkyl, $C_1$ to $C_{10}$ alkoxy, CN, halogen, OH, $C_6$ to $C_{20}$ aryl and $C_2$ to $C_{17}$ heteroaryl.

According to another embodiment of formula 1 or 4: $R^1$, $R^2$ may be independently selected from substituted or unsubstituted $C_2$ to $C_{10}$ alkyl, wherein the substituent of substituted or unsubstituted $C_2$ to $C_{10}$ alkyl is selected from $C_6$ to $C_{12}$ arylene or $C_6$ to $C_{12}$ heteroarylene.

According to another embodiment of formula 1 or 4: $R^3$, $R^4$ may be independently selected from substituted or unsubstituted $C_6$ to $C_{12}$ arylene, $C_6$ to $C_{12}$ heteroarylene and $C_2$ to $C_{10}$ alkyl, wherein the substituent of the substituted $C_6$ to $C_{12}$ arylene, $C_6$ to $C_{12}$ heteroarylene and $C_2$ to $C_{10}$ alkyl is selected from $C_6$ to $C_{12}$ arylene or $C_6$ to $C_{12}$ heteroarylene.

According to another embodiment of the compound of formula 1 or 4, wherein
$R^1$, $R^2$ are selected from $C_1$ to $C_{16}$ alkyl, preferably $C_1$ to $C_6$ alkyl: and
$R^3$, $R^4$ are selected from $C_6$ to $C_{18}$ aryl, preferably $C_6$ to $C_{12}$ aryl.

According to another embodiment of formula 1 or 4: $Ar^1$ are independently selected from substituted or unsubstituted $C_{24}$ to $C_{42}$ arylene or $C_{16}$ to $C_{54}$ heteroarylene, wherein the substituent of the substituted $C_{24}$ to $C_{42}$ arylene or $C_{16}$ to $C_{54}$ heteroarylene is selected from $C_2$ to $C_8$ alkyl, $C_2$ to $C_8$ alkoxy, CN, halogen, OH, $C_6$ to $C_{20}$ aryl and $C_6$ to $C_{17}$ heteroaryl.

According to another embodiment of formula 1 or 4: n is selected from about 1 to about 3, or preferably about 1 to about 2, wherein n is an integer number.

According to another embodiment of formula 1 or 4: $X^1$ and $X^2$ are preferably selected the same, preferably $X^1$ and $X^2$ are O.

According to another embodiment of formula 1 or 4: $R^1$, $R^2$, $R^3$ and $R^4$ are independently selected from $C_1$ to $C_{16}$ alkyl, preferably $C_1$ to $C_6$ alkyl, further preferred $C_1$ to $C_2$ alkyl, more preferred $R^1$, $R^2$, $R^3$ and $R^4$ are selected the same and further more preferred $R^1$, $R^2$, $R^3$ and $R^4$ are $C_1$ alkyl.

According to another embodiment of formula 1 or 4:
$R^1$, $R^2$ are selected from $C_1$ to $C_{16}$ alkyl, preferably $C_1$ to $C_6$ alkyl: and
$R^3$, $R^4$ are selected from $C_6$ to $C_{18}$ aryl, preferably $C_6$ to $C_{12}$ aryl.

According to another embodiment of formula 1 or 4:
$R^1$, $R^2$ are selected from $C_1$ alkyl and
$R^3$, $R^4$ are selected from $C_6$ aryl.

According to another embodiment of formula 1 or 4:
wherein
$X^1$, $X^2$ are O;
$Ar^1$ is selected from unsubstituted $C_{20}$ to $C_{52}$ arylene or unsubstituted $C_{14}$ to $C_{64}$ heteroarylene, preferably unsubstituted $C_{22}$ to $C_{48}$ arylene;
$R^1$, $R^2$ are independently selected from unsubstituted $C_1$ to $C_6$ alkyl, preferably $C_1$ or $C_2$ alkyl;
$R^3$, $R^4$ are independently selected from unsubstituted $C_1$ to $C_6$ alkyl, preferably $C_1$ or $C_2$ alkyl;
n is selected from about 1 to about 3, preferably about 2 to about 3, wherein n is an integer number.

According to another embodiment of formula 1 or 4:
wherein
$X^1$, $X^2$ are O;
$Ar^1$ is selected from unsubstituted $C_{22}$ to $C_{48}$ arylene or unsubstituted $C_{15}$ to $C_{58}$ heteroarylene, preferably unsubstituted $C_{24}$ to $C_{46}$ arylene or unsubstituted $C_{15}$ to $C_{54}$ heteroarylene;
$R^1$, $R^2$ are independently selected from unsubstituted $C_1$ to $C_6$ alkyl, preferably $C_1$ or $C_2$ alkyl;
$R^3$, $R^4$ are independently selected from unsubstituted $C_1$ to $C_6$ alkyl, preferably $C_1$ or $C_2$ alkyl;
n is selected from about 1 to about 3, preferably about 2 to about 3, wherein n is an integer number.

According to another embodiment, wherein the compound of formula 1 has a dipole moment of about ≥0 and about ≤3 Debye, preferably about ≥0 and about ≤2 Debye.

Preferably, the dipole moment of the compound of formula 1 may be selected ≥0 and ≤1 Debye, further preferred ≥0 and ≤0.8 Debye, also preferred ≥0 and ≤0.4 Debye.

Surprisingly, it has been found that particularly high conductivity and low operating voltage of an organic semiconductor layer comprising compounds of formula 1 or 4 may be obtained when the dipole moment of compound for formula 1 or 4 is selected in this range.

The dipole moment $|\vec{\mu}|$ of a molecule containing N atoms is given by:

$$\vec{\mu} = \sum_i^N q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method.

The partial charges and atomic positions in the gas phase are obtained using the hybrid functional B3LYP with a 6-31G* basis set as implemented in the program package TURBOMOLE V6.5 (TURBOMOLE GmbH, Litzenhardtstrasse 19, 76135 Karlsruhe, Germany). If more than one conformation is viable, the conformation with the lowest total energy is selected to determine the dipole moment.

According to another embodiment, the reduction potential of the compound of formula 1 or 4 may be selected more negative than −1.9 V and less negative than −2.6 V against Fc/Fc$^+$ in tetrahydrofuran, preferably more negative than −2 V and less negative than −2.5 V.

The reduction potential may be determined by cyclic voltammetry with potentiostatic device Metrohm PGSTAT30 and software Metrohm Autolab GPES at room temperature. The redox potentials are measured in an argon de-aerated, anhydrous 0.1M THF solution of the compound of formula 1 or 4, under argon atmosphere, with 0.1M tetrabutylammonium hexafluorophosphate as supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run is done in the broadest range of the potential set on the working electrodes, and the range is then adjusted within subsequent runs appropriately. The final three runs are done with the addition of ferrocene (in 0.1M concentration) as the standard. The average of potentials corresponding to cathodic and anodic peak of the compound is determined through subtraction of the average of cathodic and anodic potentials observed for the standard Fc$^+$/Fc redox couple.

Particularly good electron injection and/or electron transport into the emission layer and/or stability may be achieved if the reduction potential is selected in this range.

According to another embodiment the compound of formula 1 or 4 has a glass transition temperature Tg of about ≥120° C. and about ≤380° C., preferably about ≥130° C. and about ≤350° C., further preferred about ≥150° C. and about ≤320° C.

The glass transition temperature is measured under nitrogen and using a heating rate of 10 K per min in a Mettler Toledo DSC 822e differential scanning calorimeter as described in DIN EN ISO 11357, published in March 2010.

According to another embodiment the compound of formula 1 or 4 has a rate onset temperature $T_{RO}$ of about ≥150° C. and ≤400° C., preferably about ≥180° C. and about ≤380° C.

Weight loss curves in TGA (thermogravimetric analysis) are measured by means of a Mettler Toledo TGA-DSC 1 system, heating of samples from room temperature to 600° C. with heating rate 10 K/min under a stream of pure nitrogen. 9 to 11 mg sample are placed in a 100 μL Mettler Toledo aluminum pan without lid. The temperature is determined at which 0.5 wt.-% weight loss occurs.

Room temperature, also named ambient temperature, is 23° C.

The rate onset temperature for transfer into the gas phase is determined by loading 100 mg compound into a VTE source. As VTE source a point source for organic materials is used as supplied by Kurt J. Lesker Company (www.lesker.com) or CreaPhys GmbH (http://www.creaphys.com). The VTE (vacuum thermal evaporation) source temperature is determined through a thermocouple in direct contact with the compound in the VTE source. The VTE source is heated at a constant rate of 15 K/min at a pressure of 10$^{-7}$ to 10$^{-8}$ mbar in the vacuum chamber and the temperature inside the source measured with a thermocouple. Evaporation of the compound is detected with a QCM detector which detects deposition of the compound on the quartz crystal of the detector. The deposition rate on the quartz crystal is measured in Ångstrom per second. To determine the rate onset temperature, the deposition rate on a logarithmic scale is plotted against the VTE source temperature. The rate onset is the temperature at which noticeable deposition on the QCM detector occurs (defined as a rate of 0.02Å/s. The VTE source is heated and cooled three time and only results from the second and third run are used to determine the rate onset temperature.

The rate onset temperature is an indirect measure of the volatility of a compound. The higher the rate onset temperature the lower is the volatility of a compound.

According to another embodiment of the compound of formula 1 or 4, wherein Ar$^1$ has the formula 5:

(5)

wherein

L$^3$ and L$^4$ are bonded at "*" via a single bond to L$^1$ and L$^2$,

Ar$^2$ is selected from C$_{10}$ to C$_{42}$ arylene or C$_2$ to C$_{54}$ heteroarylene, preferably C$_{18}$ to C$_{24}$ arylene or C$_3$ to C$_{12}$ heteroarylene, L$^3$, L$^4$ are independently selected from phenylene, biphenylene, fluoren-di-yl or a direct bond, m is selected from 1 to 5, wherein m is an integer number.

Preferably, m is selected from 1, 2, 3 or 5, even more preferred from 1, 2, or 3.

Preferably, L$^3$ and L$^4$ are selected the same.

According to another embodiment, Ar$^2$ is selected from naphthalene, anthracene, tetraphene, tetracene, phenanthrene, pyrene, chrysene, perylene, fluorene, benzofluorene, dibenzofluorene, triphenylene, coronene and hexabenzo[bc,ef,hi,kl,no,qr]coronene, pyridine, quinoline, quinozaline, pyrimidine, triazine, benzimidazole, benzothiazole, benzo[4,5]thieno[3,2-d]pyrimidine, carbazole, xanthene, phenoxazine, benzoacridine, dibenzoacridine, triazole.

According to another embodiment, Ar$^2$ is selected from condensed arylene groups, preferably naphthalene, anthracene, tetraphene, tetracene, phenanthrene, pyrene, chrysene, perylene, fluorene, benzofluorene, dibenzofluorene, triphenylene, coronene and hexabenzo[bc,ef,hi,kl,no,qr]coronene.

According to another embodiment, Ar² is selected from heteroarylene groups, preferably heteroarylene groups comprising at least one nitrogen or oxygen atom, preferably pyridine, quinoline, quinozaline, pyrimidine, triazine, benzimidazole, benzothiazole, benzo[4,5]thieno[3,2-d]pyrimidine, carbazole, xanthene, phenoxazine, benzoacridine, dibenzoacridine, triazole.

According to another embodiment, wherein Ar² is selected from the group consisting of D1 to D23:

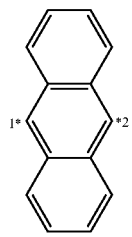
(D1)

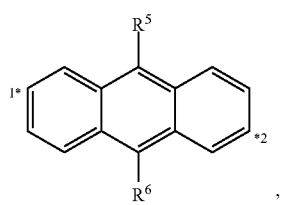
(D2)

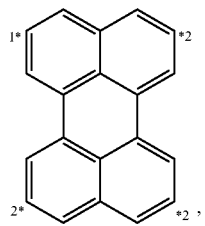
(D3)

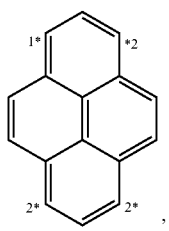
(D4)

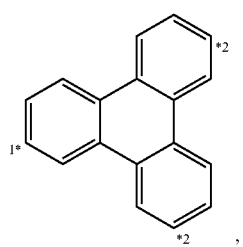
(D5)

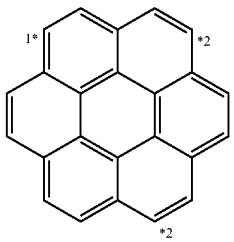
(D6)

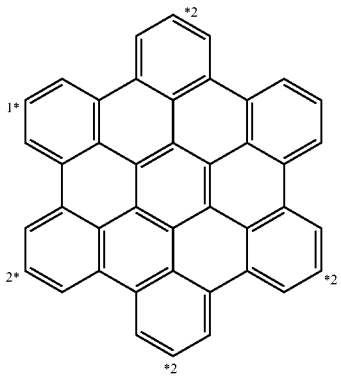
(D7)

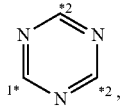
(D8)

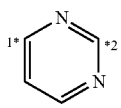
(D9)

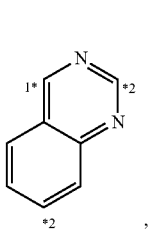
(D10)

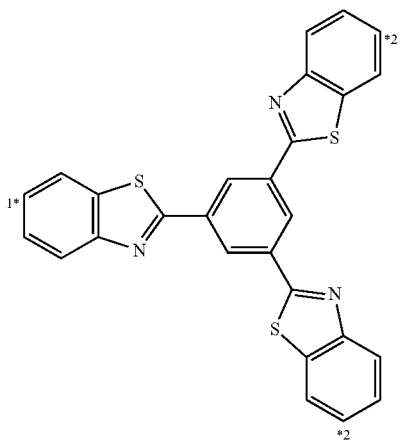
(D11)

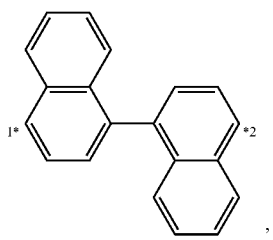 (D12)

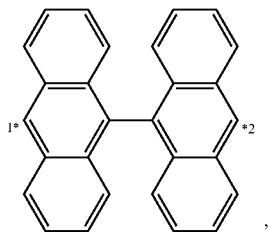 (D13)

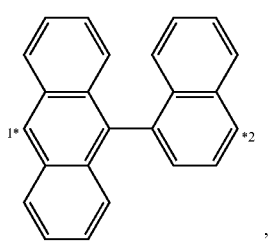 (D14)

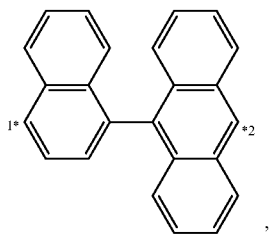 (D15)

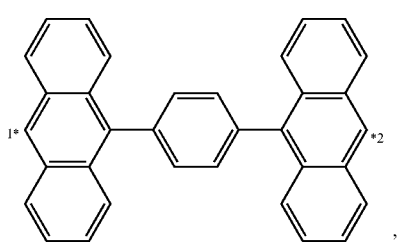 (D16)

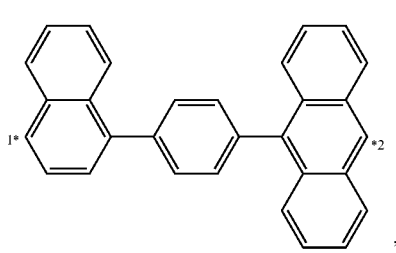 (D17)

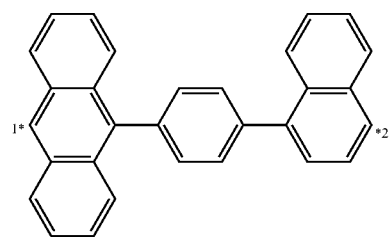 (D18)

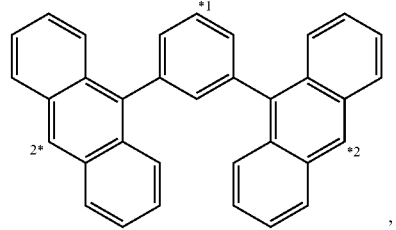 (D19)

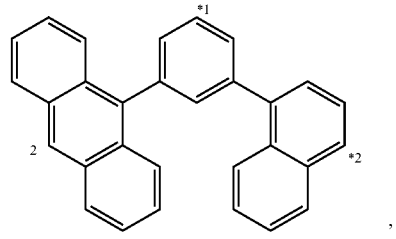 (D20)

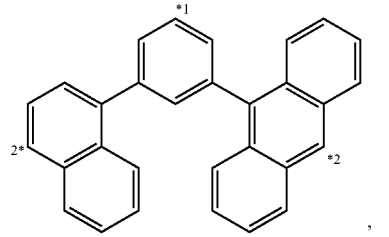 (D21)

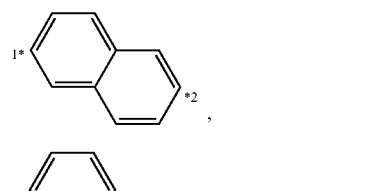 (D22)

(D23)

wherein $Ar^2$ is bonded to $L^3$ via "*1" and $Ar^2$ is bonded to $L^4$ via "*2"; and $L^3$, $L^4$ are independently selected from phenylene, biphenylene, fluoren-di-yl or a direct bond, preferably selected the same;

$R^5$, $R^6$ are independently selected from $C_1$ to $C_{12}$ alkyl, $C_1$ to $C_{12}$ alkoxy, $C_6$ to $C_{24}$ arylene and $C_2$ to $C_{21}$ heteroarylene, preferably from $C_6$ to $C_{12}$ arylene; and m is selected from 1 to 5, wherein m is an integer number.

According to another embodiment, $Ar^2$ is selected from D1 to D23.

According to another embodiment, $Ar^2$ is selected from D12 to D21.

According to another embodiment, $Ar^2$ is selected from D22 to D23.

According to another embodiment, compounds of formula 5 have a symmetry axis. A symmetry axis or mirror axis is a straight line, where an object can be mirrored without any geometrical changes. Objects that at least contain one of those axes are called symmetric.

Particularly high conductivity and low operating voltage may be achieved when compound of formula 1 or 4 is selected in this range.

According to another embodiment of the compound of formula 1 or 4, wherein $Ar^1$ has the formula 6:

(6)

wherein
$Ar^3$ is bonded at "*" via a single bond to $L^1$ and $L^2$,
$Ar^3$ is selected from $C_6$ to $C_{25}$ arylene or 9-phenylcarbazol-di-yl,
$Ar^4$ is selected from substituted or unsubstituted $C_{10}$ to $C_{24}$ arylene or $C_2$ to $C_{28}$ heteroarylene, preferably $C_3$ to $C_{21}$ heteroarylene, wherein the substitutents on $C_{10}$ to $C_{24}$ arylene or $C_2$ to $C_{28}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl.

According to another embodiment of formula 6, $Ar^3$ is selected from the following chemical structures G1 to G5:

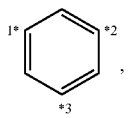

(G1)

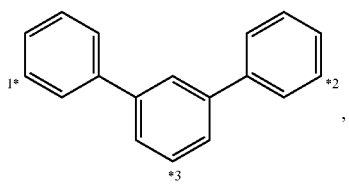

(G2)

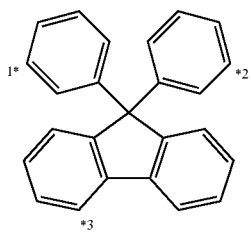

(G3)

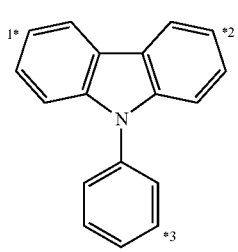

(G4)

and

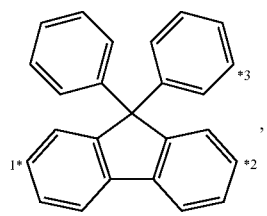

(G5)

wherein
$Ar^3$ is connected via a single bond to $L^1$ at "*¹", and $Ar^3$ connected via a single bond to $L^2$ at "*²", and $Ar^3$ is connected via a single bond to $Ar^4$ at "*³".

According to another embodiment, $Ar^4$ is selected from naphthalene, anthracene, tetraphene, tetracene, phenanthrene, pyrene, chrysene, perylene, triphenylene, pyridine, quinoline, quinozaline, pyrimidine, triazine, benzimidazole, benzothiazole, benzo[4,5]thieno[3,2-d]pyrimidine, carbazole, xanthene, phenoxazine, benzoacridine, dibenzoacridine, triazole.

According to another embodiment, $Ar^4$ is selected from naphthalene, anthracene, tetraphene, tetracene, phenanthrene, pyrene, chrysene, perylene, and triphenylene.

According to another embodiment, $Ar^4$ is selected from unsubstituted or substituted heteroarylene groups comprising at least one nitrogen or oxygen atom, preferably pyridine, quinoline, quinozaline, pyrimidine, triazine, benzimidazole, benzothiazole, benzo[4,5]thieno[3,2-d]pyrimidine, carbazole, xanthene, phenoxazine, benzoacridine, dibenzoacridine, triazole, preferably from pyrimidine or triazine, wherein the substituent is selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl.

Preferably, $Ar^4$ is bonded to $Ar^3$ via the heteroarylene group comprising at least one nitrogen or oxygen atom.

According to another embodiment, $Ar^4$ is selected from unsubstituted or substituted heteroarylene groups comprising at least one nitrogen atom, preferably pyridine, quinoline, quinozaline, pyrimidine, triazine, benzimidazole, benzo[4,5]thieno[3,2-d]pyrimidine, carbazole, xanthene, phenoxazine, benzoacridine, dibenzoacridine, triazole, preferably from pyrimidine or triazine, wherein the substituent is selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl.

Preferably, $Ar^4$ is bonded to $Ar^3$ via the heteroarylene group comprising at least one nitrogen atom.

According to an embodiment of formula 6, the substituents in $Ar^4$ are selected from phenyl, biphenyl, napthhyl, dibenzofuranyl and dibenzothiophenyl.

According to another embodiment of formula 6, wherein $Ar^4$ is selected from the chemical structures F1 to F31, and is connected with $Ar^3$ at "*" via a single bond:

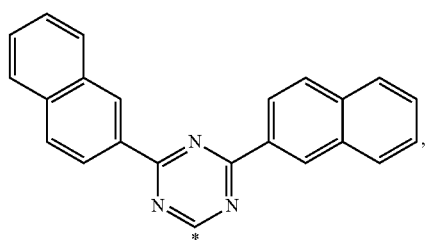

(F1)

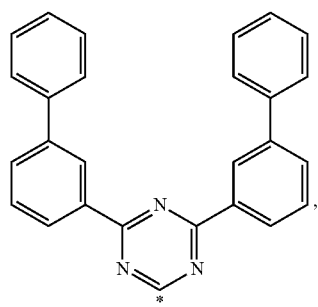 (F2)
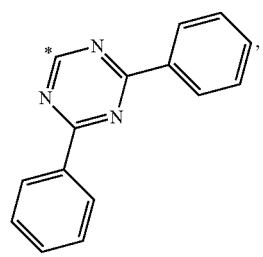 (F3)
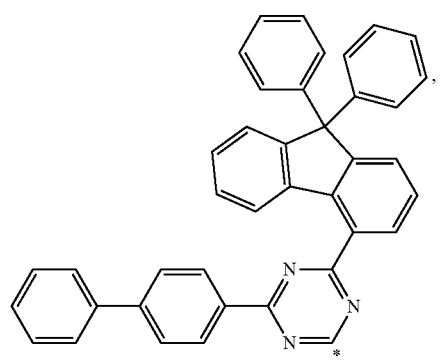 (F4)
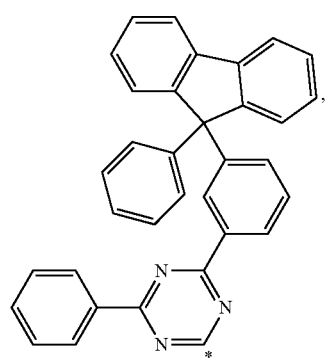 (F5)
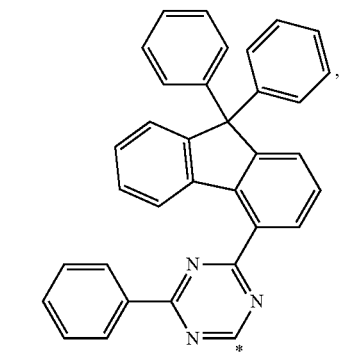 (F6)
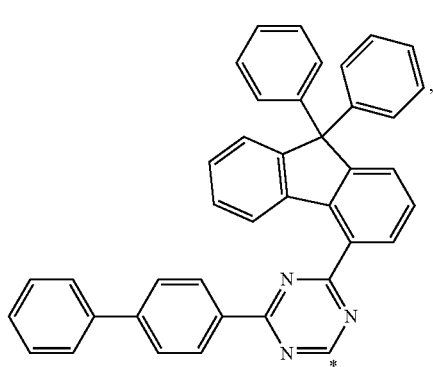 (F7)
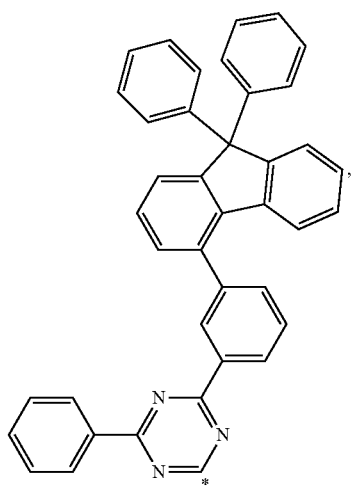 (F8)

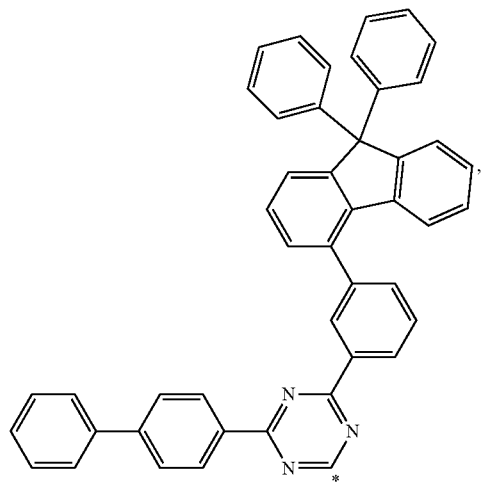
(F9)
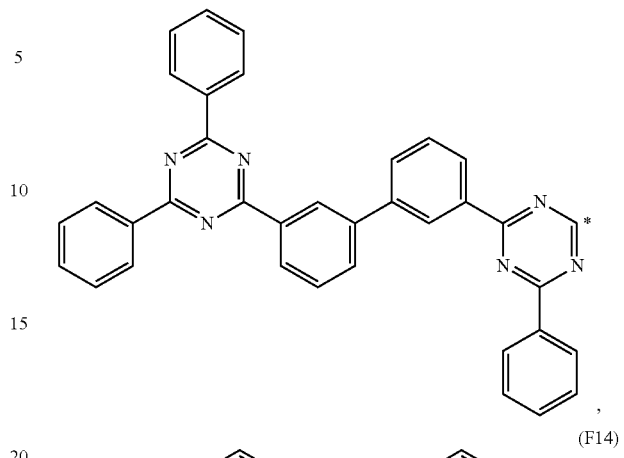
(F13)
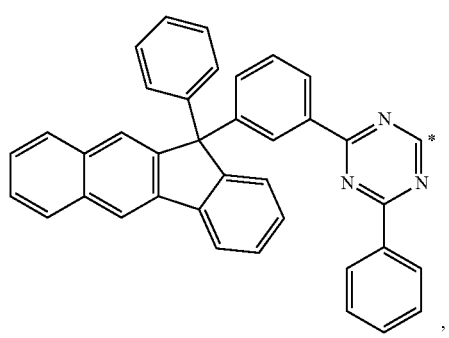
(F10)
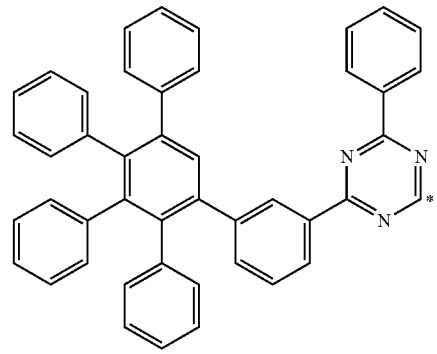
(F14)
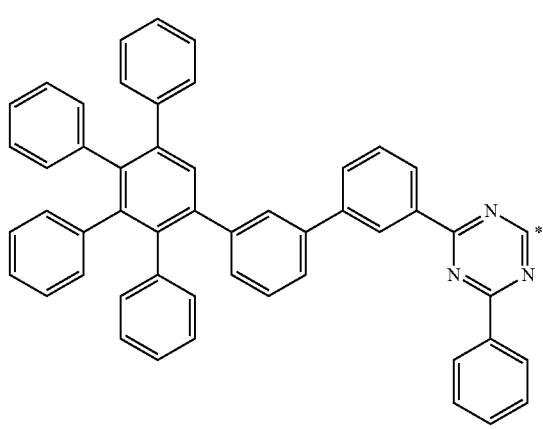
(F11)
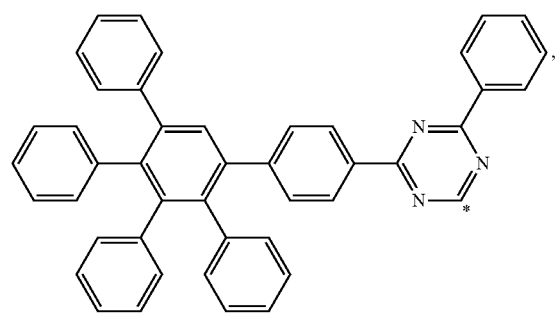
(F15)
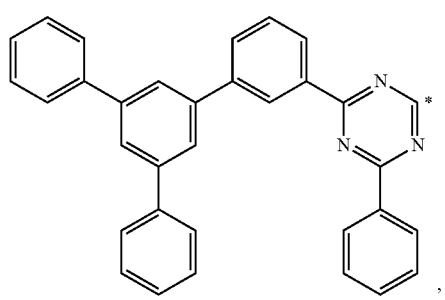
(F12)
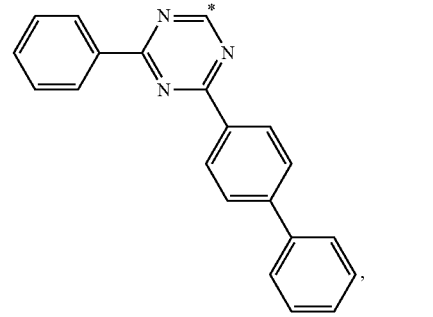
(F16)
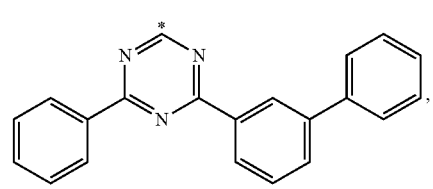
(F17)

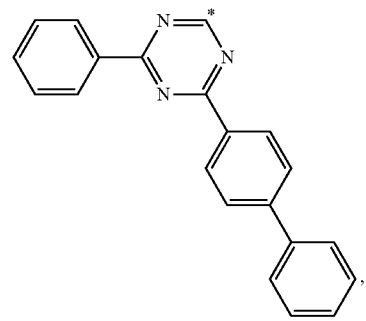
(F18)
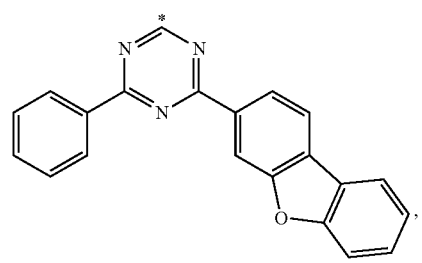
(F19)
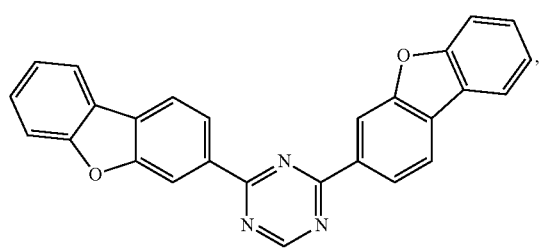
(F20)
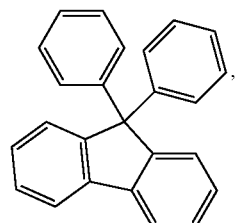
(F21)
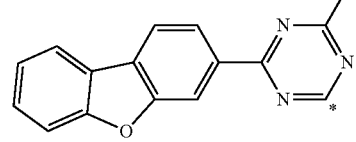
(F22)
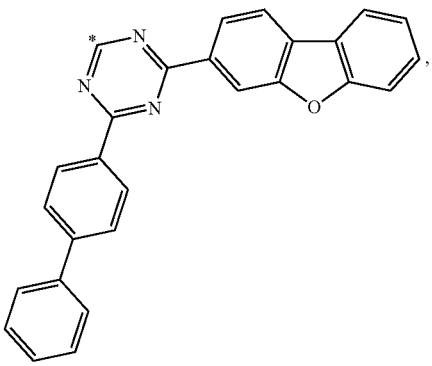
(F23)
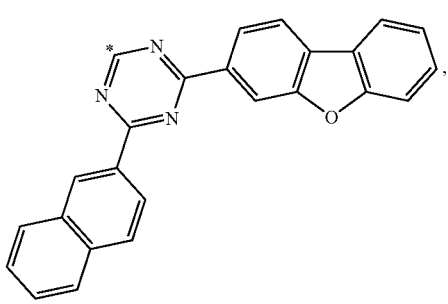
(F24)
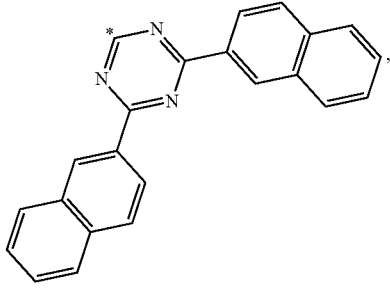
(F25)
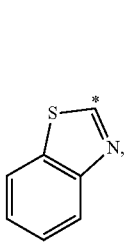
(F26)
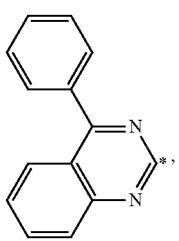
(F27)

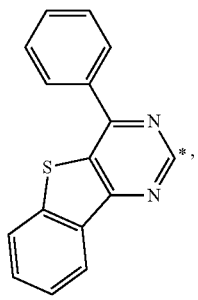 (F28)
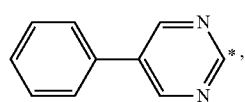 (F29)
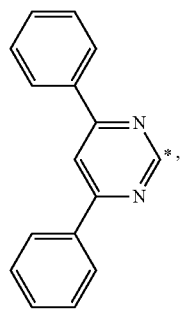 (F30)
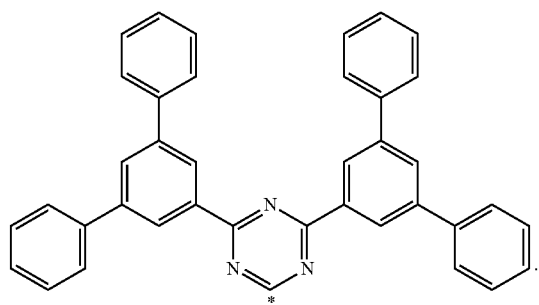 (F31)
According to another embodiment, wherein the compound of formula 1 or 4 is selected from the group of K1 to K42:
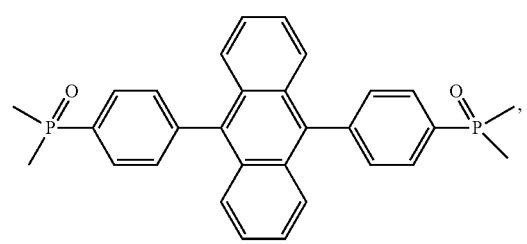 (K1)
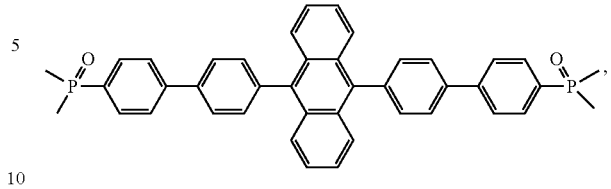 (K2)
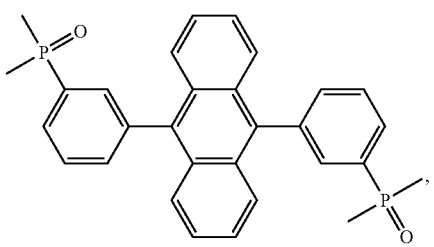 (K3)
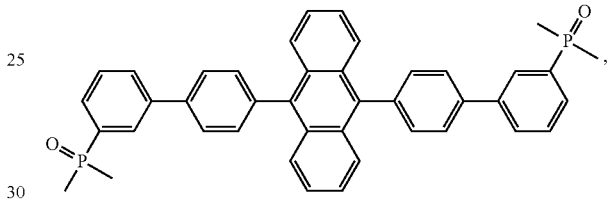 (K4)
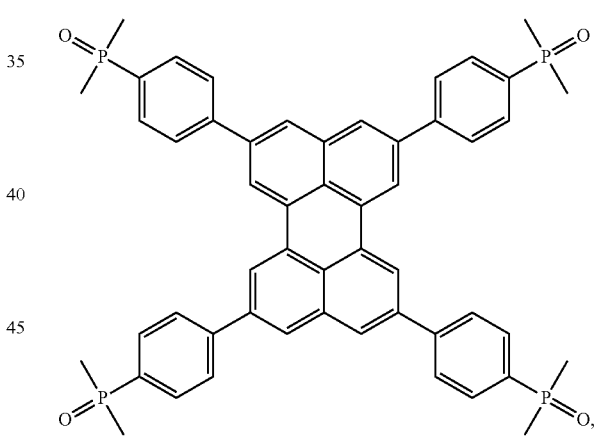 (K5)
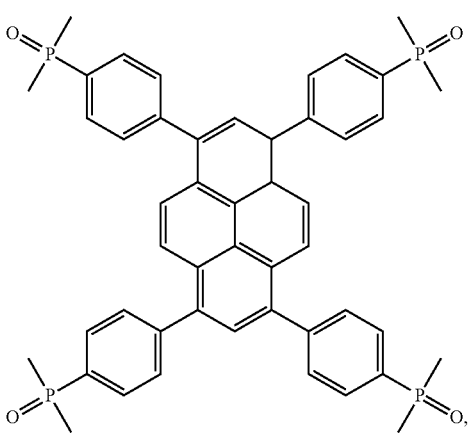 (K6)

(K7)
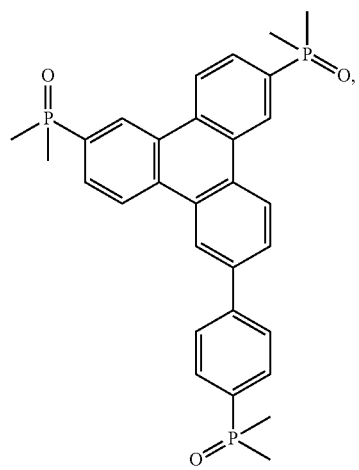
(K8)
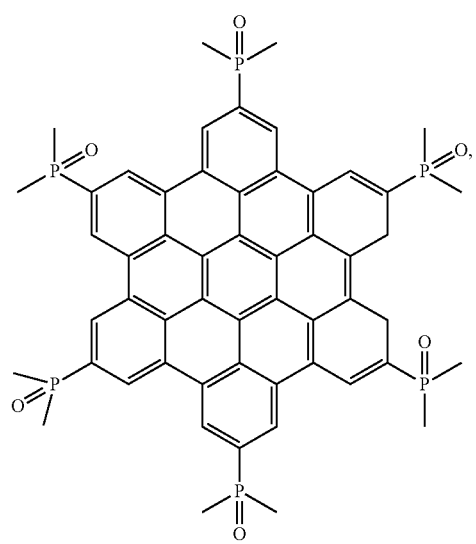
(K9)
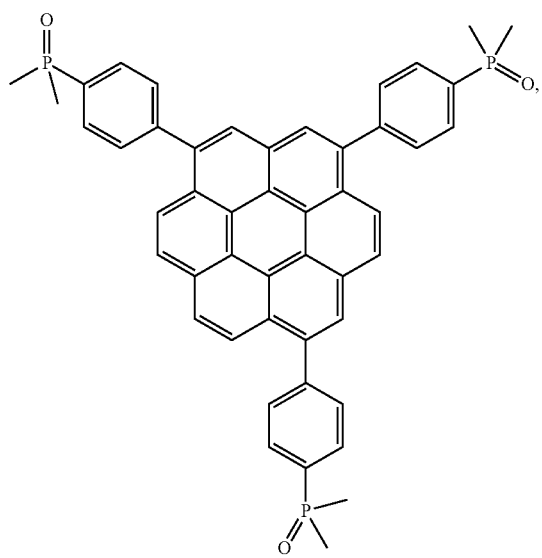
(K10)
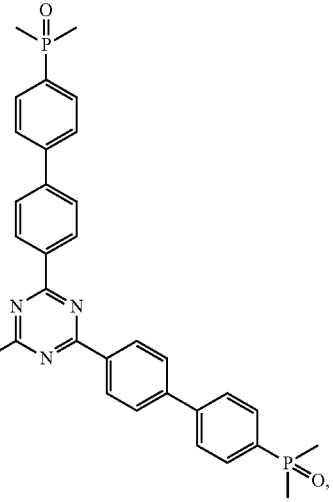
(K11)
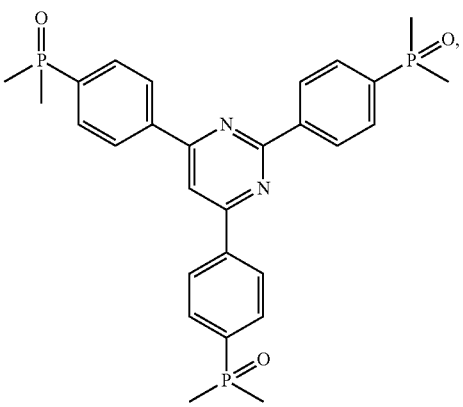
(K12)
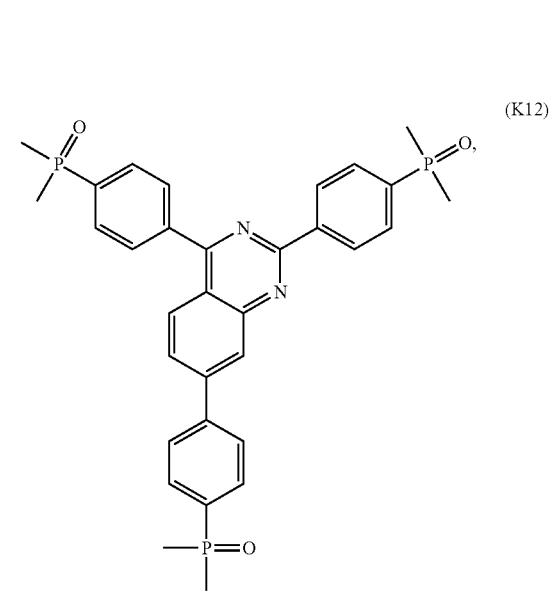

-continued
(K13)
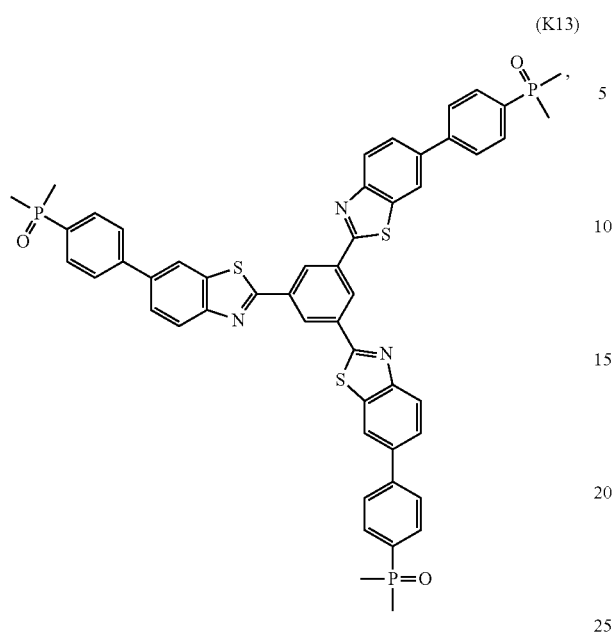
(K16)
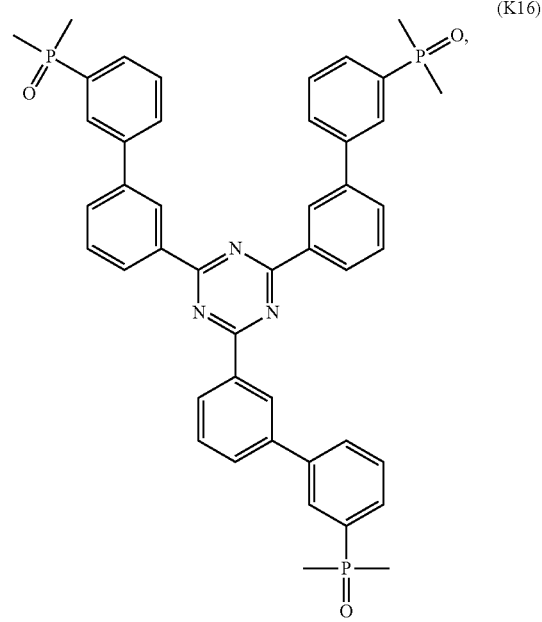
(K14)
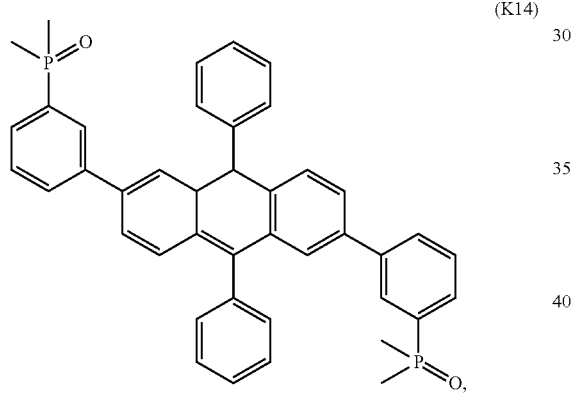
(K17)
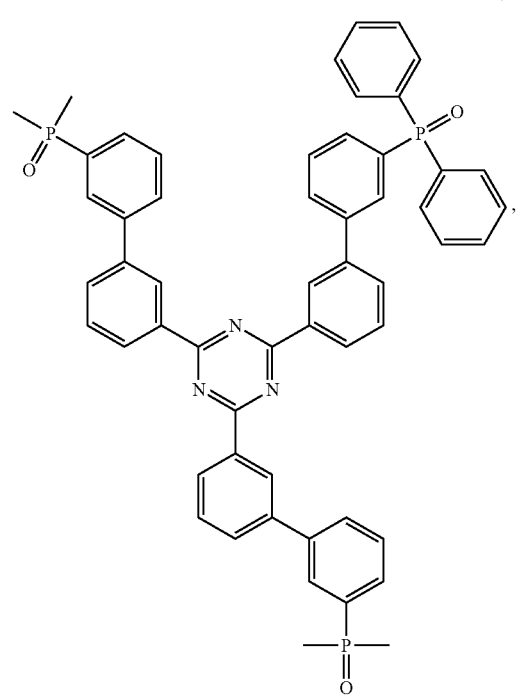
(K15)
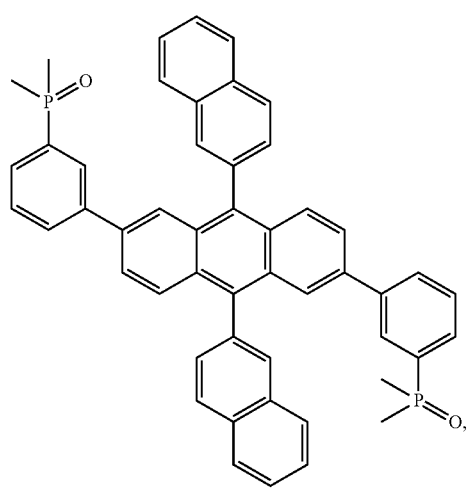

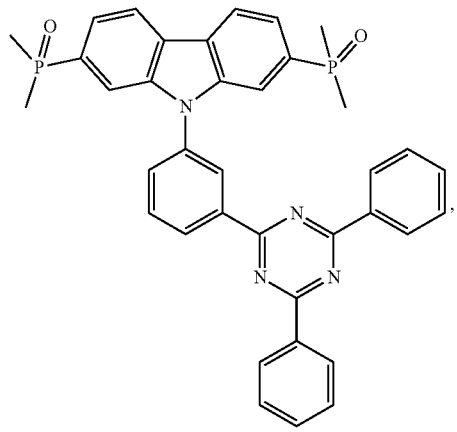
(K18)
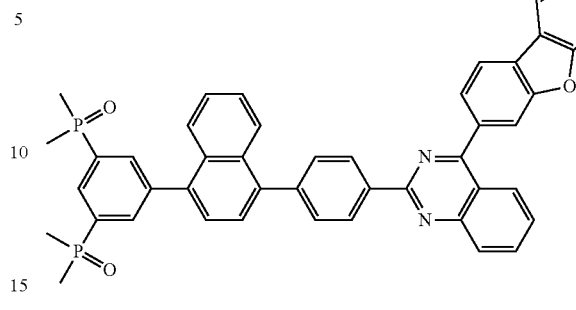
(K21)
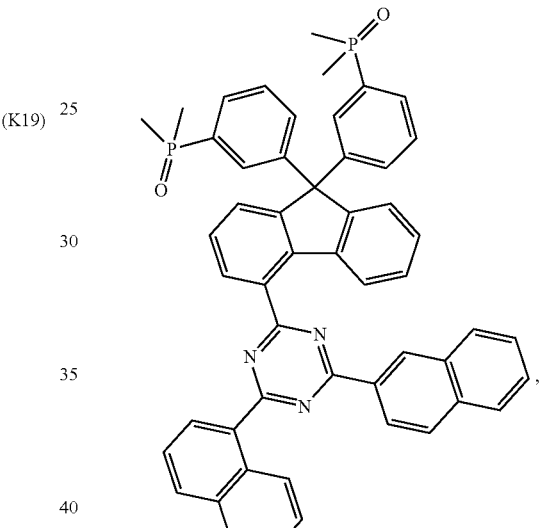
(K19)
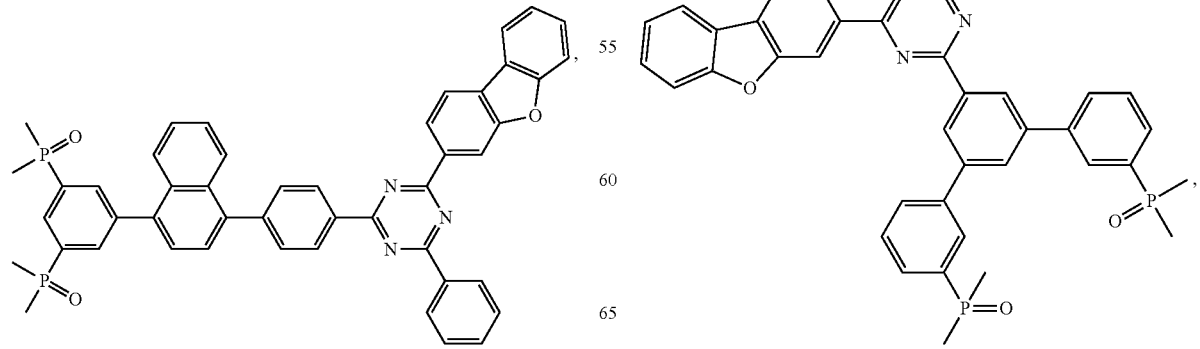
(K20)
(K22)
(K23)

-continued
(K24)
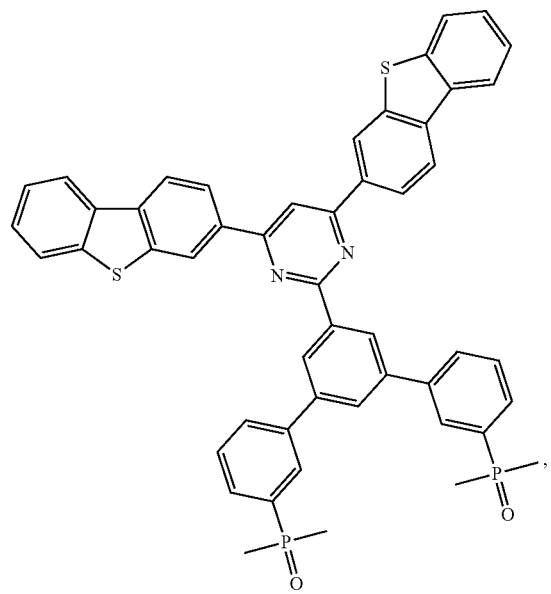
(K25)
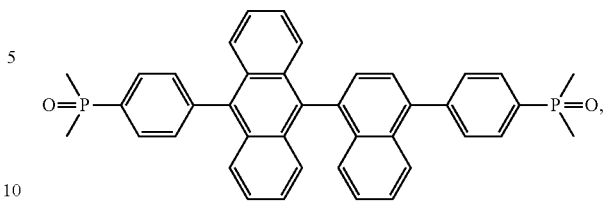
(K26)
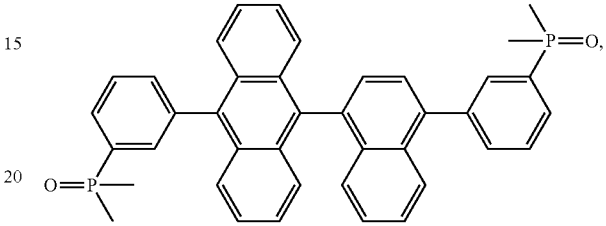
(K27)
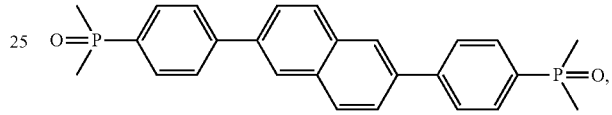
(K28)
(K29)
(K30)
(K31)
(K32)
(K33)

(K34)
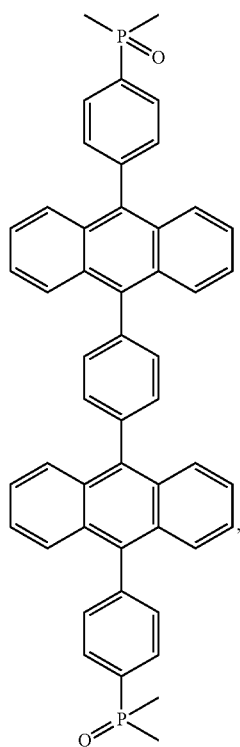
(K36)
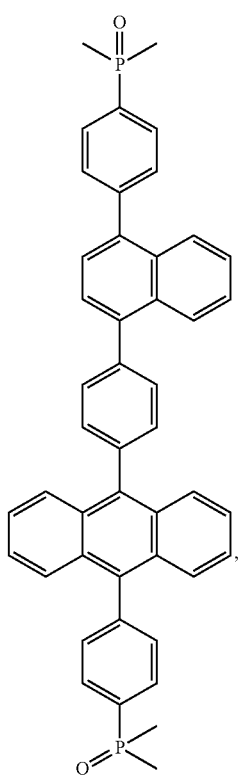
(K35)
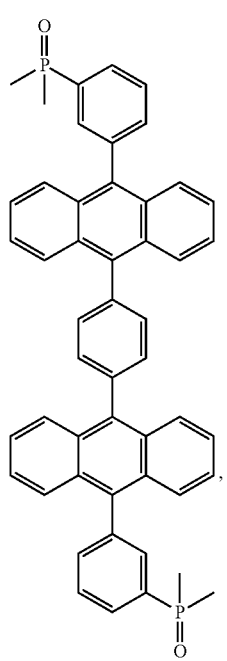
(K37)
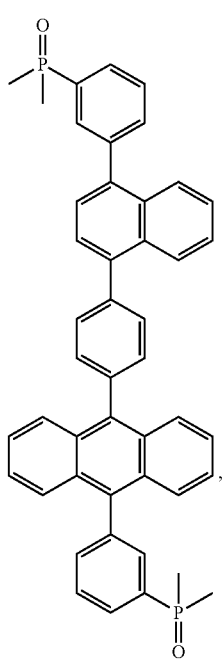

-continued (K38)
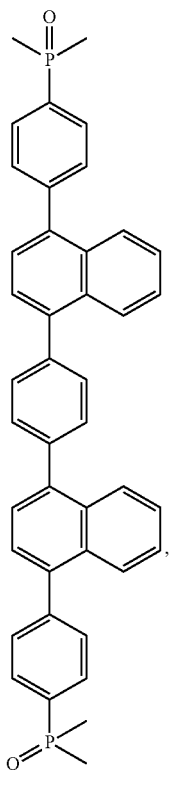

(K39)
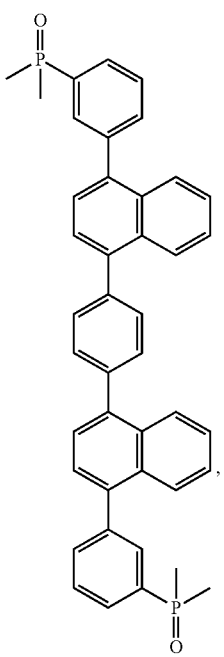

-continued (K40)
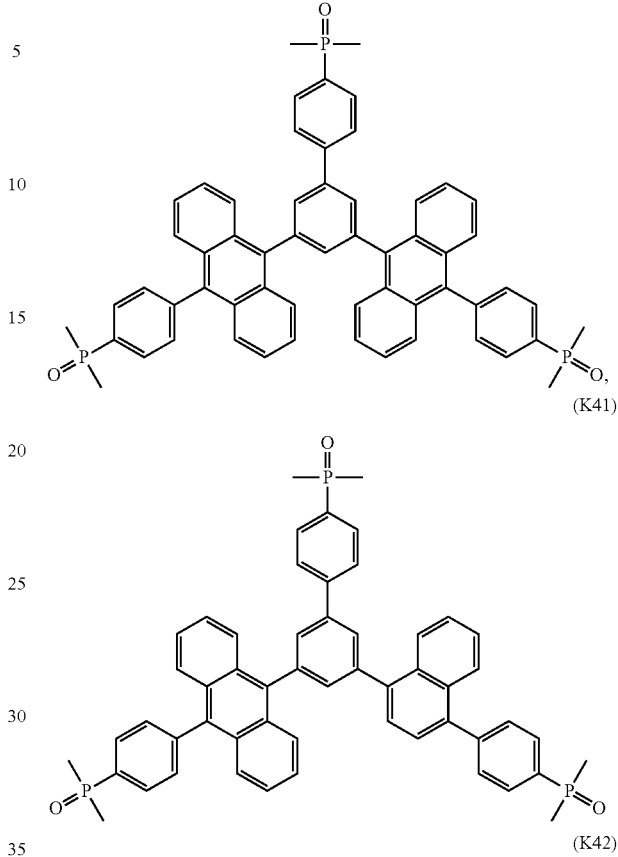

(K41), (K42)
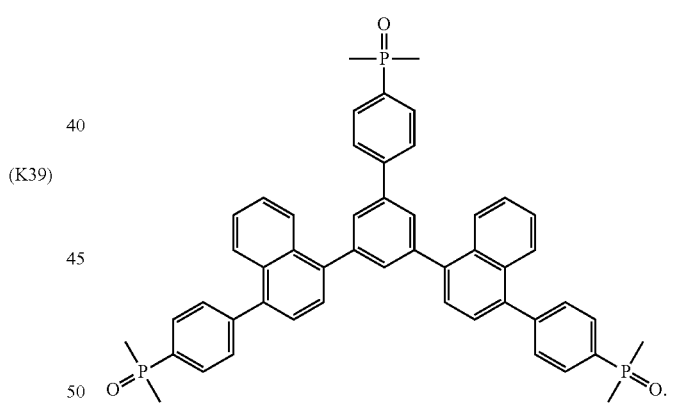

According to another embodiment an organic semiconductor material comprising the compound of formula 1 or 4 is provided.

According to another embodiment an electronic device comprising the compound of formula 1 or 4 is provided.

According to another embodiment an electronic device comprising an organic semiconductor material comprising the compound of formula 1 or 4 is provided.

According to another embodiment a device comprising an organic light-emitting diode comprising the compound of formula 1 or 4 is provided.

According to another embodiment a display device comprising the compound of formula 1 or 4 is provided.

According to another embodiment a method of manufacturing the same is provided.

According to another embodiment of the organic electronic device, wherein the organic semiconductor layer comprises a compound of formula 1 or 4.

According to another embodiment of the organic electronic device, wherein the organic semiconductor layer is an electron transport layer.

According to another embodiment of the organic electronic device, wherein the at least one organic semiconductor layer further comprises at least one metal, alkali halide and/or alkali organic complex.

According to another embodiment of the organic electronic device, wherein the at least one organic semiconductor layer further comprises at least one alkali halide or alkali organic complex.

According to another embodiment of the organic electronic device, wherein the at least one organic semiconductor layer further comprises at least one metal selected from alkali, alkaline earth, rare earth, transition or group III to VI metal, preferably at least one metal selected from alkali, alkaline earth or rare earth metal.

According to yet another embodiment, a display device comprising the organic optoelectronic device is provided.

According to another embodiment, an organic optoelectronic device comprises an anode layer and a cathode layer facing each other and at least one organic semiconductor layer between the anode layer and the cathode layer, wherein the organic semiconductor layer comprises the compound of formula 1 or 4.

According to another embodiment of the organic electronic device, wherein the organic semiconductor layer is arranged between a photoactive layer and the cathode layer.

A photoactive layer can be an emission layer or a light-absorbing layer.

According to another embodiment of the organic electronic device, wherein the electronic device comprises at least one organic semiconductor layer, at least one anode layer, at least one cathode layer and at least one emission layer, wherein the organic semiconductor layer is preferably arranged between the emission layer and the cathode layer.

According to another embodiment of the organic electronic device, wherein the organic electronic device further comprises an electron injection layer arranged between the at least one organic semiconductor layer and the cathode layer, wherein the electron injection layer comprises at least one metal and/or a metal halide or metal organic complex, wherein the metal is preferably selected from an alkali, alkaline earth or rare earth metal.

Preferably, the electron injection layer is essentially non-emissive or non-emissive.

Preferably, the organic semiconductor layer is arranged between the emission layer and the cathode layer and is essentially non-emissive or non-emissive.

Preferably, the organic semiconductor layer is arranged between the emission layer and the cathode layer and free of group III to VI, rare earth and transition metal compounds.

Preferably, the organic semiconductor layer is arranged between the emission layer and the cathode layer and is essentially non-emissive or non-emissive, wherein the organic semiconductor layer, the emission layer and the cathode layer may differ in their components and composition.

According to another embodiment, the organic semiconductor layer comprising the compound of formula 1 or 4 is in direct contact with the cathode electrode.

According to another embodiment, the organic semiconductor layer comprising the compound of formula 1 or 4 is in direct contact with the emission layer.

According to another embodiment, the organic semiconductor layer comprising the compound of formula 1 or 4 is in direct contact with the hole blocking layer.

According to another embodiment, the organic semiconductor layer comprising the compound of formula 1 or 4 is in direct contact with an electron transport auxiliary layer, wherein the electron transport auxiliary layer is in direct contact with the emission layer.

According to another embodiment, the organic semiconductor layer comprising the compound of formula 1 or 4 is in direct contact with the electron injection layer.

According to another embodiment, the organic semiconductor layer comprising the compound of formula 1 or 4 is contacting sandwiched between the electron transport auxiliary layer and the electron injection layer.

According to another embodiment, the organic semiconductor layer comprising the compound of formula 1 or 4 is contacting sandwiched between the electron transport auxiliary layer and the electron injection layer and the organic semiconductor layer further comprises an alkali halide or alkali organic complex.

According to another embodiment, the organic semiconductor layer comprising the compound of formula 1 or 4 is contacting sandwiched between the electron transport auxiliary layer and the cathode layer.

According to another embodiment, the organic semiconductor layer comprising the compound of formula 1 or 4 is contacting sandwiched between the electron transport auxiliary layer and the cathode layer and the organic semiconductor layer further comprises an alkali halide or alkali organic complex.

Hereinafter, an organic optoelectronic device according to another embodiment is described.

An organic optoelectronic device according to another embodiment comprises an anode layer and a cathode layer facing each other and at least one organic semiconductor layer between the anode layer and the cathode layer and the organic semiconductor layer comprises the compound for an organic optoelectronic device.

The compound for an organic optoelectronic device represented by formula 1 or 4 may be appropriate for an organic semiconductor layer of an organic optoelectronic device, for example, a host of an emission layer, an electron transport layer, an electron injection layer or an electron transport auxiliary layer.

According to another embodiment of the organic electronic device, wherein the electronic device is a light emitting device, thin film transistor, a battery, a display device or a photovoltaic cell and preferably a light emitting device.

According to another aspect, a compound of formula 1 is provided:

$$L^1\text{-}Ar^1\text{-}[L^2]_n \qquad (1),$$

wherein
$L^1$ has the formula 2:

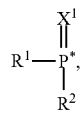

(2)

and
$L^2$ has the formula 3:

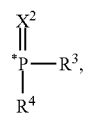

(3)

wherein
L¹ and L² are bonded at "*" via a single bond independently to the same or different arylene groups or heteroarylenes group of Ar¹; and wherein
$X^1$, $X^2$ are independently selected from O, S and Se;

$Ar^1$ is selected from substituted or unsubstituted $C_{20}$ to $C_{52}$ arylene or $C_{14}$ to $C_{64}$ heteroarylene, wherein the substituent of the substituted $C_{20}$ to $C_{52}$ arylene or $C_{14}$ to $C_{64}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl;

$R^1$, $R^2$ are independently selected from substituted or unsubstituted $C_1$ to $C_{16}$ alkyl, wherein the substituent of substituted $C_1$ to $C_{16}$ alkyl is selected from $C_6$ to $C_{18}$ arylene or $C_2$ to $C_{12}$ heteroarylene;

$R^3$, $R^4$ are independently selected from substituted or unsubstituted $C_1$ to $C_{16}$ alkyl, substituted or unsubstituted $C_6$ to $C_{18}$ arylene, $C_2$ to $C_{20}$ heteroarylene, wherein the substituent of substituted $C_1$ to $C_{16}$ alkyl, the substituent of the substituted $C_6$ to $C_{18}$ arylene, $C_2$ to $C_{20}$ heteroarylene are independently selected from $C_6$ to $C_{18}$ arylene or $C_2$ to $C_{12}$ heteroarylene;

n is selected from 1 to 5, wherein n is an integer number.

According to another embodiment, compound of formula 1 and/or 4 is free of metal cations and/or NR', SR' and/or $NO_2$ groups, wherein R' is selected from H, alkyl or aryl.

Advantageous Effects

Surprisingly, it was found that the compounds of formula 1 or 4 and the inventive organic electronic device solve the problem underlying the present invention by being superior over the organic electroluminescent devices and compounds known in the art, in particular with respect to conductivity, operating voltage and/or cd/A efficiency. Increased conductivity and reduced operating voltage are important for reducing power consumption and increasing battery life, for example of a mobile display device. High cd/A efficiency is important for high efficiency and thereby increased battery life of a mobile device, for example a mobile display device.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned properties of operating voltage and/or cd/A efficiency. These compounds are discussed herein to be particularly preferred.

Further an organic optoelectronic device having high efficiency and/or long life-span may be realized.

Hereinafter, a compound for an organic optoelectronic device according to an embodiment is described.

A compound for an organic optoelectronic device according to an embodiment is represented by formula 1 or 4 according to the invention.

The compound of the invention of formula 1 or 4 may help injection or transport of electrons or increases a glass transition temperature of the compound, and thus luminance efficiency may be increased due to suppression of an intermolecular interaction, and the compound may have a low deposition temperature relative to the molecular weight.

Accordingly, when the compound for an organic optoelectronic device represented by formula 1 or 4 forms a film, the compound may facilitate injection and transport of electrons in the device due to the reduced steric hindrance of dialkyl PO groups compared to diphenyl PO groups. Thereby, a higher density of electron transporting heteroarylene groups may be achieved.

Therefore, when the compound of formula 1 or 4 are used for an organic optoelectronic device these compounds may decrease the operating voltage of the device due to excellent electron transport characteristics and increase luminance efficiency due to rapid injection of electrons into an emission layer. On the other hand, when the compound is mixed with a material having excellent hole injection and transport characteristics to form the emission layer, the compound may also decrease the operating voltage due to excellent electron transport capability and obtain excellent luminance efficiency due to efficient charge injection and formation of excitons. In addition, excellent electron injection and transport characteristics of the compound for an organic optoelectronic device represented by formula 1 or 4 may be obtained. In addition, the compound of formula 1 or 4 may still maintain excellent electron injection and transport characteristics even when used to from an electron injection auxiliary layer or to form an emission layer as a mixture with a compound having excellent hole characteristics.

The compound for an organic optoelectronic device represented by formula 1 or 4 may include at least 4 to about 15, preferably at least 5 to about 8, substituted or unsubstituted $C_6$ to $C_{18}$ arylene groups.

Particularly good performance characteristics are obtained when the compound of formula 1 or 4 is selected in this range.

The compound for an organic optoelectronic device represented by formula 1 or 4 may have a molecular weight (Mw) of ≥400 to ≤1800 g/mol, and preferably ≥420 to ≤1400 g/mol, more preferred ≥450 to ≤1000 g/mol, also preferred ≥420 to ≤850 g/mol.

If the molecular weight is selected in this range, particularly reproducible evaporation and deposition can be achieved in vacuum at temperatures where good long-term stability is observed.

Anode

A material for the anode may be a metal or a metal oxide, or an organic material, preferably a material with work function above about 4.8 eV, more preferably above about 5.1 eV, most preferably above about 5.3 eV. Preferred metals are noble metals like Pt, Au or Ag, preferred metal oxides are transparent metal oxides like ITO or IZO which may be advantageously used in bottom-emitting OLEDs having a reflective cathode.

In devices comprising a transparent metal oxide anode or a reflective metal anode, the anode may have a thickness from about 50 nm to about 100 nm, whereas semitransparent metal anodes may be as thin as from about 5 nm to about 15 nm.

Hole Injection Layer

The hole injection layer may improve interface properties between the anode and an organic material used for the hole transport layer, and is applied on a non-planarized anode and thus may planarize the surface of the anode. For example, the hole injection layer may include a material having a median value of the energy level of its highest occupied molecular orbital (HOMO) between the work function of the anode material and the energy level of the HOMO of the hole transport layer, in order to adjust a difference between the work function of the anode and the energy level of the HOMO of the hole transport layer.

When the hole transport region comprises a hole injection layer 36, the hole injection layer may be formed on the anode by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-6}$ Pa to about $10^{-1}$ Pa, and a deposition rate of about 0.1 to about 10 nm/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

The hole injection layer may further comprise a p-dopant to improve conductivity and/or hole injection from the anode.

p-dopant

In another aspect, the p-dopant may be homogeneously dispersed in the hole injection layer.

In another aspect, the p-dopant may be present in the hole injection layer in a higher concentration closer to the anode and in a lower concentration closer to the cathode.

The p-dopant may be one of a quinone derivative, a radialene compound. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ).

Hole Transport Layer

Conditions for forming the hole transport layer and the electron blocking layer may be defined based on the above-described formation conditions for the hole injection layer.

A thickness of the hole transport part of the charge transport region may be from about 10 nm to about 1000 nm, for example, about 10 nm to about 100 nm. When the hole transport part of the charge transport region comprises the hole injection layer and the hole transport layer, a thickness of the hole injection layer may be from about 10 nm to about 1000 nm, for example about 10 nm to about 100 nm and a thickness of the hole transport layer may be from about 5 nm to about 200 nm, for example about 10 nm to about 150 nm. When the thicknesses of the hole transport part of the charge transport region, the HIL, and the HTL are within these ranges, satisfactory hole transport characteristics may be obtained without a substantial increase in operating voltage.

Hole transport matrix materials used in the hole transport region are not particularly limited. Preferred are covalent compounds comprising a conjugated system of at least 6 delocalized electrons, preferably organic compounds comprising at least one aromatic ring, more preferably organic compounds comprising at least two aromatic rings, even more preferably organic compounds comprising at least three aromatic rings, most preferably organic compounds comprising at least four aromatic rings. Typical examples of hole transport matrix materials which are widely used in hole transport layers are polycyclic aromatic hydrocarbons, triarylene amine compounds and heterocyclic aromatic compounds. Suitable ranges of frontier orbital energy levels of hole transport matrices useful in various layer of the hole transport region are well-known. In terms of the redox potential of the redox couple HTL matrix/cation radical of the HTL matrix, the preferred values (if measured for example by cyclic voltammetry against ferrocene/ferrocenium redox couple as reference) may be in the range 0.0-1.0 V, more preferably in the range 0.2-0.7 V, even more preferably in the range 0.3-0.5 V.

Buffer Layer

The hole transport part of the charge transport region may further include a buffer layer.

Buffer layer that can be suitable used are disclosed in U.S. Pat. Nos. 6,140,763, 6,614,176 and in US2016/248022.

The buffer layer may compensate for an optical resonance distance of light according to a wavelength of the light emitted from the EML, and thus may increase efficiency.

Emission Layer

The emission layer (EML) may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and an emitter dopant (further only emitter).

Emitter Host

According to another embodiment, the emission layer comprises compound of formula 1 or 4 as emitter host.

The emitter host compound has at least three aromatic rings, which are independently selected from carbocyclic rings and heterocyclic rings.

Other compounds that can be used as the emitter host is an anthracene matrix compound represented by formula 400 below:

Formula 400

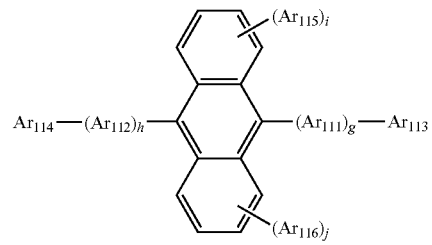

In formula 400, $Ar_{111}$ and $Ar_{112}$ may be each independently a substituted or unsubstituted $C_6$-$C_{60}$ aryleneene group; $Ar_{113}$ to $Ar_{116}$ may be each independently a substituted or unsubstituted $C_1$-$C_{10}$ alkyl group or a substituted or unsubstituted $C_6$-$C_{60}$ arylene group; and g, h, i, and j may be each independently an integer from 0 to 4.

In some embodiments, $Ar_{111}$ and $Ar_{112}$ in formula 400 may be each independently one of a phenylene group, a naphthylene group, a phenanthrenylene group, or a pyrenylene group; or a phenylene group, a naphthylene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2.

In formula 400, $Ar_{113}$ to $Ar_{116}$ may be each independently one of

- a $C_1$-$C_{10}$ alkyl group substituted with at least one of a phenyl group, a naphthyl group, or an anthryl group;
- a phenyl group, a naphthyl group, an anthryl group, a pyrenyl group, a phenanthrenyl group, or a fluorenyl group;
- a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof,
- a sulfonic acid group or a salt thereof, a phosphoric acid group or a salt thereof,
- a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or
- a fluorenyl group or

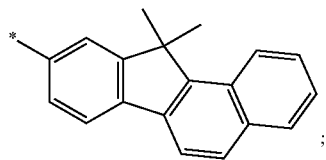 [SMILES: *c1ccc2c(c1)C(C)(C)c1c-2ccc2ccccc12]

formulas 7 or 8
(7), (8).

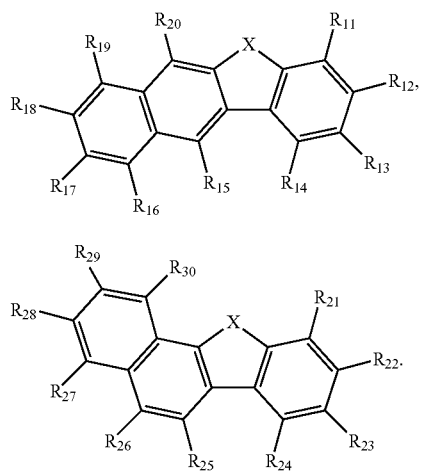

(7)

(8)

Wherein in the formulas 7 and 8, X is selected form an oxygen atom and a sulfur atom, but embodiments of the invention are not limited thereto.

In the formula 7, any one of $R_{11}$ to $R_{14}$ is used for bonding to $Ar_{111}$. $R_{11}$ to $R_{14}$ that are not used for bonding to $Ar_{111}$ and $R_{15}$ to $R_{20}$ are the same as $R_1$ to $R_8$.

In the formula 8, any one of $R_{21}$ to $R_{24}$ is used for bonding to $Ar_{111}$. $R_{21}$ to $R_{24}$ that are not used for bonding to $Ar_{111}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

The emitter host compound may have a dipole moment in the range from about ≥0 Debye to about ≤2.0 Debye.

Preferably, the dipole moment of the EML host is selected ≥0.2 Debye and ≤1.45 Debye, preferably ≥0.4 Debye and ≤1.2 Debye, also preferred ≥0.6 Debye and ≤1.1 Debye.

The dipole moment is calculated using the optimized using the hybrid functional B3LYP with the 6-31G* basis set as implemented in the program package TURBOMOLE V6.5. If more than one conformation is viable, the conformation with the lowest total energy is selected to determine the dipole moment of the molecules. Using this method, 2-(10-phenyl-9-anthracenyl)-benzo[b]naphtho[2,3-d]furan (CAS 1627916-48-6) has a dipole moment of 0.88 Debye, 2-(6-(10-phenylanthracen-9-yl)naphthalen-2-yl)dibenzo[b, d]thiophene (CAS 1838604-62-8) of 0.89 Debye, 2-(6-(10-phenylanthracen-9-yl)naphthalen-2-yl)dibenzo[b,d]furan (CAS 1842354-89-5) of 0.69 Debye, 2-(7-(phenanthren-9-yl)tetraphen-12-yl)dibenzo[b,d]furan (CAS 1965338-95-7) of 0.64 Debye, 4-(4-(7-(naphthalen-1-yl)tetraphen-12-yl) phenyl) dibenzo[b,d]furan (CAS 1965338-96-8) of 1.01 Debye.

Emitter Dopant

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The emitter may be a red, green, or blue emitter.

The dopant may be a fluorescent dopant, for example ter-fluorene, the structures are shown below. 4,4'-bis(4-diphenyl amiostyryl)biphenyl (DPAVBI, 2,5,8,11-tetra-tert-butyl perylene (TBPe), and Compound 8 below are examples of fluorescent blue dopants.

Compound 8

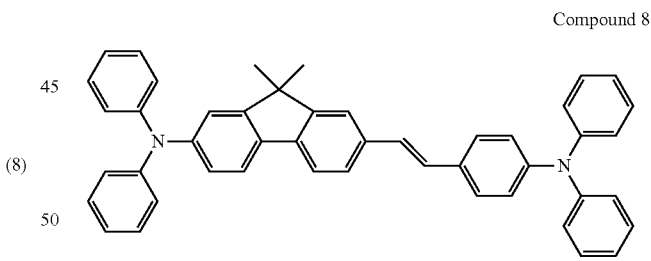

The dopant may be a phosphorescent dopant, and examples of the phosphorescent dopant may be an organic metal compound comprising Ir, Pt, Os, Ti, Zr, Hf, Eu, Tb, Tm, Fe, Co, Ni, Ru, Rh, Pd, or a combination thereof. The phosphorescent dopant may be, for example a compound represented by formula Z, but is not limited thereto:

$$J_2MX \quad (Z).$$

In formula Z, M is a metal, and J and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the J and X may be, for example a bidendate ligand.

Electron Transport Layer

According to another embodiment, the organic semiconductor layer comprising a compound of formula 1 or 4 is an electron transport layer.

For example, an organic light emitting diode according to an embodiment of the present invention comprises at least one electron transport layer, and in this case, the electron transport layer comprises a compound of formula 1 or 4, or preferably of at least one compound of formulae F1 to F24.

In another embodiment, the organic electronic device comprises an electron transport region of a stack of organic layers formed by two or more electron transport layers, wherein at least one electron transport layer comprises a compound of formula 1 or 4.

The electron transport layer may include one or two or more different electron transport compounds.

According to another embodiment, the second electron transport layer (162) comprises at least one compound of formula 1 or 4 according to the invention and the first electron transport layer (161) comprises a matrix compound, which is selected different to the compound of formula 1 or 4 according to the invention, and may be selected from:
- an anthracene based compound or a hetero substituted anthracene based compound, preferably 2-(4-(9,10-di(naphthalen-2-yl)anthracene-2-yl)phenyl)-1-phenyl-1H-benzo[d]imidazole and/or N4,N4"-di(naphthalen-1-yl)-N4,N4"-diphenyl-[1,1':4',1"-terphenyl]-4,4"-diamine.

According to another embodiment, the first electron transport layer (161) comprises at least one compound of formula 1 or 4 according to the invention and the second electron transport layer (162) comprises a matrix compound, which is selected different to the compound of formula 1 or 4 according to the invention, and may be selected from:
- a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d: 1',2'-f]phosphepine-3-oxide; or
- a substituted phenanthroline compound, preferably 2,4,7,9-tetraphenyl-1,10-phenanthroline or 2,9-di(biphenyl-4-yl)-4,7-diphenyl-1,10-phenanthroline.

According to another embodiment the first electron transport layer comprises at least one compound of formula 1 or 4 according to the invention and the second electron transport layer comprises a matrix compound, which is selected different to the compound of formula 1 or 4 according to the invention, and may be selected from a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide.

According to another embodiment, the first and second electron transport layers comprise a compound of formula 1 or 4, wherein the compound of formula 1 or 4 is not selected the same.

The thickness of the first electron transport layer (161) may be from about 0.5 nm to about 100 nm, for example about 2 nm to about 30 nm. When the thickness of the first electron transport layer (161) is within these ranges, the first electron transport layer (161) may have improved electron transport ability without a substantial increase in operating voltage.

A thickness of the optional second electron transport layer (162) may be about 1 nm to about 100 nm, for example about 2 nm to about 20 nm. When the thickness of the electron transport layer is within these ranges, the electron transport layer may have satisfactory electron transporting ability without a substantial increase in operating voltage.

The electron transport layer may further comprise an alkali halide and/or alkali organic complex.

According to another embodiment, the first and second electron transport layers comprise a compound of formula 1 or 4, wherein the second electron transport layer (162) further comprises an alkali halide and/or alkali organic complex.

Alkali Halide

Alkali halides, also known as alkali metal halides, are the family of inorganic compounds with the chemical formula MX, where M is an alkali metal and X is a halogen.

M can be selected from Li, Na, Potassium, Rubidium and Cesium.

X can be selected from F, Cl, Br and J.

According to various embodiments of the present invention a lithium halide may be preferred. The lithium halide can be selected from the group comprising LiF, LiCl, LiBr and LiJ. However, most preferred is LiF.

The alkali halide is essentially non-emissive or non-emissive.

Alkali Organic Complex

According to various embodiments of the present invention the organic ligand of the lithium organic complex is a quinolate, a borate, a phenolate, a pyridinolate or a Schiff base ligand;

preferably the lithium quinolate complex has the formula III, IV or V:

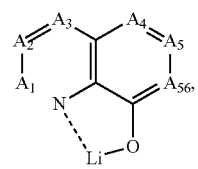

(III)

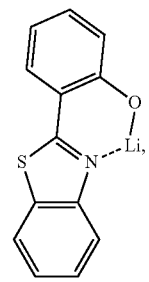

(IV)

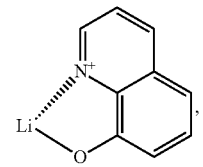

(V)

wherein
- $A_1$ to $A_6$ are same or independently selected from CH, CR, N, O;
- R is same or independently selected from hydrogen, halogen, alkyl or arylene or heteroarylene with 1 to 20 carbon atoms; and more preferred A1 to A6 are CH;
- preferably the borate based organic ligand is a tetra(1H-pyrazol-1-yl)borate;

preferably the phenolate is a 2-(pyridin-2-yl)phenolate, a 2-(diphenylphosphoryl)phenolate, an imidazol phenolates, or 2-(pyridin-2-yl)phenolate and more preferred 2-(1-phenyl-1H-benzo[d]imidazol-2-yl)phenolate;

preferably the pyridinolate is a 2-(diphenylphosphoryl) pyridin-3-olate.

According to various embodiments of the present invention the organic ligand of the alkali organic complex, preferably of a lithium organic complex, can be a quinolate. Quinolates that can be suitable used are disclosed in WO 2013079217 A1 and incorporated by reference.

According to various embodiments of the present invention the organic ligand of the lithium organic complex can be a borate based organic ligand, Preferably the lithium organic complex is a lithium tetra(1H-pyrazol-1-yl)borate. Borate based organic ligands that can be suitable used are disclosed in WO 2013079676 A1 and incorporated by reference.

According to various embodiments of the present invention the organic ligand of the lithium organic complex can be a phenolate ligand, Preferably the lithium organic complex is a lithium 2-(diphenylphosphoryl)phenolate. Phenolate ligands that can be suitable used are disclosed in WO 2013079678 A1 and incorporated by reference.

Further, phenolate ligands can be selected from the group of pyridinolate, preferably 2-(diphenylphosphoryl)pyridin-3-olate. Pyridine phenolate ligands that can be suitable used are disclosed in JP 2008195623 and incorporated by reference.

In addition, phenolate ligands can be selected from the group of imidazol phenolates, preferably 2-(1-phenyl-1H-benzo[d]imidazol-2-yl)phenolate. Imidazol phenolate ligands that can be suitable used are disclosed in JP 2001291593 and incorporated by reference.

Also, phenolate ligands can be selected from the group of oxazol phenolates, preferably 2-(benzo[d]oxazol-2-yl)phenolate. Oxazol phenolate ligands that can be suitable used are disclosed in US 20030165711 and incorporated by reference.

The alkali organic complex may be essentially non-emissive or non-emissive.

n-dopant

According to various embodiments, the organic semiconductor layer comprising a compound of formula 1 or 4 may further comprise an n-dopant.

Electrically neutral metal complexes suitable as n-dopants may be e.g. strongly reductive complexes of some transition metals in low oxidation state. Particularly strong n-dopants may be selected for example from Cr(II), Mo(II) and/or W(II) guanidinate complexes such as $W_2(hpp)_4$, as described in more detail in WO2005/086251.

Electrically neutral organic radicals suitable as n-dopants may be e.g. organic radicals created by supply of additional energy from their stable dimers, oligomers or polymers, as described in more detail in EP 1 837 926 B1, WO2007/107306, or WO2007/107356. Specific examples of such suitable radicals may be diazolyl radicals, oxazolyl radicals and/or thiazolyl radicals.

In another embodiment, the organic semiconductor layer may further comprise an elemental metal. An elemental metal is a metal in a state of metal in its elemental form, a metal alloy, or a metal cluster. It is understood that metals deposited by vacuum thermal evaporation from a metallic phase, e.g. from a bulk metal, vaporize in their elemental form. It is further understood that if the vaporized elemental metal is deposited together with a covalent matrix, the metal atoms and/or clusters are embedded in the covalent matrix.

In other words, it is understood that any metal doped covalent material prepared by vacuum thermal evaporation contains the metal at least partially in its elemental form.

For the use in consumer electronics, only metals containing stable nuclides or nuclides having very long halftime of radioactive decay might be applicable. As an acceptable level of nuclear stability, the nuclear stability of natural potassium can be taken.

In one embodiment, the n-dopant is selected from electropositive metals selected from alkali metals, alkaline earth metals, rare earth metals and metals of the first transition period Ti, V, Cr and Mn. Preferably, the n-dopant is selected from Li, Na, K, Rb, Cs, Mg, Ca, Sr, Ba, Sm, Eu, Tm, Yb; more preferably from Li, Na, K, Rb, Cs, Mg and Yb, even more preferably from Li, Na, Cs and Yb, most preferably from Li, Na and Yb.

The n-dopant may be essentially non-emissive or non-emissive.

Electron Injection Layer

According to another aspect of the invention, the organic electroluminescent device may further comprise an electron injection layer between the first electron transport layer (first-ETL) and the cathode.

The electron injection layer (EIL) may facilitate injection of electrons from the cathode.

According to another aspect of the invention, the electron injection layer comprises:

(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or (ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer (second-ETL) is identical with the alkali metal salt and/or complex of the injection layer; and/or (iii) a rare earth metal and an alkali halide, preferably Yb and KI.

The electron injection layer may include at least one selected from LiF, NaCl, CsF, $Li_2O$, and BaO.

A thickness of the EIL may be from about 0.1 nm to about 10 nm, or about 0.3 nm to about 9 nm. When the thickness of the electron injection layer is within these ranges, the electron injection layer may have satisfactory electron injection ability without a substantial increase in operating voltage.

Cathode

A material for the cathode may be a metal, an alloy, or an electrically conductive compound that have a low work function, or a combination thereof. Specific examples of the material for the cathode may be lithium (Li), magnesium (Mg), aluminum (Al), aluminum-lithium (Al—Li), calcium (Ca), magnesium-indium (Mg—In), magnesium-silver (Mg—Ag), etc. In order to manufacture a top-emission light-emitting device having a reflective anode deposited on a substrate, the cathode may be formed as a light-transmissive electrode from, for example, indium tin oxide (ITO) or indium zinc oxide (IZO).

In devices comprising a transparent metal oxide cathode or a reflective metal cathode, the cathode may have a thickness from about 50 nm to about 100 nm, whereas semitransparent metal cathodes may be as thin as from about 5 nm to about 15 nm.

Organic Electronic Device

An organic electronic device according to the invention may include a substrate, an anode layer, an organic semiconductor layer comprising a compound of formula 1 or 4 and a cathode layer.

An organic light-emitting diode (OLED) according to the invention may include an anode, a hole transport layer (HTL), an emission layer (EML), a first electron transport layer (ETL) comprising at least one compound of formula 1 or 4, and a cathode, which are sequentially stacked on a substrate. In this regard, the HTL, the EML, and the ETL are thin films formed from organic compounds.

According to one embodiment the OLED may have the following layer structure, wherein the layers having the following order:
an anode layer, a hole injection layer, optional an first hole transport layer, optional a second hole transport layer, an emission layer, an electron transport layer comprising a compound of formula 1 or 4 according to the invention, an electron injection layer, and a cathode layer.

According to another aspect of the present invention, there is provided a method of manufacturing an organic electronic device, the method using:
- at least one deposition source, preferably two deposition sources and more preferred at least three deposition sources.

The methods for deposition that can be suitable comprise:
deposition via vacuum thermal evaporation;
deposition via solution processing, preferably the processing is selected from spin-coating, printing, casting; and/or
slot-die coating.

According to various embodiments of the present invention, there is provided a method using:
- a first deposition source to release the compound of formula 1 or 4 according to the invention, and
- a second deposition source to release the alkali halide or alkali organic complex, preferably a lithium halide or lithium organic complex;

the method comprising the steps of forming the electron transport layer stack; whereby for an organic light-emitting diode (OLED):
the first electron transport layer is formed by releasing the compound of formula 1 or 4 according to the invention from the first deposition source and the alkali halide or alkali organic complex, preferably a lithium halide or lithium organic complex from the second deposition source.

According to various embodiments of the present invention, the method may further include forming on the anode electrode an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
on a substrate a first anode electrode is formed,
on the first anode electrode an emission layer is formed,
on the emission layer an electron transport layer stack is formed, preferably the first electron transport layer is formed on the emission layer and optional a second electron transport layer is formed,
and finally a cathode electrode is formed, optional a hole injection layer, a hole transport layer, and a hole blocking layer, formed in that order between the first anode electrode and the emission layer,
optional an electron injection layer is formed between the electron transport layer and the cathode electrode.

According to various embodiments of the present invention, the method may further include forming an electron injection layer on the first electron transport layer.

According to another embodiment, a process of preparing an organic electronic device, wherein the electron injection layer is formed by
(i) a step of transferring into the gas phase a metal composition comprising a first metal selected from an alkali metal and a second metal selected from Mg, Zn, Hg, Cd and Te and a step of depositing the alkali metal on the at least one organic semiconductor layer; or
(ii) a step of transferring into the gas phase a rare earth metal and an alkali metal halide and a step of depositing the rare earth metal and alkali halide on the at least one organic semiconductor layer.

However, according to various embodiments of the OLED of the present invention, the OLED may not comprise an electron injection layer.

According to various embodiments, the OLED may have the following layer structure, wherein the layers having the following order:
an anode, first hole transport layer, second hole transport layer, emission layer, optional second electron transport layer, first electron transport layer comprising a compound of formula 1 or 4 according to the invention, optional an electron injection layer, and a cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

Hereinafter, the embodiments are illustrated in more detail with reference to examples. However, the present disclosure is not limited to the following examples.

DESCRIPTION OF THE DRAWINGS

These and/or other aspects and advantages of the present invention will become apparent and more readily appreciated from the following description of the exemplary embodiments, taken in conjunction with the accompanying drawings, of which.

Figure 1:
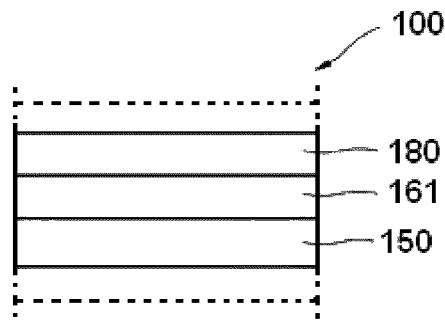
FIG. 1 is a schematic sectional view of an organic light-emitting diode (OLED), according to an exemplary embodiment of the present invention with an emission layer, one electron transport layer and an electron injection layer.

Reference will now be made in detail to the exemplary aspects, examples of which are illustrated in the accompanying drawings, wherein like reference numerals refer to the like elements throughout. The exemplary embodiments are described below, in order to explain the aspects, by referring to the figures.

Herein, when a first element is referred to as being formed or disposed "on" a second element, the first element can be disposed directly on the second element, or one or more other elements may be disposed there between. When a first element is referred to as being formed or disposed "directly on" a second element, no other elements are disposed there between.

The term "contacting sandwiched" refers to an arrangement of three layers whereby the layer in the middle is in direct contact with the two adjacent layers.

The organic light emitting diodes according to an embodiment of the present invention may include a hole transport region; an emission layer; and a first electron transport layer comprising a compound according to formula 1 or 4.

FIG. 1 is a schematic sectional view of an organic light-emitting diode 100, according to an exemplary embodiment of the present invention. The OLED 100 comprises an emission layer 150, an electron transport layer (ETL) 161 and an electron injection layer 180, whereby the first electron transport layer 161 is disposed directly on the emission layer 150 and the electron injection layer 180 is disposed directly on the first electron transport layer 161.

Figure 2:
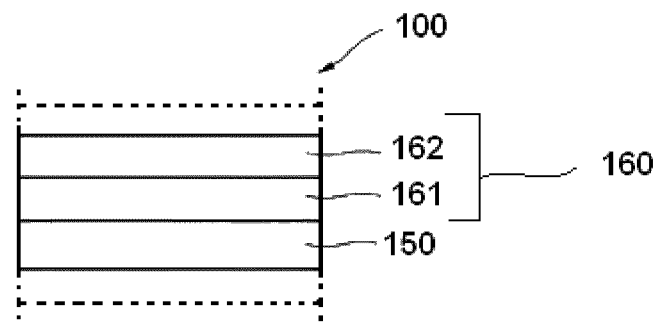
FIG. 2 is a schematic sectional view of an organic light-emitting diode (OLED), according to an exemplary embodiment of the present invention with an emission layer and two electron transport layers.

FIG. 2 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161 and a second electron transport layer 162, whereby the second electron transport layer 162 is disposed directly on the first electron transport layer 161.

Figure 3:
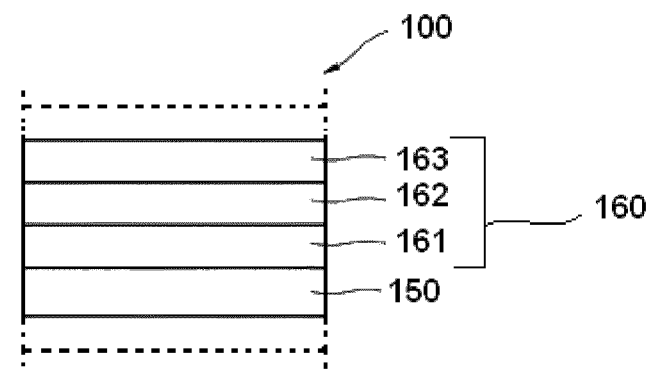
FIG. 3 is a schematic sectional view of an OLED, according to an exemplary embodiment of the present invention with an emission layer and three electron transport layers.

FIG. 3 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161, a second electron transport layer 162, and a third electron transport layer 163, whereby the second electron transport layer 162 is disposed directly on the first electron transport layer 161 and the third electron transport layer 163 is disposed directly on the second electron transport layer 162.

Figure 4:
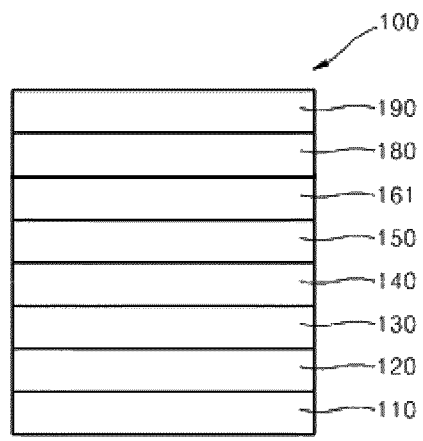
FIG. 4 is a schematic sectional view of an organic light-emitting diode (OLED), according to an exemplary embodiment of the present invention with an emission layer and one electron transport layer.

FIG. 4 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, one first electron transport layer (ETL) 161, an electron injection layer (EIL) 180, and a cathode electrode 190. The first electron transport layer (ETL) 161 comprises a compound of formula 1 or 4 and optionally an alkali halide or alkali organic complex. The electron transport layer (ETL) 161 is formed directly on the EML 150.

Figure 5:
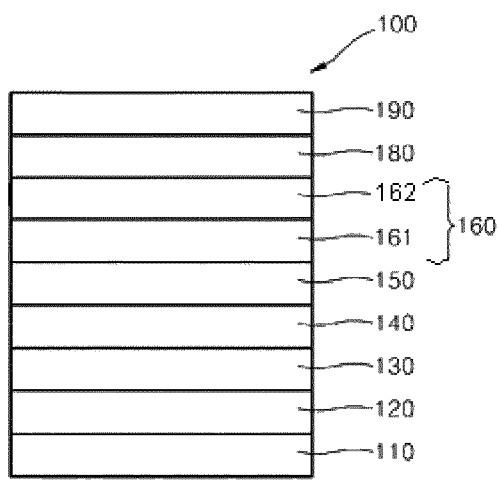
FIG. 5 is a schematic sectional view of an organic light-emitting diode (OLED), according to an exemplary embodiment of the present invention with an emission layer and two electron transport layers.

FIG. 5 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a cathode electrode 190. The electron transport layer (ETL) 160 comprises a first electron transport layer 161 and a second electron transport layer 162, wherein the first electron transport layer is arranged near to the anode (120) and the second electron transport layer is arranged near to the cathode (190). The first and/or the second electron transport layer comprise a compound of formula 1 or 4 and optionally an alkali halide or alkali organic complex.

Figure 6:
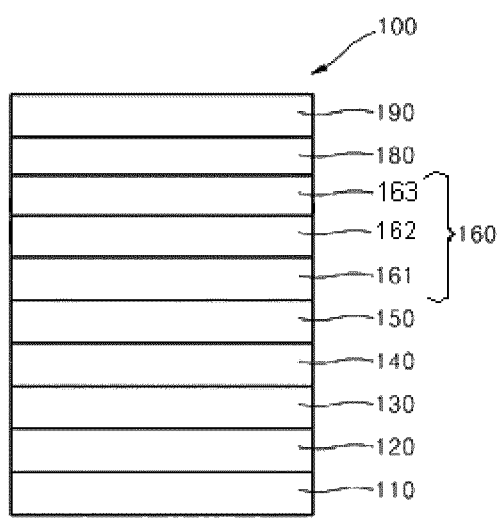
FIG. 6 is a schematic sectional view of an OLED, according to an exemplary embodiment of the present invention with an emission layer and three electron transport layers.

FIG. 6 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a second cathode electrode 190. The electron transport layer stack (ETL) 160 comprises a first electron transport layer 161, a second electron transport layer 162 and a third electron transport layer 163. The first electron transport layer 161 is formed directly on the emission layer (EML) 150. The first, second and/or third electron transport layer comprise a compound of formula 1 or 4 and optionally an alkali halide or alkali organic complex.

A substrate may be further disposed under the anode 120 or on the cathode 190. The substrate may be a substrate that is used in a general organic light emitting diode and may be a glass substrate or a transparent plastic substrate with strong mechanical strength, thermal stability, transparency, surface smoothness, ease of handling, and water resistance.

The hole injection layer 130 may improve interface properties between ITO as an anode and an organic material used for the hole transport layer 140, and may be applied on a non-planarized ITO and thus may planarize the surface of the ITO. For example, the hole injection layer 130 may include a material having particularly desirable conductivity between a work function of ITO and HOMO of the hole transport layer 140, in order to adjust a difference a work function of ITO as an anode and HOMO of the hole transport layer 140.

When the hole transport region comprises a hole injection layer 130, the hole injection layer may be formed on the anode 120 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-8}$ torr to about $10^{-3}$ torr, and a deposition rate of about 0.01 to about 100 Å/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

A thickness of the hole transport region may be from about 100 Å to about 10000 Å, for example, about 100 Å to about 1000 Å. When the hole transport region comprises the hole injection layer and the hole transport layer, a thickness of the hole injection layer may be from about 100 Å to about 10,000 Å, for example about 100 Å to about 1000 Å and a thickness of the hole transport layer may be from about 50 Å to about 2,000 Å, for example about 100 Å to about 1500 Å. When the thicknesses of the hole transport region, the HIL, and the HTL are within these ranges, satisfactory hole transport characteristics may be obtained without a substantial increase in operating voltage.

A thickness of the emission layer may be about 100 Å to about 1000 Å, for example about 200 Å to about 600 Å. When the thickness of the emission layer is within these ranges, the emission layer may have improved emission characteristics without a substantial increase in operating voltage.

Next, an electron transport region is disposed on the emission layer.

The electron transport region may include at least one of a second electron transport layer, a first electron transport layer, and an electron injection layer.

The thickness of the electron transport layer may be from about 20 Å to about 1000 Å, for example about 30 Å to about 300 Å. When the thickness of the electron transport layer is within these ranges, the electron transport layer may have improved electron transport auxiliary ability without a substantial increase in operating voltage.

A thickness of the electron transport layer may be about 100 Å to about 1000 Å, for example about 150 Å to about 500 Å. When the thickness of the electron transport layer is within these ranges, the electron transport layer may have satisfactory electron transporting ability without a substantial increase in operating voltage.

In addition, the electron transport region may include an electron injection layer (EIL) that may facilitate injection of electrons from the anode.

The electron injection layer is disposed on an electron transport layer and may play a role of facilitating an electron injection from a cathode and ultimately improving power efficiency and be formed by using any material used in a related art without a particular limit, for example, LiF, Liq, NaCl, CsF, Li$_2$O, BaO, Yb and the like.

The electron injection layer may include at least one selected from LiF, NaCl, CsF, Li$_2$O, and BaO.

A thickness of the EIL may be from about 1 Å to about 100 Å, or about 3 Å to about 90 Å. When the thickness of the electron injection layer is within these ranges, the electron injection layer may have satisfactory electron injection ability without a substantial increase in operating voltage.

The anode can be disposed on the organic layer. A material for the anode may be a metal, an alloy, or an electrically conductive compound that have a low work function, or a combination thereof. Specific examples of the material for the anode 150 may be lithium (Li, magnesium (Mg), aluminum (Al), aluminum-lithium (Al-LI, calcium (Ca), magnesium-indium (Mg—In), magnesium-silver (Mg—Ag), etc. In order to manufacture a top-emission light-emitting device, the anode 150 may be formed as a light-transmissive electrode from, for example, indium tin oxide ITO) or indium zinc oxide IZO).

According to another aspect of the invention, a method of manufacturing an organic electroluminescent device is provided, wherein
   on an anode electrode (120) the other layers of hole injection layer (130), hole transport layer (140), optional an electron blocking layer, an emission layer (130), first electron transport layer (161), second electron transport layer (162), electron injection layer (180), and a cathode (190), are deposited in that order; or
   the layers are deposited the other way around, starting with the cathode (190).

Hereinafter, the embodiments are illustrated in more detail with reference to examples.

However, the present disclosure is not limited to the following examples.

Preparation of Compounds of Formula 1

Compound of formula 1 may be prepared as described below.

Synthesis of Dialkylphosphine Oxide

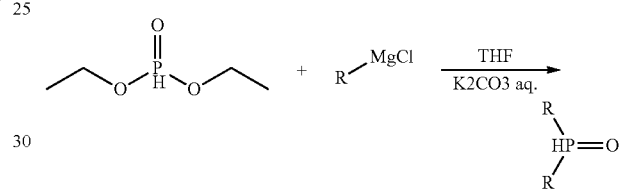

Dialkyphosphine oxides were prepared using a known procedure (Hays, R. H., *The Journal of Organic Chemistry* 1968 33 (10), 3690-3694)

Diethyl phosphonate (0.95 eq) is added to an ice cooled Grignard solution in THF (3 eq.) at such a rate that a temperature of the reaction mixture is maintained at 20-30° C. After stirring at room temperature for 1 h the mixture is hydrolyzed by mixing it with an ice-cold saturated aqueous solution of potassium carbonate (3 eq.). Precipitated magnesium carbonate is removed by filtration and washed several time with ethanol. Combined filtrates are concentrated in vacuum to give a crude material, which could be further purified by distillation or re-crystallization from an appropriate solvent.

TABLE 1

Following compounds could be prepared using this procedure

| Starting compound | Product | Yield/MS data |
|---|---|---|
| Methylmagnesium chloride | Dimethylphosphine oxide | 70.8%/78[M]$^+$ |

Standard Procedure for Coupling of Dialkylphosphine Oxide with Arylhalides

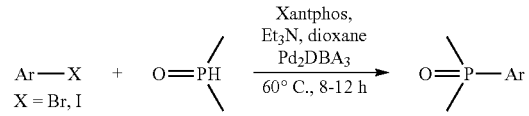

Schleck flask is charged with arylhalide (1 eq), dialkylphoshine oxide (1 eq. per halide atom) and sealed with a rubber septum. Atmosphere is replaced by Argon and the starting compounds are dissolved in anhydrous dioxane or suspended in dioxane-THF mixture (1:1 vol.) In a separate vial, a mixture of tris(dibenzylideneacetone)dipalladium (0.5 mol %), Xantphos (1 mol %) and triethylamine (1.17 eq per halide atom) is dissolved in anhydrous dioxane (75 ml/mmol) at 24° C. for 10 min. This catalyst solution is added to the mixture of phosphine oxide and aryl halide and the reaction mixture was stirred for 8-24 h at 60° C.

Work Up Procedure 1: A precipitated solid (trimethylamine salt) is separated by filtration through sintered glass filter (Pore size 4), washed two times with dioxane, combined filtrates are evaporated to a dryness under reduced pressure using a rotary evaporator. The residue is dissolved in water, pH is set to alkaline (~14) using aqueous potassium hydroxide solution. Resulting yellow turbid aqueous layer is sequentially extracted with hexane and diethyl ether. Combined organic layers are extracted with ~0.5M aqueous KOH solution, aqueous phases are combined, acidified by hydrochloric acid and extracted with dichloromethane. Combined extracts are washed with saturated sodium hydrocarbonate solution, brine and dried over magnesium sulfate. Solvent is removed under reduced pressure, residue is triturated with hexane, white crystalline precipitate is collected by vacuum filtration, washed with hexane and dried.

Work Up Procedure 2: Reaction mixture is diluted with water, precipitated material is collected by suction using a sintered glass filter (pore 4), washed with water, methanol and dried. Crude product could be further purified by re-crystallization or trituration with appropriate solvents. Final purification is achieved by sublimation in a high vacuum.

TABLE 2

| Following compounds could be prepared using this procedure | | |
|---|---|---|
| Starting compound(s) | Product/(work-up procedure) | Yield/MS data |
| 1-bromo-4-iodobenzene, dimethylphosphine oxide | (4-bromophenyl)dimethylphosphine oxide/ (1) | 75%/232 [M]+ |
| 1-bromo-3-iodobenzene, dimethylphosphine oxide | (3-bromophenyl)dimethylphosphine oxide/ (1) | 70.8%/232 [M]+ |

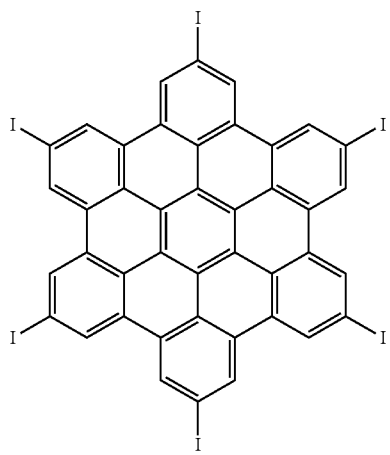 [SMILES: Ic1cc2c3cc(I)cc4c5cc(I)cc6c7cc(I)cc8c9cc(I)cc%10c%11cc(I)cc%12c(c1)c2c1c(c34)c(c56)c(c78)c(c%109)c1c%12%11] 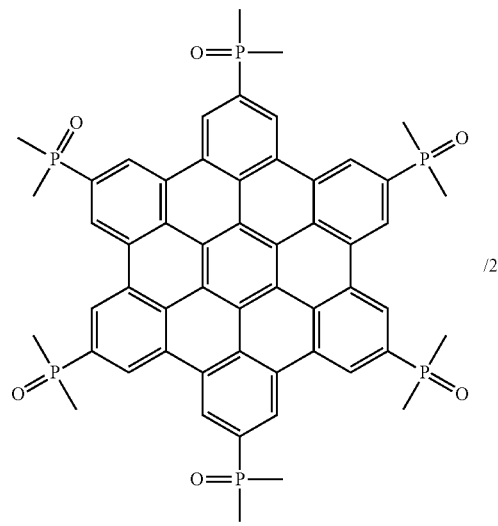 [SMILES: CP(C)(=O)c1cc2c3cc(P(C)(C)=O)cc4c5cc(P(C)(C)=O)cc6c7cc(P(C)(C)=O)cc8c9cc(P(C)(C)=O)cc%10c%11cc(P(C)(C)=O)cc%12c(c1)c2c1c(c34)c(c56)c(c78)c(c%109)c1c%12%11]

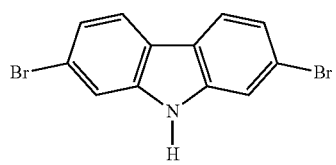 [SMILES: Brc1ccc2c(c1)[nH]c1cc(Br)ccc12] 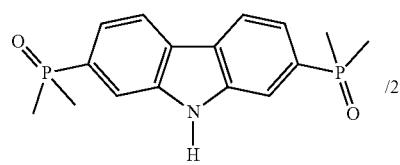 [SMILES: CP(C)(=O)c1ccc2c(c1)[nH]c1cc(P(C)(C)=O)ccc12]

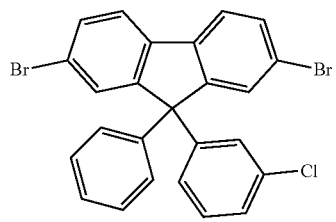 [SMILES: Clc1cccc(C2(c3ccccc3)c3cc(Br)ccc3-c3ccc(Br)cc32)c1] 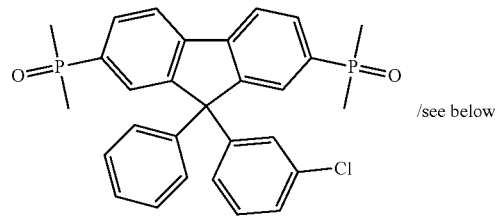 [SMILES: CP(C)(=O)c1ccc2c(c1)C(c1ccccc1)(c1cccc(Cl)c1)c1cc(P(C)(C)=O)ccc1-2]

/see below

TABLE 2-continued

| Starting compound(s) | Product/(work-up procedure) | Yield/MS data |
|---|---|---|
| 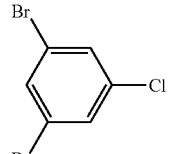 | 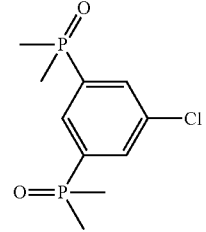 | |

Standard Procedure for the Synthesis of Boronic Ester

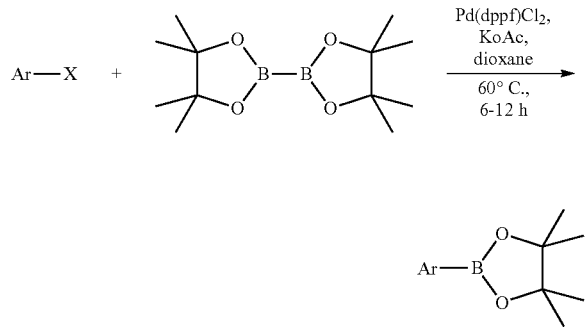

Schleck flask is charged with arylhalide (1 eq), 4,4,4',4',5,5,5',5'-octamethyl-2,2'-bi(1,3,2-dioxaborolane) (1.3 eq. per halide atom), potassium acetate (3 eq) and [1,1'-Bis(diphenylphosphino)ferrocene]dichloropalladium(II) (Pd(dffp)Cl$_2$, 0.03 eq) and sealed with a rubber septum. Atmosphere is replaced by Argon and anhydrous dioxane is added via double tipped cannula. The mixture is stirred at 60° C. for 6-48 h, the progress of the reaction is monitored by TLC.

Work-Up Procedure 1: All volatiles are removed under reduced pressure, residue is triturated with toluene, insoluble anorganic salts are removed by filtration, filtrate is evaporated to dryness and triturated with methyl-tert.-butyl ether. Pale-brown crystalline precipitate is collected by vacuum filtration, washed with hexane and dried.

Work-Up Procedure 2: Precipitate is collected by suction filtration, washed with water, methanol and dried in vacuum at 40° C. yielding the crude product, which is then purified by column chromatography or re-crystallization or trituration with an appropriate solvent.

TABLE 3

| Starting compound(s) | Product/(work-up procedure) | Yield/MS data |
|---|---|---|
| 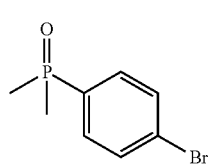 | 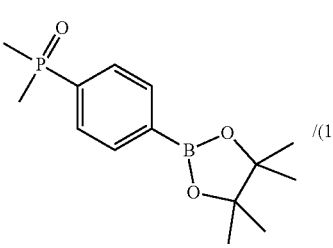 /(1) | 57%/280 [M]$^+$ |
| 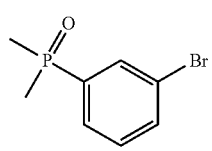 | 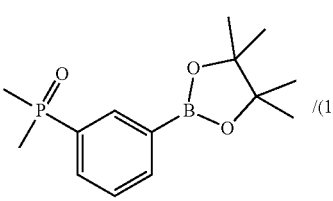 /(1) | 69%/280 [M]$^+$ |

TABLE 3-continued

Following compounds could be prepared using this procedure

| Starting compound(s) | Product/(work-up procedure) | Yield/MS data |
|---|---|---|
| [structure: 9-(3-bromophenyl)-2,7-bis(dimethylphosphoryl)carbazole] | [structure: 9-(3-(4,4,5,5-tetramethyl-1,3,2-dioxaborolan-2-yl)phenyl)-2,7-bis(dimethylphosphoryl)carbazole] /(2) |  |
| [structure: 2,7-bis(dimethylphosphoryl)-9-(3-chlorophenyl)-9-phenylfluorene] | [structure: 2,7-bis(dimethylphosphoryl)-9-phenyl-9-(3-(pinacolboryl)phenyl)fluorene] /(2) |  |
| [structure: 9-(3-bromophenyl)-3,6-bis(dimethylphosphoryl)carbazole] | [structure: 9-(3-(pinacolboryl)phenyl)-3,6-bis(dimethylphosphoryl)carbazole] |  |
| [structure: 1-chloro-3,5-bis(dimethylphosphoryl)benzene] | [structure: 3,5-bis(dimethylphosphoryl)phenylboronic acid pinacol ester] |  |

TABLE 3-continued

Following compounds could be prepared using this procedure

| Starting compound(s) | Product/(work-up procedure) | Yield/MS data |
|---|---|---|
| 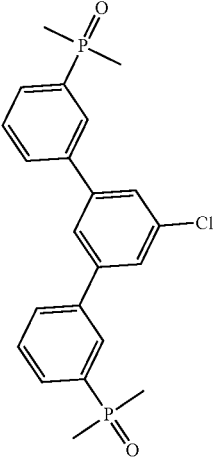 [SMILES: CP(C)(=O)c1cccc(-c2cc(Cl)cc(-c3cccc(P(C)(C)=O)c3)c2)c1] | 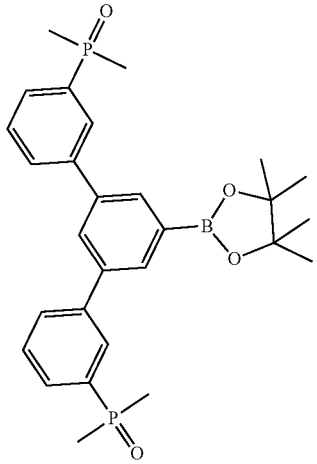 [SMILES: CC1(C)OB(c2cc(-c3cccc(P(C)(C)=O)c3)cc(-c3cccc(P(C)(C)=O)c3)c2)OC1(C)C] | |

Standard Procedures for Suzuki-Miyaura Coupling

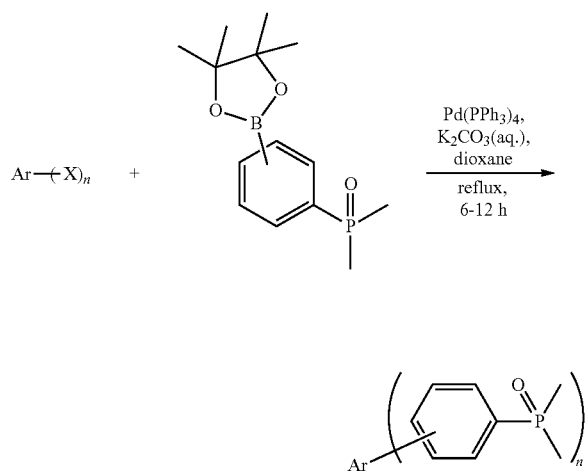

A three neck round bottom flask, equipped with dropping funnel, reflux condenser and magnetic stir bar is charged with an arylhalide (1 eq) and corresponding boronic ester or acid (1.25 eq. per halogen atom in arylhalide), the flask is sealed with a rubber septum, evacuated and back-filled with argon (2 times). Anhydrous dioxane (4 ml/mmol of arylhalide) is added through the septum using a double-tipped needle. Separately, a solution of potassium carbonate (2M in water) is prepared and degassed with N2 for 30 min. The solution is added to the reaction mixture through the septum using a double-tipped needle, followed by the addition of the tetrakis(triphenylphosphin)palladium(0) (3 mol %) under a positive nitrogen pressure. Nitrogen purged reflux condenser is attached to the flask and the reaction mixture is stirred at 90° C. for 12 h. The mixture is allowed to cool down to the room temperature, a precipitate is collected by filtration, washed with water, methanol, dried in vacuum at 40° C. to give a crude product, which is further purified by recrystallization or trituration with appropriate solvents. Final purification is achieved by sublimation in a high vacuum.

TABLE 4

Following compounds could be prepared using this procedure

| Starting compound | Product | Yield/MS data |
|---|---|---|
| 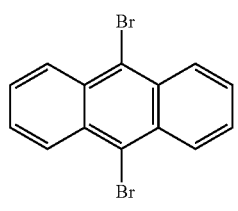 [SMILES: Brc1c2ccccc2c(Br)c2ccccc12] | 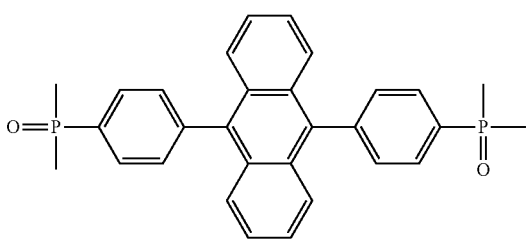 [SMILES: CP(C)(=O)c1ccc(-c2c3ccccc3c(-c3ccc(P(C)(C)=O)cc3)c3ccccc23)cc1] | 60.2%/482[M]+ |

TABLE 4-continued
Following compounds could be prepared using this procedure
| Starting compound | Product | Yield/MS data |
|---|---|---|
| 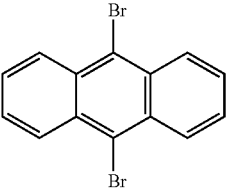 [SMILES: Brc1c2ccccc2c(Br)c2ccccc12] | 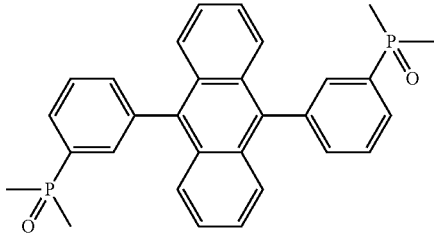 | 73.3%/ 482[M]+ |
| 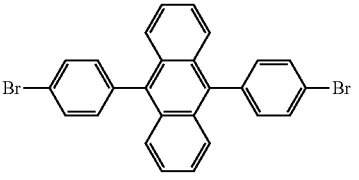 [SMILES: Brc1ccc(-c2c3ccccc3c(-c3ccc(Br)cc3)c3ccccc23)cc1] | 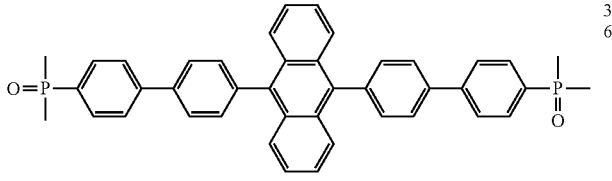 | 39.6%/ 634[M]+ |
| 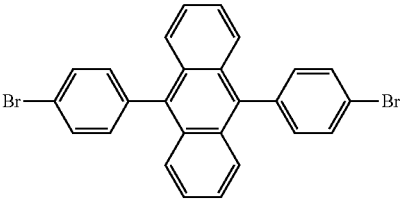 [SMILES: Brc1ccc(-c2c3ccccc3c(-c3ccc(Br)cc3)c3ccccc23)cc1] | 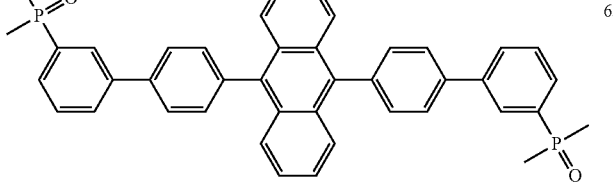 | 57.7%/ 634[M]+ |
| 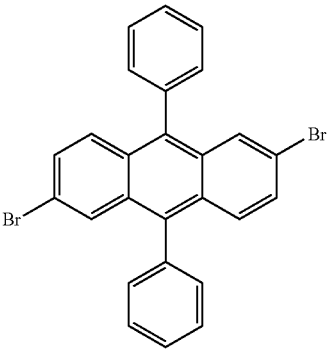 [SMILES: Brc1ccc2c(-c3ccccc3)c3cc(Br)ccc3c(-c3ccccc3)c2c1] | 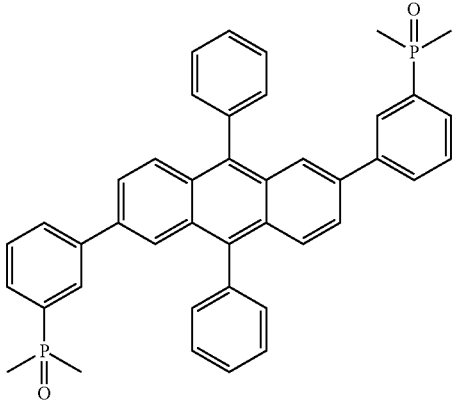 [SMILES: CP(C)(=O)c1cccc(-c2ccc3c(-c4ccccc4)c4cc(-c5cccc(P(C)(C)=O)c5)ccc4c(-c4ccccc4)c3c2)c1] | |
| 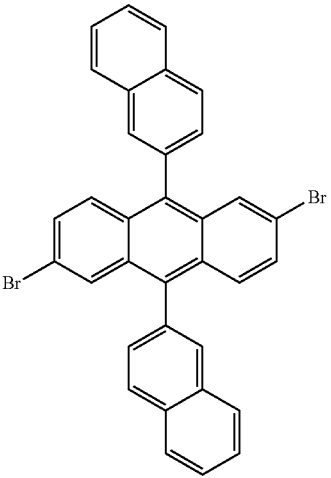 [SMILES: Brc1ccc2c(-c3ccc4ccccc4c3)c3cc(Br)ccc3c(-c3ccc4ccccc4c3)c2c1] | 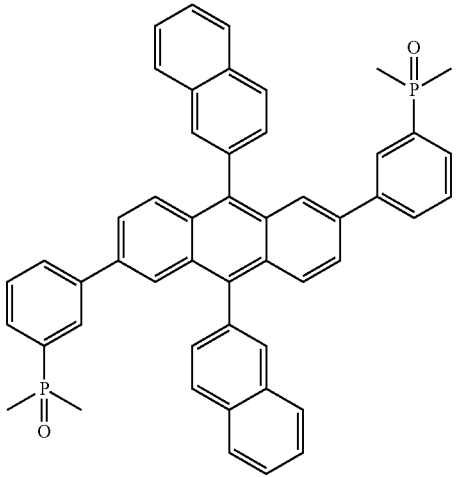 [SMILES: CP(C)(=O)c1cccc(-c2ccc3c(-c4ccc5ccccc5c4)c4cc(-c5cccc(P(C)(C)=O)c5)ccc4c(-c4ccc5ccccc5c4)c3c2)c1] | |

TABLE 4-continued

Following compounds could be prepared using this procedure

| Starting compound | Product | Yield/MS data |
|---|---|---|

TABLE 4-continued
Following compounds could be prepared using this procedure
| Starting compound | Product | Yield/MS data |
|---|---|---|
| 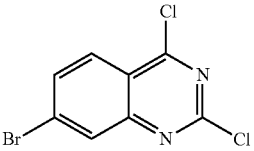 | 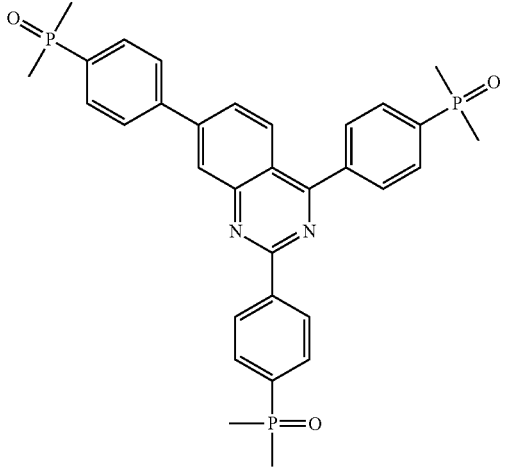 [SMILES: CP(C)(=O)c1ccc(-c2ccc3c(-c4ccc(P(C)(C)=O)cc4)nc(-c4ccc(P(C)(C)=O)cc4)nc3c2)cc1] | |
| 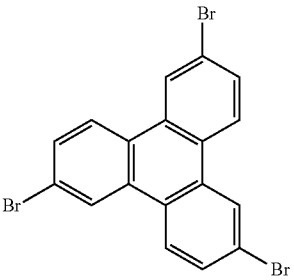 [SMILES: Brc1ccc2c(c1)c1ccc(Br)cc1c1ccc(Br)cc21] | 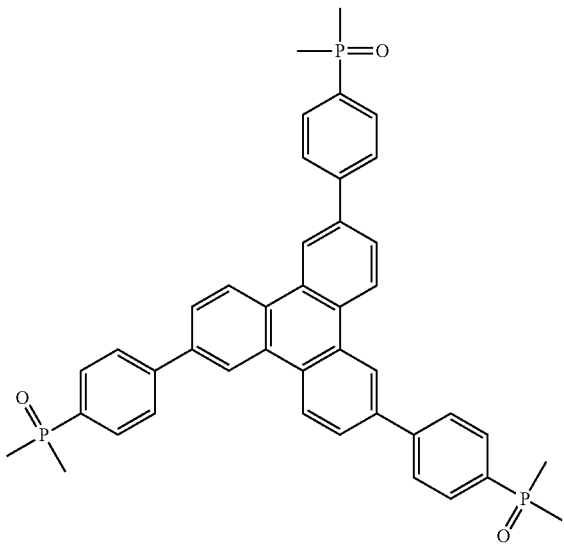 | |
| 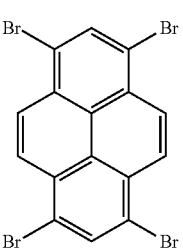 | 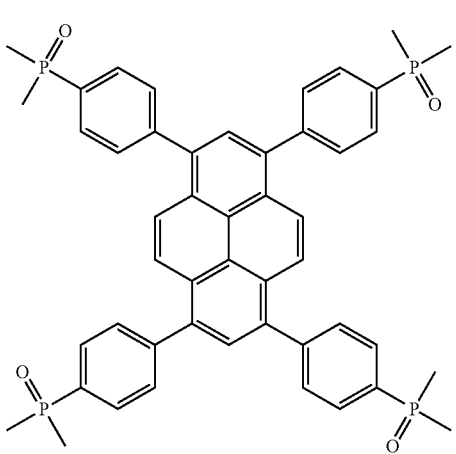 | |

TABLE 4-continued

Following compounds could be prepared using this procedure

| Starting compound | Product | Yield/MS data |
|---|---|---|

TABLE 4-continued

Following compounds could be prepared using this procedure

| Starting compound | Product | Yield/MS data |
|---|---|---|

TABLE 4-continued
Following compounds could be prepared using this procedure
| Starting compound | Product | Yield/MS data |
|---|---|---|
| 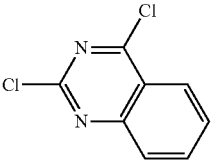 | 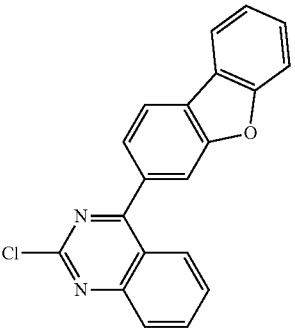 [SMILES: Clc1nc(-c2ccc3c(c2)oc2ccccc23)c2ccccc2n1] | |
| 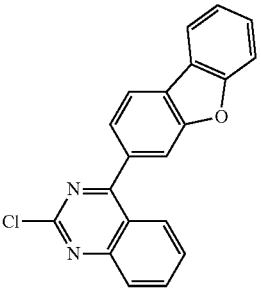 [SMILES: Clc1nc(-c2ccc3c(c2)oc2ccccc23)c2ccccc2n1] | 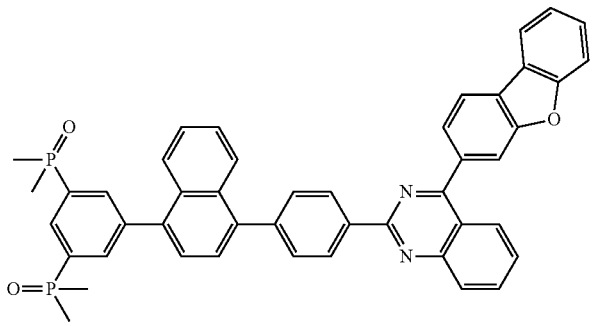 [SMILES: CP(C)(=O)c1cc(-c2ccc(-c3ccc(-c4nc(-c5ccc6c(c5)oc5ccccc56)c5ccccc5n4)cc3)c3ccccc23)cc(P(C)(C)=O)c1] | |
| 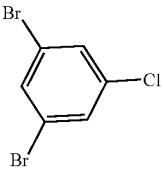 | 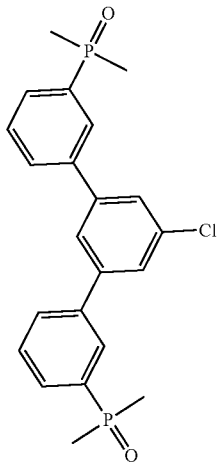 [SMILES: CP(C)(=O)c1cccc(-c2cc(Cl)cc(-c3cccc(P(C)(C)=O)c3)c2)c1] | |

TABLE 4-continued
Following compounds could be prepared using this procedure
| Starting compound | Product | Yield/MS data |
|---|---|---|
Synthesis of ((6-(3'-(diphenylphosphoryl)-[1,1'-biphenyl]-3-yl)-1,3,5-triazine-2,4-diyl)bis([1,1'-biphenyl]-3',3-diyl))bis(dimethylphosphine oxide)
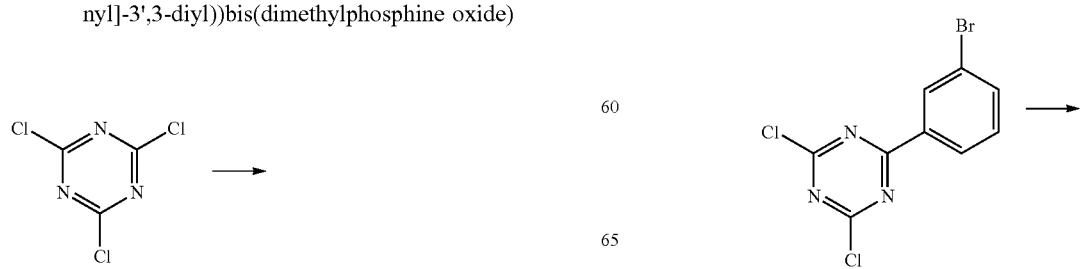

-continued

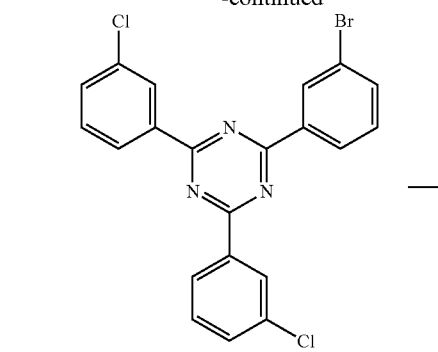

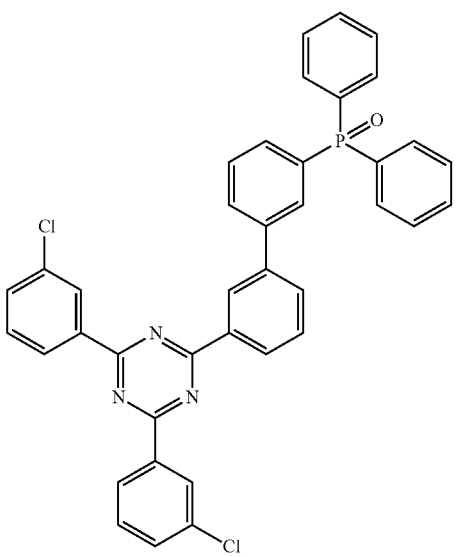

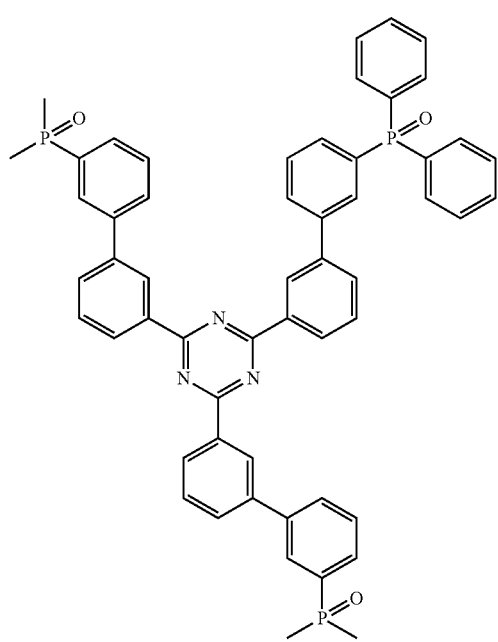 [SMILES: CP(C)(=O)c1cccc(-c2cccc(-c3nc(-c4cccc(-c5cccc(P(C)(C)=O)c5)c4)nc(-c4cccc(-c5cccc(P(=O)(c6ccccc6)c6ccccc6)c5)c4)n3)c2)c1]

Step1:
2-(3-bromophenyl)-4,6-dichloro-1,3,5-triazine

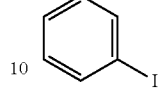

1. Mg, Br—CH$_2$—CH$_2$—Br, Et$_2$O
2. Cyanuric chloride, THF, 0° C.->RT

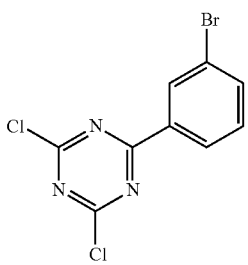

A 3-necked, 250 mL round bottom flask equipped with a magnetic stirrer, septum, nitrogen inlet, and addition funnel, is charged with magnesium turnings (1.2 g, 0.049 mol). The flask is sealed and the atmosphere is replaced by nitrogen. Anhydrous diethyl ether (50 mL) is added, followed by an addition of 1,2 dibromoethane (0.187 g, 1 mmol). The mixture is stirred at RT until the evolution of ethylene is stopped. The addition funnel is charged with 1,4-dibromobenzene (11.4 g, 0.048 mol),dissolved in 50 mL of anhydrous. The solution is added to the reaction mixture at the rate to maintain a gentle reflux. Ones the addition is complete, the mixture is allowed to reflux for additional 30 minutes, A 3-necked, 250 mL round bottom flask equipped with a magnetic stirrer, thermocouple, nitrogen inlet, and a septum is charged with cyanuric chloride (0.048 mol, 8.85 g). The atmosphere is replaced by nitrogen, an anhydrous THF (50 ml) is added, and the solution is cooled to −20° C. Grignard solution is added through the septum using double tipped needle with a rate to maintain the reaction temperature below −15° C. The reaction is stirred for 1 hour and warmed to 0° C. whereupon it is quenched with cold saturated ammonium chloride and partitioned between ethyl acetate and dilute sodium chloride solution. The organic layer is separated, dried over magnesium sulfate, filtered and evaporated to yield crude product that could be used directly, without further purification, in subsequent reactions.

Step2: 2-(3-bromophenyl)-4,6-bis(3-chlorophenyl)-1,3,5-triazine

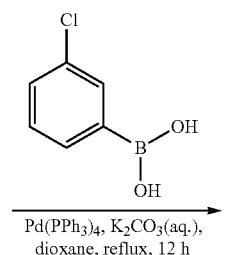

Pd(PPh$_3$)$_4$, K$_2$CO$_3$(aq.),
dioxane, reflux, 12 h

-continued

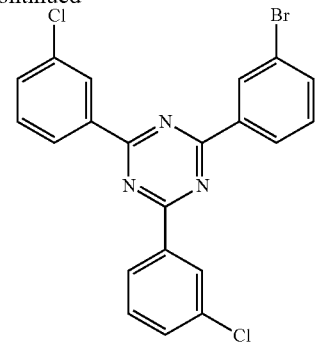

The title compound is prepared from 2-(3-bromophenyl)-4,6-dichloro-1,3,5-triazine (10 g, 0.033 mol) and (3-chlorophenyl)boronic acid (2.2 eq, 11.35 g) using standard protocol for Suzuki-Miyaura coupling, described above. A crude product is purified by recrystallization from DFM.

Step3: (3'-(4,6-bis(3-chlorophenyl)-1,3,5-triazin-2-yl)-[1,1'-biphenyl]-3-yl)diphenylphosphine oxide

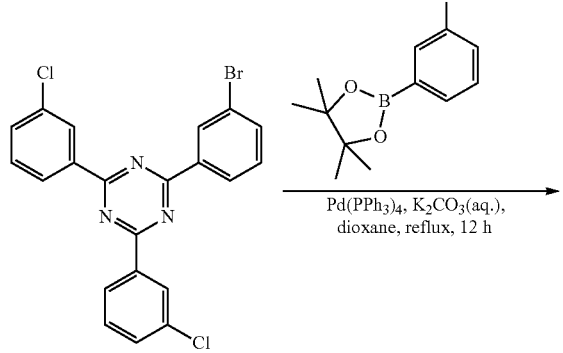

The title compound is prepared from 2-(3-bromophenyl)-4,6-bis(3-chlorophenyl)-1,3,5-triazine (10 g, 0.022 mol) and diphenyl(3-(4,4,5,5-tetramethyl-1,3,2-dioxaborolan-2-yl)phenyl)phosphine oxide (1 eq, 8.84 g) using standard protocol for Suzuki-Miyaura coupling, described above.

Step4: ((6-(3'-(diphenylphosphoryl)-[1,1'-biphenyl]-3-yl)-1,3,5-triazine-2,4-diyl)bis([1,1'-biphenyl]-3',3-diyl))bis(dimethylphosphine oxide)

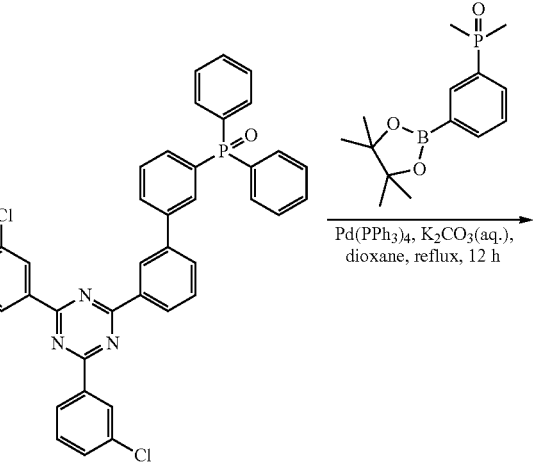

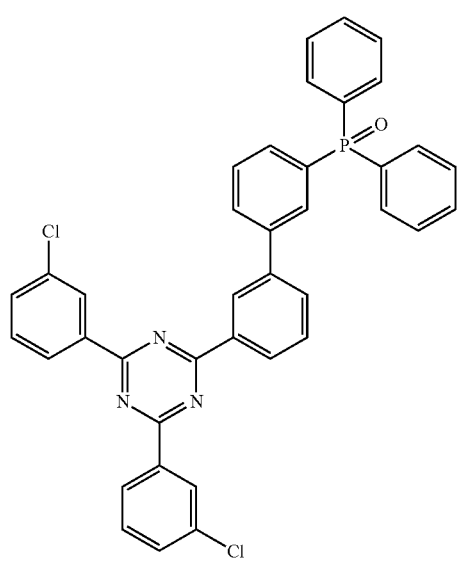

The title compound is prepared from (3'-(4,6-bis(3-chlorophenyl)-1,3,5-triazin-2-yl)-[1,1'-biphenyl]-3-yl)diphenylphosphine oxide (10 g, 0.015 mol) and dimethyl(3-(4,4,5,5-tetramethyl-1,3,2-dioxaborolan-2-yl)phenyl)phosphine oxide (2.2 eq, 9.24 g) using standard protocol for Suzuki-Miyaura coupling, described above.

81

Synthesis of (9-(3-(4,6-diphenyl-1,3,5-triazin-2-yl) phenyl)-9H-carbazole-2,7-diyl)bis(dimethylphosphine oxide)

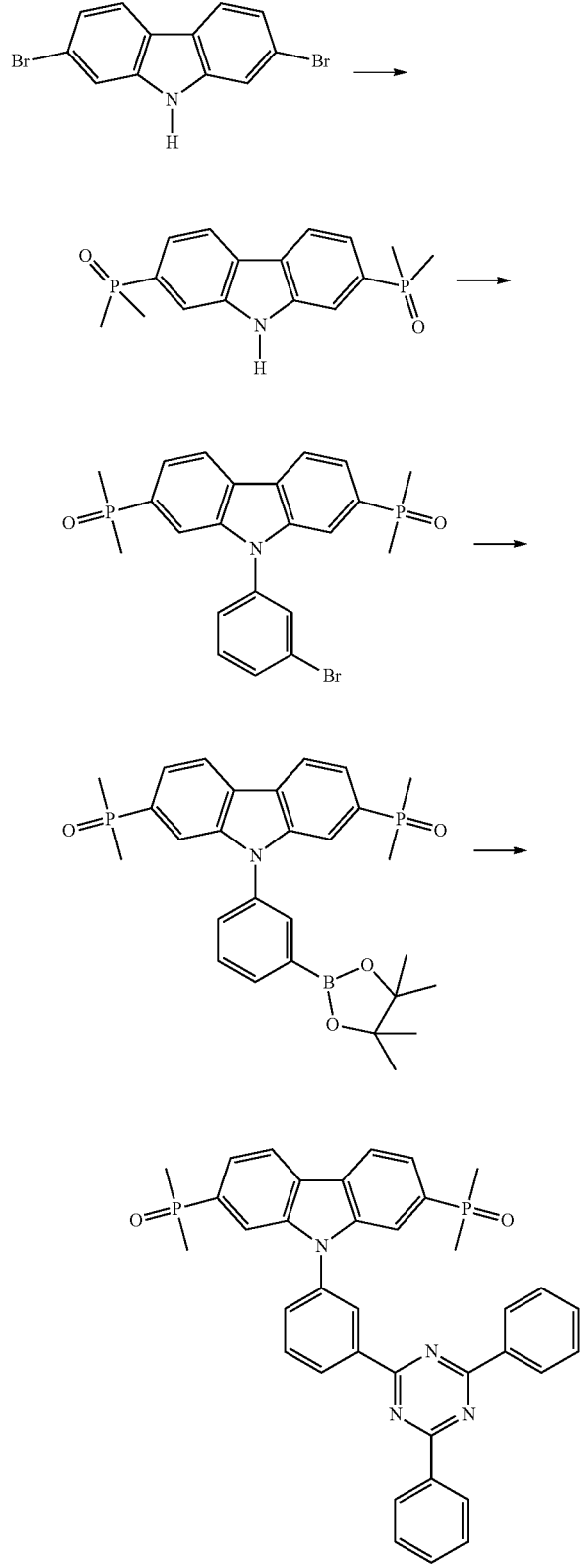

82

Step1: (9H-carbazole-2,7-diyl)bis(dimethylphosphine oxide)

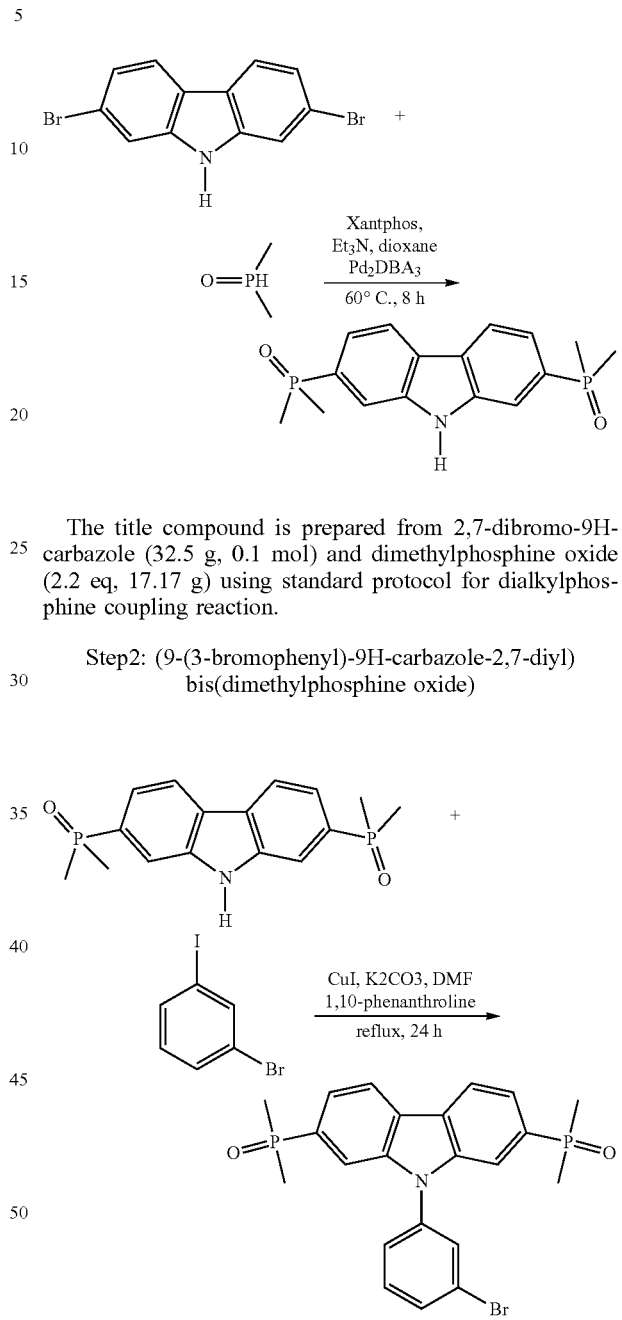

The title compound is prepared from 2,7-dibromo-9H-carbazole (32.5 g, 0.1 mol) and dimethylphosphine oxide (2.2 eq, 17.17 g) using standard protocol for dialkylphosphine coupling reaction.

Step2: (9-(3-bromophenyl)-9H-carbazole-2,7-diyl) bis(dimethylphosphine oxide)

A 3-neck, 250 mL round bottom flask equipped with a magnetic stirrer, nitrogen inlet, and reflux condenser, is charged with (9H-carbazole-2,7-diyl)bis(dimethylphosphine oxide) (20 g, 0.063 mol), 1-bromo-3-iodobenzene (1.5 eq. 26.58 g), copper(I)iodide (20 mol %, 12.6 mmol, 2.4 g), 1,10-phenanthroline (20 mol %, 12.6 mmol, 2.27 g) and DMF (170 ml). The flask is sealed, the atmosphere is replaced by nitrogen, reaction mixture is stirred at reflux condition for 24 h.

After cooling down to RT, the reaction mixture is partitioned between water (500 ml) and methylene chloride (200 ml). Organic phase is separated, washed with water, brine, dried over magnesium sulfate, filtered through a short pad of SiO2, and evaporated to dryness. Oily residue solidify upon trituration with hexane, the solid is collected by suction filtration, washed with hexane and dried in vacuum to yield the title product.

Step3: (9-(3-(4,4,5,5-tetramethyl-1,3,2-dioxaborolan-2-yl)phenyl)-9H-carbazole-2,7-diyl)bis(dimethylphosphine oxide)

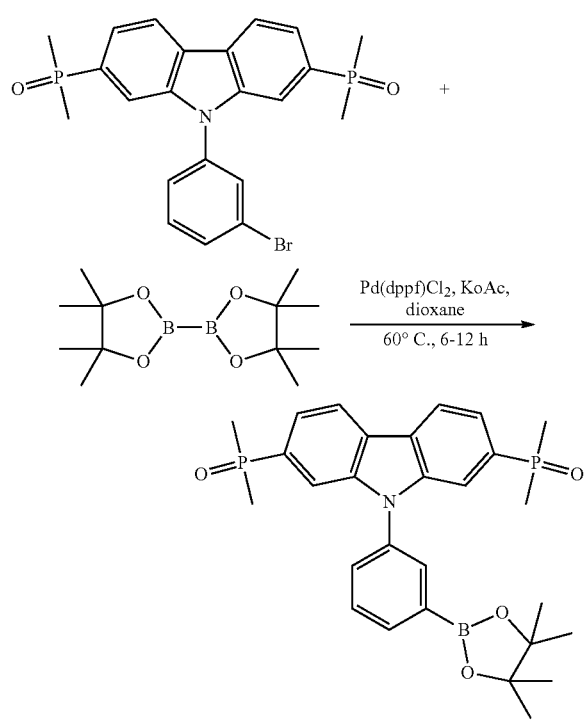

(9-(3-bromophenyl)-9H-carbazole-2,7-diyl)bis(dimethylphosphine oxide) (15 g, 31.6 mmol) is converted to the corresponding boronic ester using the standard protocol, described above.

Step4: (9-(3-(4,6-diphenyl-1,3,5-triazin-2-yl)phenyl)-9H-carbazole-2,7-diyl) bis(dimethylphosphine oxide)

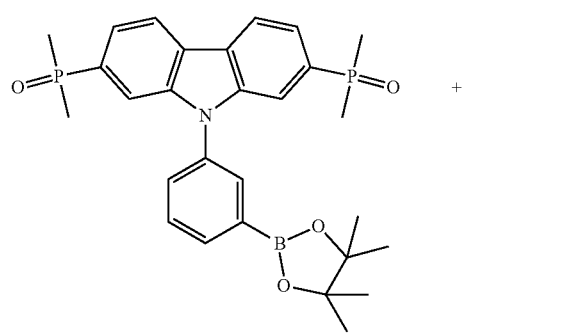

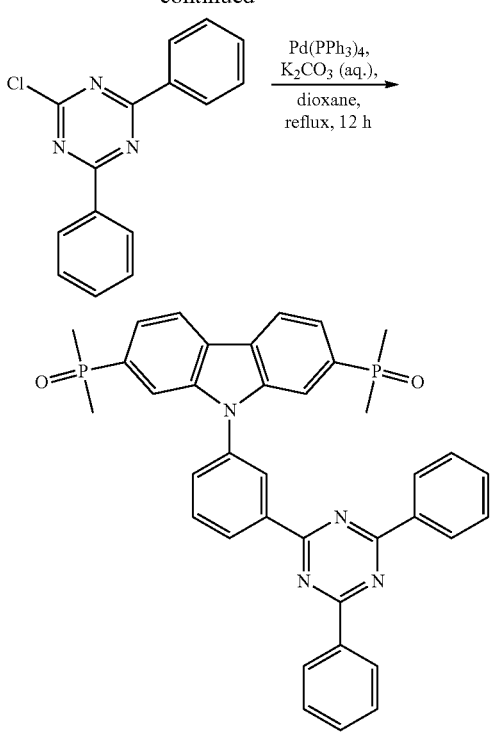

The title compound is prepared from 2-chloro-4,6-diphenyl-1,3,5-triazine (5 g, 18.7 mmol) and (9-(3-(4,4,5,5-tetramethyl-1,3,2-dioxaborolan-2-yl)phenyl)-9H-carbazole-2,7-diyl)bis(dimethylphosphine oxide) (1 eq, 18.7 mmol, 9.74 g) using standard protocol for Suzuki-Miyaura coupling, described above.

Synthesis of (9-phenyl-9-(3-(4-([1,1'-biphenyl]-4-yl)-6-phenyl-1,3,5-triazinyl)phenyl)-9H-fluorene-2,7-diyl)bis(dimethylphosphine oxide)

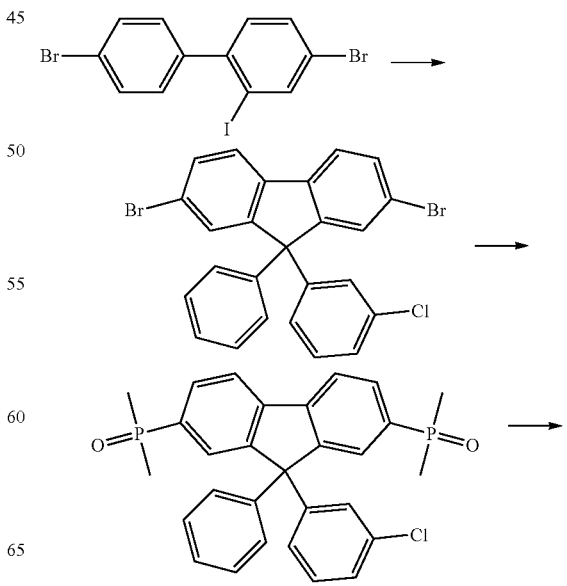

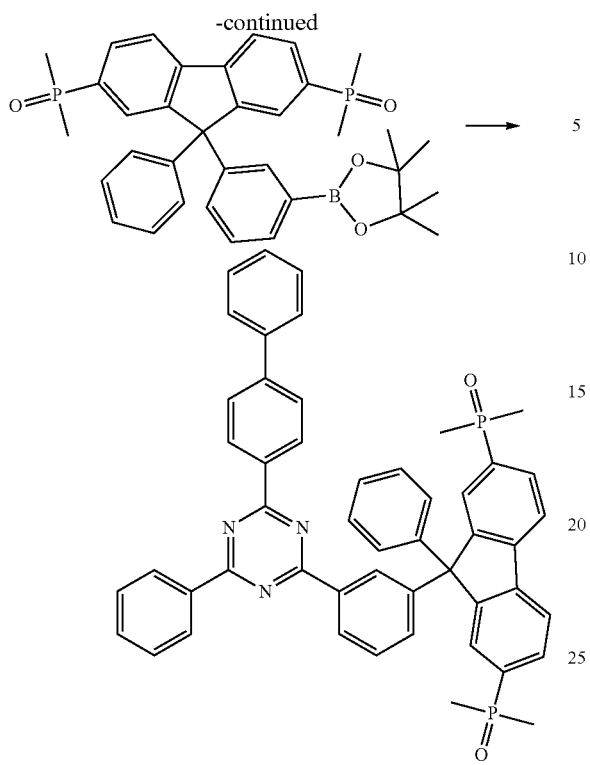

Step1. 2,7-dibromo-9-(3-chlorophenyl)-9-phenyl-9H-fluorene

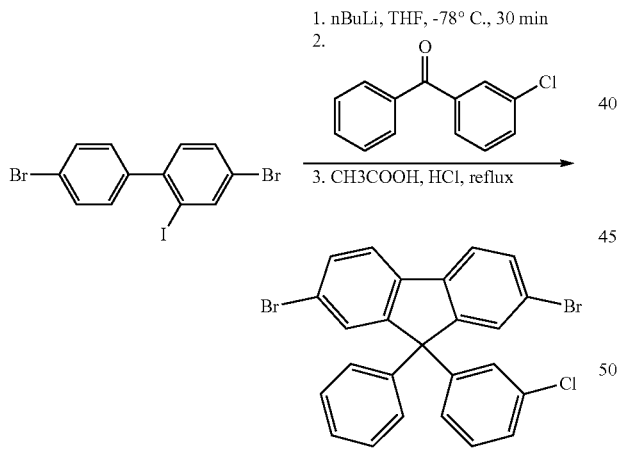

A 3-necked, 250 mL round bottom flask equipped with a magnetic stirrer, thermometer, addition funnel, sealed with a rubber septum, and nitrogen inlet, is charged with 4,4'-dibromo-2-iodo-1,1'-biphenyl (43.8 g, 0.1 mol). The flask is sealed and the atmosphere is replaced by nitrogen. The solid is dissolved in anhydrous THF (100 mL) and the solution is cooled to −78° C. Addition funnel is charged with n-butyl lithium solution (2.5M in hexane, 1 eq. 40 ml). The solution is added to the reaction mixture dropwise at −78° C., the funnel is washed with small amount of anhydrous THF. Ones the addition is complete, the mixture is allowed to react for additional 30 minutes at −78° C., then addition funnel is charged with (3-chlorophenyl)(phenyl)-methanone (1 eq, 0.1 mol, 21.7 g), dissolved in 100 ml of anhydrous THF. This solution is added to reaction mixture dropwise at −78° C., reaction is stirred for additional 30 min at −78° C., then allowed to reach the room temperature overnight.

The solvent is evaporated at reduced pressure, the residue is dissolved in glacial acetic acid (150 ml). Concentrated hydrochloric acid solution (32%, 16 ml) is added, he mixture was heated to reflux for 3.5 h and stirred overnight at room temperature. Obtained suspension is diluted with water, extracted with DCM. Combined organic extracts are washed with water, dried over magnesium sulfate and evaporated to a dryness yielding a crude product. Final purification is achieved by recrystallization from isopropanol (700 ml).

Step2: (9-(3-chlorophenyl)-9-phenyl-9H-fluorene-2,7-diyl)bis(dimethylphosphine oxide)

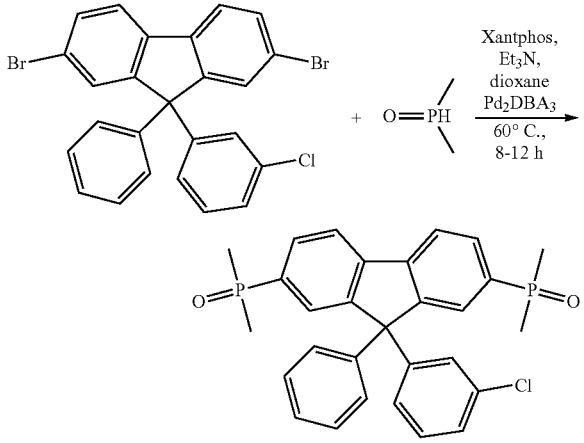

The title compound is prepared from 2,7-dibromo-9-(3-chlorophenyl)-9-phenyl-9H-fluorene (30 g, 58.8 mmol) using the standard procedure, described above. Purification of the final compound is achieved by re-crystallization from chlorobenzene.

Step3: (9-phenyl-9-(3-(4,4,5,5-tetramethyl-1,3,2-dioxaborolan-2-yl)phenyl)-9H-fluorene-2,7-diyl)bis(dimethylphosphine oxide)

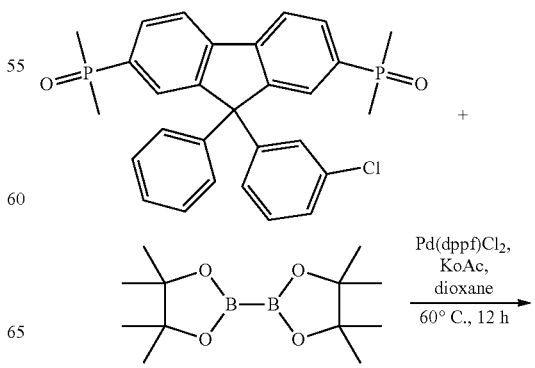

87

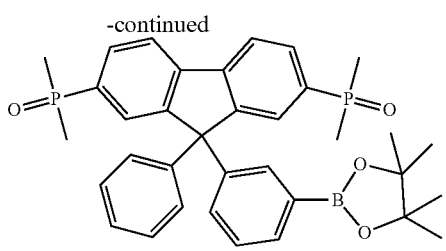

(9-(3-chlorophenyl)-9-phenyl-9H-fluorene-2,7-diyl)bis(dimethylphosphine oxide) (20 g, 39.6 mmol) is converted to the corresponding boronic ester using the standard protocol, described above.

Step4: (9-phenyl-9-(3-(4-([1,1'-biphenyl]-4-yl)-6-phenyl-1,3,5-triazinyl)phenyl)-9H-fluorene-2,7-diyl)bis(dimethylphosphine oxide)

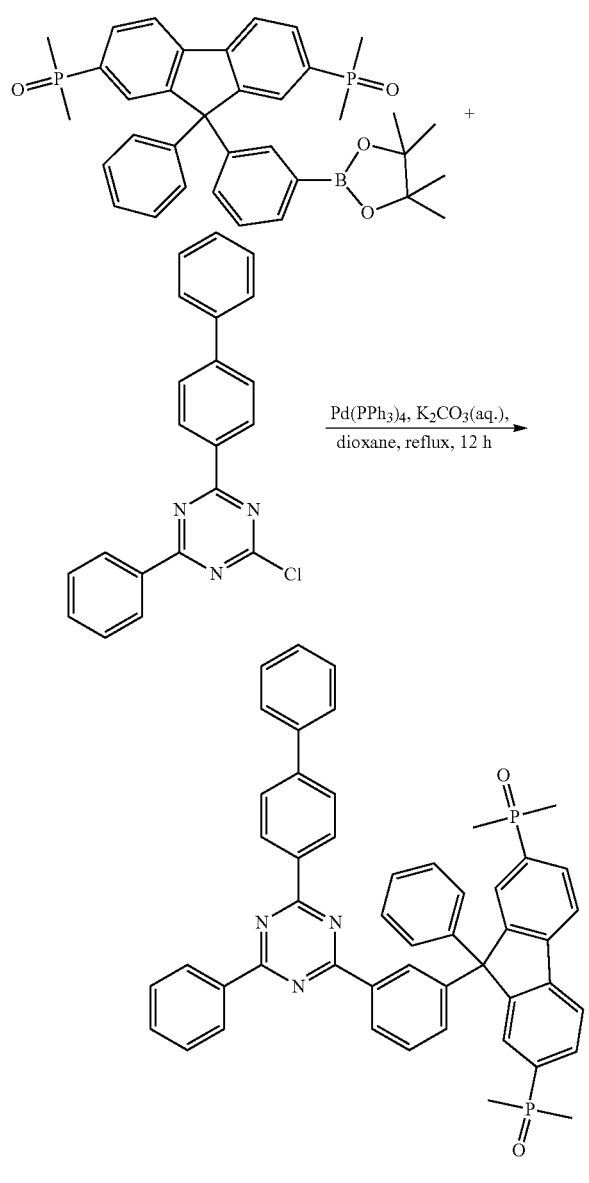

The title compound was prepared from (9-phenyl-9-(3-(4,4,5,5-tetramethyl-1,3,2-dioxaborolan-2-yl)phenyl)-9H-fluorene-2,7-diyl)bis(dimethylphosphine oxide) (16.5 g, 27.7 mmol) and 2-([1,1'-biphenyl]-4-yl)-4-chloro-6-phenyl-1,3,5-triazine (1 eq, 27.7 mmol, 9.52 g) using standard protocol for Suzuki-Miyaura coupling.

88

(5-(4-(4-(4-(dibenzo[b,d]furan-3-yl)-6-phenyl-1,3,5-triazin-2-yl)phenyl)naphthalen-1-yl)-1,3-phenylene)bis(dimethylphosphine oxide)

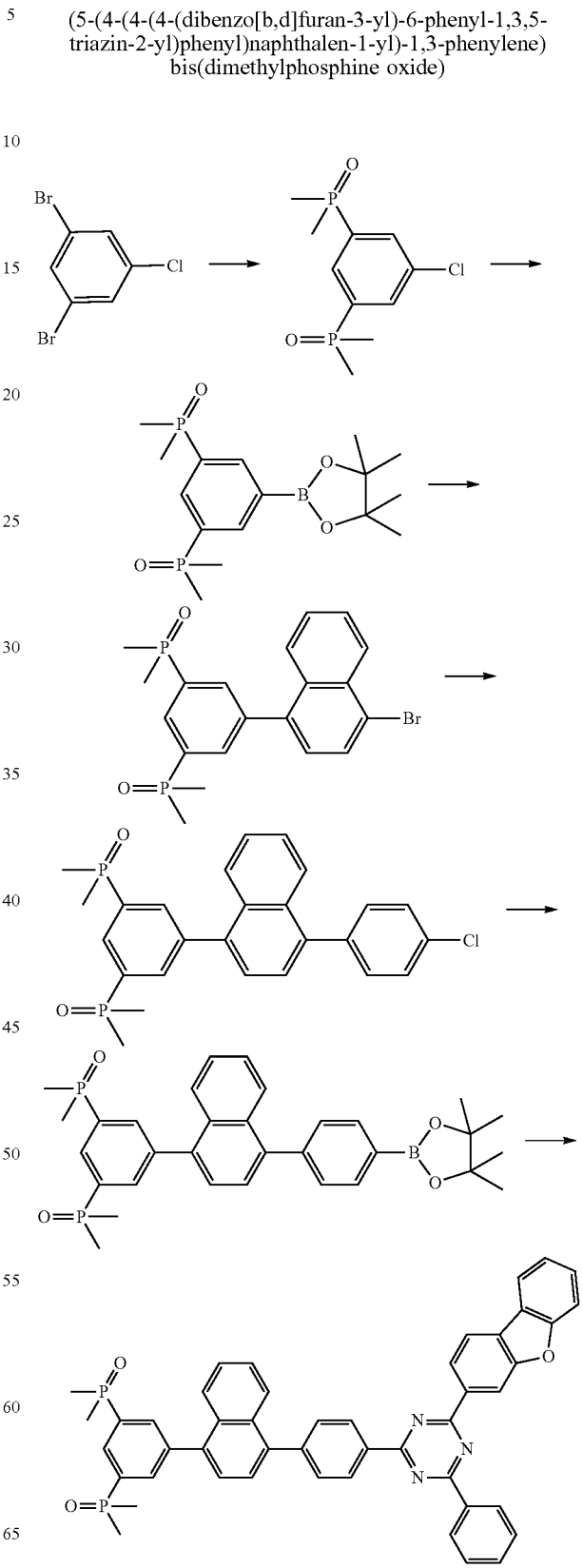

Step1: (5-chloro-1,3-phenylene)bis(dimethylphosphine oxide)

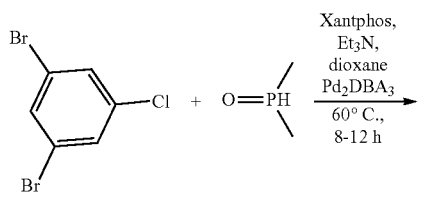

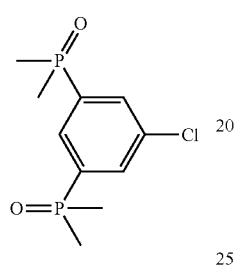

The title compound is obtained from 1,3-dibromo-5-chlorobenzene (54.07 g, 0.2 mol) and dimethylphosphine oxide (2 eq. 0.4 mol, 31.22 g) using the standard procedure for coupling of dialkylphosphine oxide

Step2: (5-(4,4,5,5-tetramethyl-, 3,2-dioxaborolan-2-yl)-1,3-phenylene)bis(dimethylphosphine oxide)

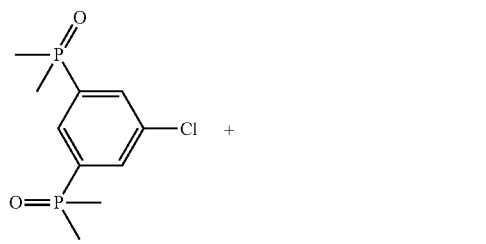

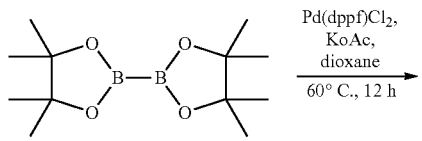

(5-chloro-1,3-phenylene)bis(dimethylphosphine oxide) (34.4 g, 0.13 mol) is converted to the title compound using standard protocol, described above.

Step3: (5-(4-bromonaphthalen-1-yl)-1,3-phenylene)bis(dimethylphosphine oxide)

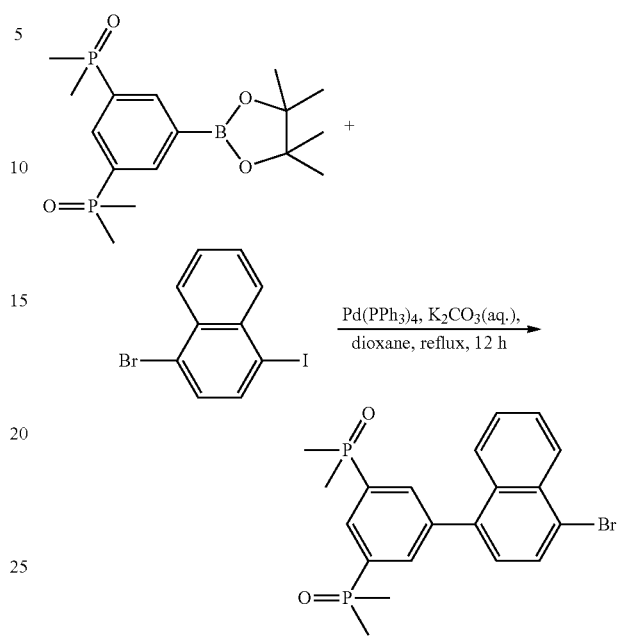

The title compound is prepared from (5-(4,4,5,5-tetramethyl-1,3,2-dioxaborolan-2-yl)-1,3 phenylene)bis(dimethylphosphine oxide) (28.7 g, 8.06 mmol) and 1-bromo-4-iodonaphthalene (1 eq. 8.06 mmol, 26.8 g) using standard protocol for Suzuki-Miyaura coupling

Step4 (5-(4-(4-chlorophenyl)naphthalen-1-yl)-1,3-phenylene)bis(dimethylphosphine oxide)

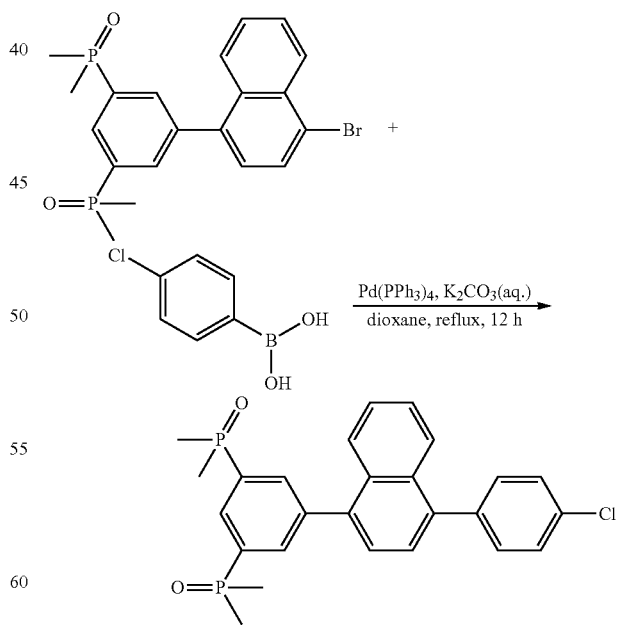

The title compound is prepared from (5-(4-bromonaphthalen-1-yl)-1,3-phenylene) bis(dimethylphosphine oxide) (30 g, 6.89 mmol) and (4-chlorophenyl)boronic acid (1 eq. 6.89 mmol, 10.78 g) using standard protocol for Suzuki-Miyaura coupling Step 5: (5-(4-(4-(4,4,5,5-tetramethyl-1,3,2-dioxaborolan-2-yl)phenyl)naphthalen-1-yl)-1,3-phenylene)bis(dimethylphosphine oxide)

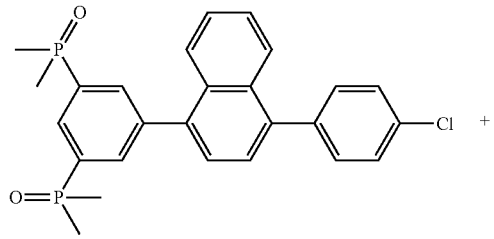

+

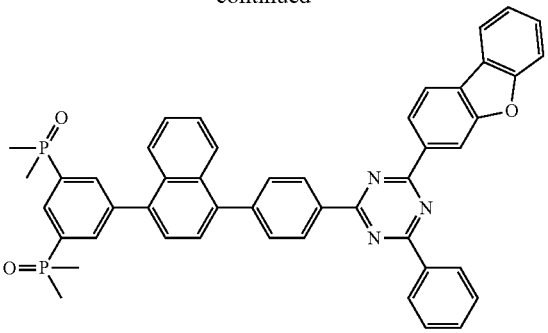

Pd(dppf)Cl$_2$, KoAc, dioxane
60° C., 12 h

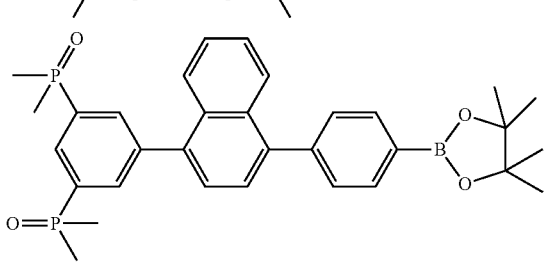

(5-(4-(4-chlorophenyl)naphthalen-1-yl)-1,3-phenylene)bis(dimethylphosphine oxide) (25.7 g, 5.5 mmol) is converted to corresponding boronic ester using the standard procedure, described above.

Step 6: (5-(4-(4-(4-(dibenzo[b,d]furan-3-yl)-6-phenyl-1,3,5-triazin-2-yl)phenyl)naphthalen-1-yl)-1,3-phenylene)bis(dimethylphosphine oxide)

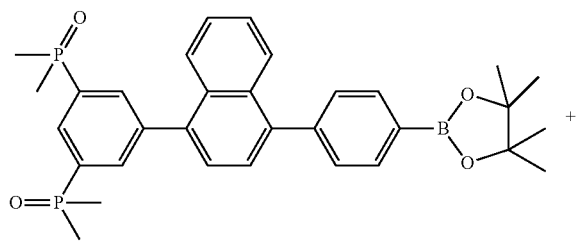

+

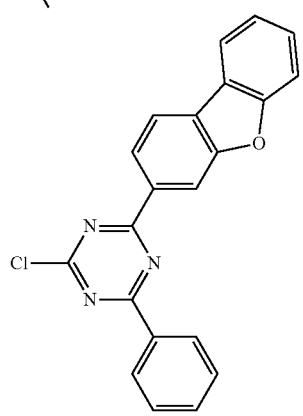

Pd(PPh$_3$)$_4$, K$_2$CO$_3$(aq.)
dioxane, reflux, 12 h

The title compound is prepared from (5-(4-(4-(4,4,5,5-tetramethyl-1,3,2-dioxaborolan-2-yl)phenyl)naphthalen-1-yl)-1,3-phenylene)bis(dimethylphosphine oxide) (12 g, 2.15 mmol) and 2-chloro-4-(dibenzo[b,d]furan-3-yl)-6-phenyl-1,3,5-triazine (1 eq. 2.15 mmol, 7.69) using standard protocol for Suzuki-Miyaura coupling Synthesis of (5-(4-(4-(4-(dibenzo[b,d]furan-3-yl)quinazolin-2-yl)phenyl)naphthalen-1-yl)-1,3-phenylene)bis(dimethylphosphine oxide)

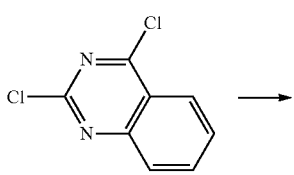

→

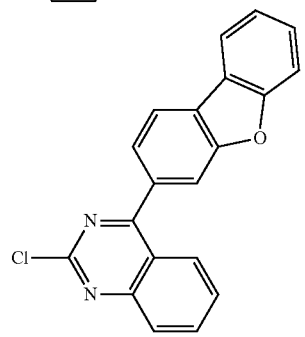

→

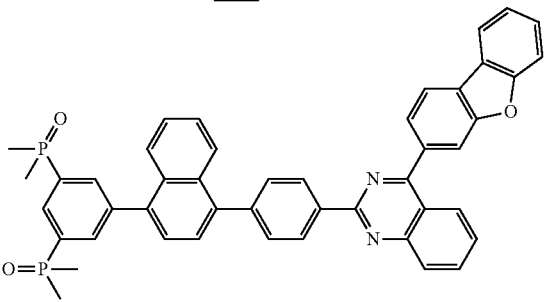

Step 1: 2-chloro-4-(dibenzo[b,d]furan-3-yl)quinazoline

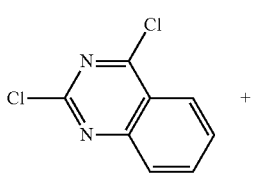

+

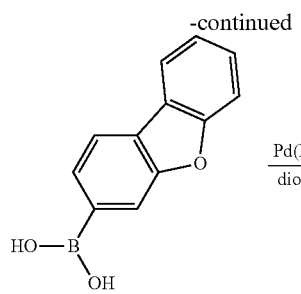

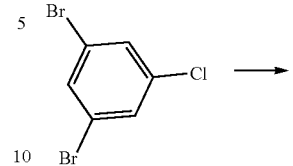

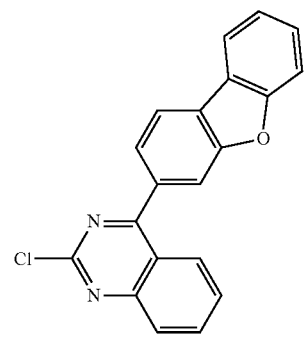

The title compound is prepared from 2,4-dichloroquinazoline (25 g, 0.126 mol) and dibenzo[b,d]furan-3-ylboronic acid (1 eq. 0.126 mol, 26.6 g) using standard protocol for Suzuki-Miyaura coupling Step2: (5-(4-(4-(4-(dibenzo[b, d]furan-3-yl)quinazolin-2-yl)phenyl)naphthalen-1-yl)-1,3-phenylene)bis(dimethylphosphine oxide)

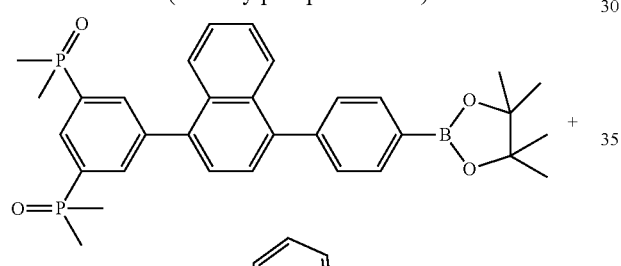

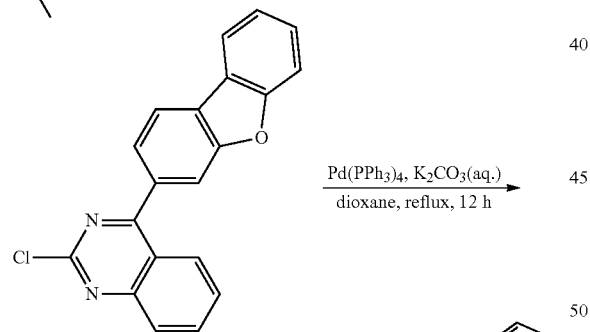

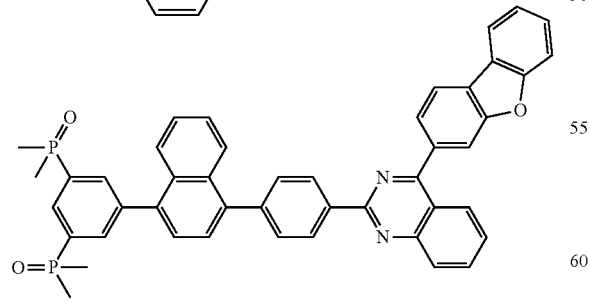

The title compound is prepared from (5-(4-(4-(4,4,5,5-tetramethyl-1,3,2-dioxaborolan-2-yl)phenyl)naphthalen-1-yl)-1,3-phenylene)bis(dimethylphosphine oxide) (12 g, 2.15 mmol) and 2-chloro-4-(dibenzo[b,d]furan-3-yl)quinazoline (1 eq. 2.15 mmol, 7.1 g) using standard protocol for Suzuki-Miyaura coupling.

Synthesis of (5'-(4-([1,1'-biphenyl]-3-yl)-6-(dibenzo[b,d]furan-3-yl)-1,3,5-triazin-2-yl)-[1,1':3',1''-terphenyl]-3,3''-diyl)bis(dimethylphosphine oxide)

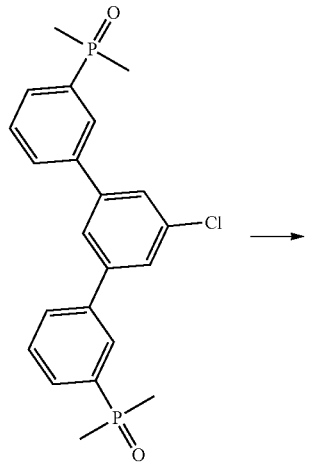

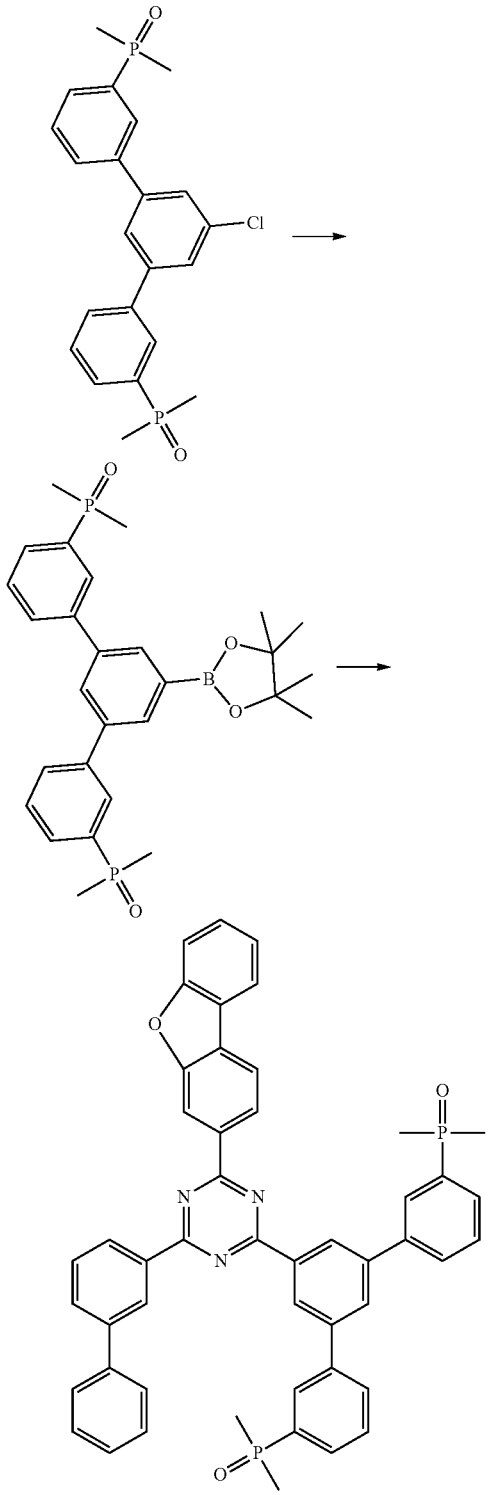

95

Step 1: (5'-chloro-[1,1':3',1''-terphenyl]-3,3''-diyl)bis(dimethylphosphine oxide)

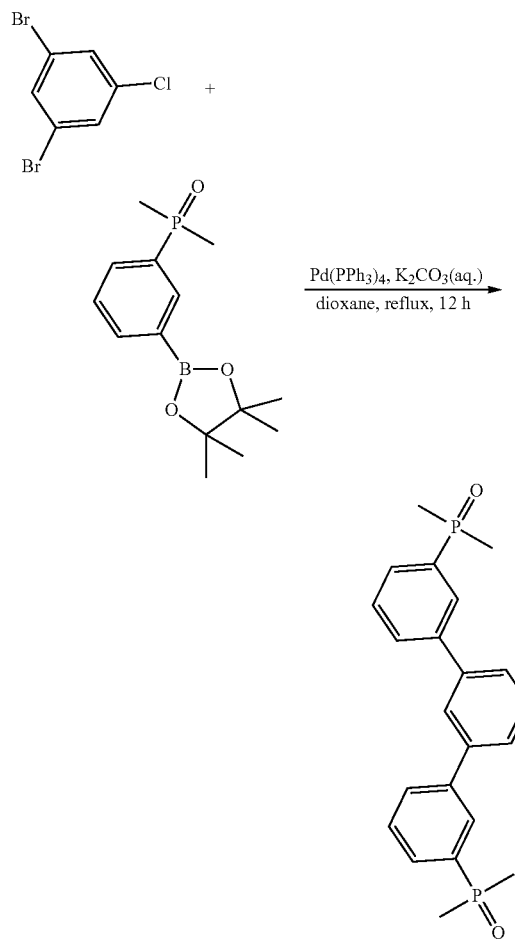

The title compound is prepared from 1,3-dibromo-5-chlorobenzene (54.07 g, 0.2 mol) and dimethyl(3-(4,4,5,5-tetramethyl-1,3,2-dioxaborolan-2-yl)phenyl)phosphine oxide (2 eq. 0.4 mol, 112.04 g) using standard protocol for Suzuki-Miyaura coupling

Step 2: (5'-(4,4,5,5-tetramethyl-1,3,2-dioxaborolan-2-yl)-[1,1':3',1''-terphenyl]-3,3''-diyl)bis(dimethylphosphine oxide)

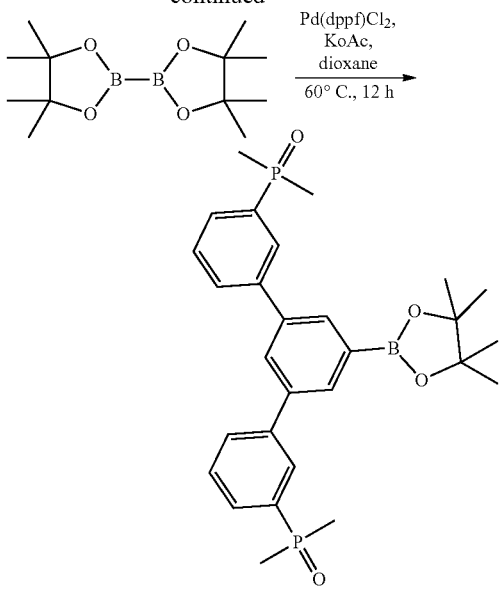

(5'-chloro-[1,1':3',1''-terphenyl]-3,3''-diyl)bis(dimethylphosphine oxide) (54 g, 0.13 mol) is converted to the boronic ester using the procedure, described above.

Step 3: (5'-(4-([1,1'-biphenyl]-3-yl)-6-(dibenzo[b,d]furan-3-yl)-1,3,5-triazin-2-yl)-[1,1':3',1''-terphenyl]-3,3''-diyl)bis(dimethylphosphine oxide)

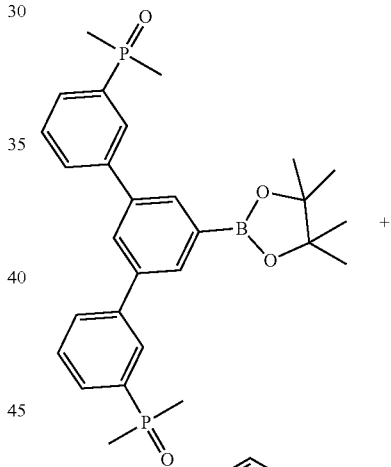

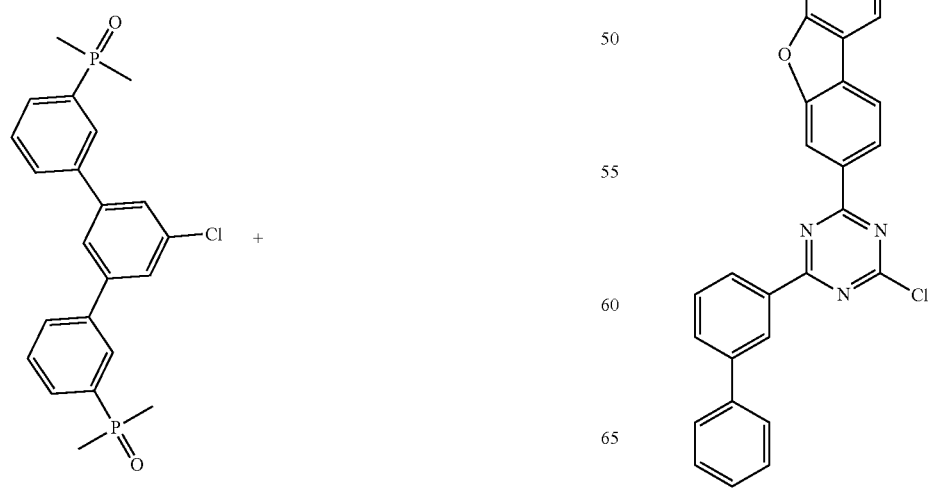

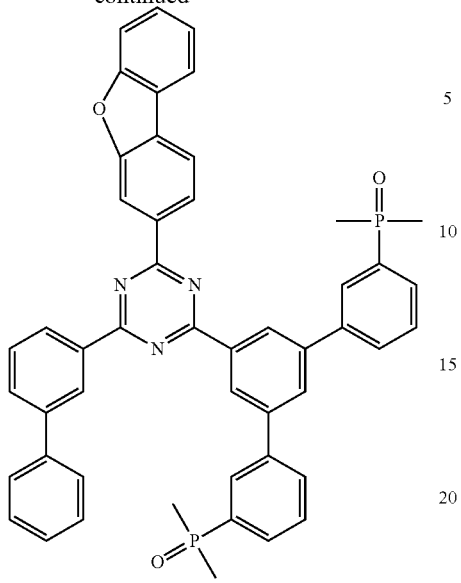

The title compound is prepared from (5'-(4,4,5,5-tetramethyl-1,3,2-dioxaborolan-2-yl)-[1,1': 3',1"-terphenyl]-3,3"-diyl)bis(dimethylphosphine oxide) (10 g, 19.7 mmol) and 2-([1,1'-biphenyl]-3-yl)-4-chloro-6-(dibenzo[b,d]furan-3-yl)-1,3,5-triazine (1 eq. 19.7 mol, 8.54 g) using standard protocol for Suzuki-Miyaura coupling Synthesis of (5'-(4-(dibenzo[b,d]thiophen-2-yl)-6-(dibenzo[b,d]thiophen-3-yl)pyrimidin-2-yl)-[1,1':3',1"-terphenyl]-3,3"-diyl)bis(dimethylphosphine oxide)

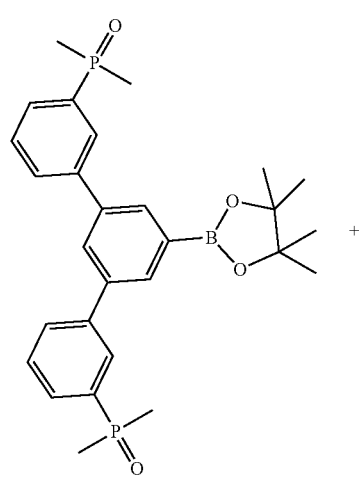 +

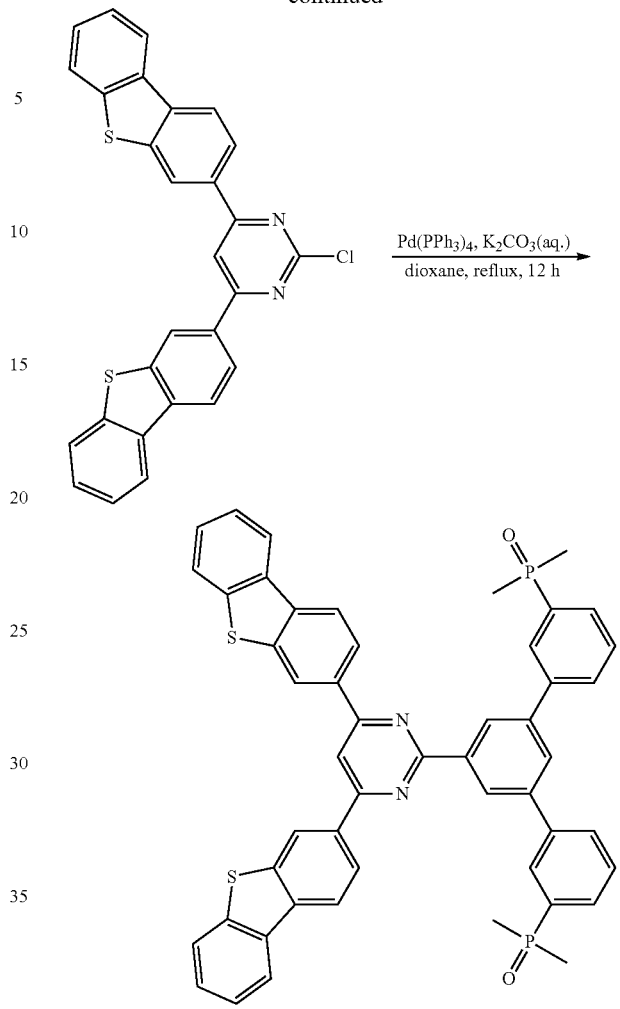

The title compound is prepared from (5'-(4,4,5,5-tetramethyl-1,3,2-dioxaborolan-2-yl)-[1,1':3',1"-terphenyl]-3,3"-diyl)bis(dimethylphosphine oxide) (10 g, 19.7 mmol) and 2-chloro-4,6-bis(dibenzo[b,d]thiophen-3-yl)pyrimidine (1 eq. 19.7 mol, 9.43 g) using standard protocol for Suzuki-Miyaura coupling General Procedure for Fabrication of Organic Electronic Devices Electron-only devices and OLEDs were prepared to demonstrate the technical benefit utilizing the compounds of formula 1 in an organic electronic device.

Electron-Only Devices

For electron-only devices (EOD), see Table 5 and 6, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes. 100 nm Ag were deposited as anode on the glass at a pressure of $10^{-5}$ to $10^{-7}$ mbar.

Then, MgAg alloy (90:10 vol.-%) was deposited on the anode electrode to form a layer with a thickness of 30 nm.

Then, LiQ was deposited on the MgAg layer to form a layer with a thickness of 1 nm.

Then, an organic semiconductor layer was deposited on the LiQ layer to form an organic semiconductor layer with a thickness of 36 nm.

In examples 1 to 4 (Table 5), the organic semiconductor layer consisted of compound of formula 1. In comparative example 1, MX1 [anthracene-9,10-diylbis(4,1-phenylene)) bis(diphenyl-phosphine oxide), CAS 1257261-60-1] was used instead, see Table 5.

In examples 5 to 8 (Table 6), the organic semiconductor layer comprised 70 vol.-% compound of formula 1 and 30 vol.-% alkali organic complex. In comparative example 1, MX1 was used in place of compound of formula 1, see Table 6.

Then, LiQ was deposited to form a layer with a thickness of 1 nm.

Then, MgAg alloy (90:10 vol.-%) was deposited on the LiQ layer to form a cathode electrode with a thickness of 30 nm.

Bottom Emission Devices with an Evaporated Emission Layer

For bottom emission devices—Examples 9 to 12 and comparative example 3 in Table 7, a 15 Ω/cm² glass substrate with 90 nm ITO (available from Corning Co.) was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare a first electrode.

Then, 97 vol.-% of Biphenyl-4-yl(9,9-diphenyl-9H-fluoren-2-yl)-[4-(9-phenyl-9H-carbazol-3-yl)phenyl]-amine (CAS 1242056-42-3) and 3 vol.-% of 2,2',2"-(cyclopropane-1,2,3-triylidene)tris(2-(p-cyanotetrafluorophenyl)acetonitrile) was vacuum deposited on the ITO electrode, to form a HIL having a thickness of 10 nm. Then Biphenyl-4-yl(9,9-diphenyl-9H-fluoren-2-yl)-[4-(9-phenyl-9H-carbazol-3-yl)phenyl]-amine was vacuum deposited on the HIL, to form a HTL having a thickness of 120 nm. 97 vol.-% of 2-(10-phenyl-9-anthracenyl)-benzo[b]naphtho[2,3-d]furan (CAS 1627916-48-6) as a host and 3 vol.-% of NUBD370 (Sun Fine Chemicals) as a dopant were deposited on the HTL, to form a blue-emitting EML with a thickness of 20 nm.

Then, the electron transport layer is formed directly on the EML. In examples 9 to 12, the electron transport layer is formed by deposing the compound of formula 1 from a first deposition source and the alkali organic complex from a second deposition source directly on the EML. In comparative example 3, MX1 is deposed on the EML. The alkali organic complex is LI-1 (Lithium tetra(1H-pyrazol-1-yl)borate). The thickness of the electron transport layer is 36 nm.

Then, the cathode electrode layer is formed by evaporating aluminum at ultra-high vacuum of $10^{-7}$ bar and deposing the cathode layer directly on the organic semiconductor layer. A thermal single co-evaporation is performed with a rate of 0, 1 to 10 nm/s (0.01 to 1 Å/s) in order to generate a homogeneous cathode electrode. The thickness of the cathode electrode layer is 100 nm.

Bottom Emission Devices with a Solution-Processed Emission Layer

For bottom emission devices, a 15 Ω/cm² glass substrate with 90 nm ITO (available from Corning Co.) was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare a first electrode.

Then, PEDOT:PSS (Clevios P VP AI 4083) is spin-coated directly on top of the first electrode to form a 55 nm thick HIL. The HIL is baked on hotplate at 150° C. for 5 min. Then, a light-emitting polymer, for example MEH-PPV, is spin-coated directly on top of the HIL to form a 40 nm thick EML. The EML is baked on a hotplate at 80° C. for 10 min.

The device is transferred to an evaporation chamber and the following layers are deposited in high vacuum.

The compound of formula 1 and an alkali organic complex are deposed directly on top of the EML to form the organic semiconductor layer with a thickness of 4 nm. A cathode electrode layer is formed by deposing a 100 nm thick layer of aluminum directly on top of the organic semiconductor layer.

Pn Junction Device as Model for an OLED Comprising at Least Two Emission Layers

The fabrication of OLEDs comprising at least two emission layers is time-consuming and expensive. Therefore, the effectiveness of the organic semiconductor layer of the present invention in a pn junction was tested without emission layers. In this arrangement, the organic semiconductor layer functions as n-type charge generation layer (CGL) and is arranged between the anode electrode and the cathode electrode and is in direct contact with the p-type CGL.

For pn junction devices, a 15 Ω/cm² glass substrate with 90 nm ITO (available from Corning Co.) was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare a first electrode.

Then, 97 vol.-% of Biphenyl-4-yl(9,9-diphenyl-9H-fluoren-2-yl)-[4-(9-phenyl-9H-carbazol-3-yl)phenyl]-amine (CAS 1242056-42-3) and 3 vol.-% of 2,2',2"-(cyclopropane-1,2,3-triylidene)tris(2-(p-cyanotetrafluorophenyl)acetonitrile) was vacuum deposited on the ITO electrode, to form a HIL having a thickness of 10 nm. Then 2,4-diphenyl-6-(3'-(triphenylen-2-yl)-[1,1'-biphenyl]-3-yl)-1,3,5-triazine (CAS 1638271-85-8) was vacuum deposited on the HIL, to form an electron blocking layer (EBL) having a thickness of 130 nm.

Then, the organic semiconductor layer is formed by deposing a matrix compound and metal organic complex by deposing the matrix compound from a first deposition source and rare earth metal dopant from a second deposition source directly on the EBL.

Then, the p-type CGL is formed by deposing the host and p-type dopant directly onto the organic semiconductor layer. 97 vol.-% of Biphenyl-4-yl(9,9-diphenyl-9H-fluoren-2-yl)-[4-(9-phenyl-9H-carbazol-3-yl)phenyl]-amine, referred to as HT-1, and 3 vol.-% of 2,2',2"-(cyclopropane-1,2,3-triylidene)tris(2-(p-cyanotetrafluorophenyl)acetonitrile), referred to as Dopant 1, was vacuum deposited to form a p-type CGL having a thickness of 10 nm.

Then, a layer of 30 nm Biphenyl-4-yl(9,9-diphenyl-9H-fluoren-2-yl)-[4-(9-phenyl-9H-carbazol-3-yl)phenyl]-amine is deposed directly on the p-type CGL to form a hole blocking layer (HBL).

Then, the cathode electrode layer is formed by evaporating aluminum at ultra-high vacuum of $10^{-7}$ bar and deposing the aluminum layer directly on the organic semiconductor layer. A thermal single co-evaporation of one or several metals is performed with a rate of 0, 1 to 10 nm/s (0.01 to 1 Å/s) in order to generate a homogeneous cathode electrode. The thickness of the cathode electrode layer is 100 nm.

Top Emission Devices with an Evaporated Emission Layer

For top emission devices—Examples 13 to 21 in Table 8, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare the substrate. 100 nm Ag was deposited on the substrate to form a first electrode.

92 vol.-% of Biphenyl-4-yl(9,9-diphenyl-9H-fluoren-2-yl)-[4-(9-phenyl-9H-carbazol-3-yl)phenyl]-amine (CAS 1242056-42-3) and 8 vol.-% of 2,2',2''-(cyclopropane-1,2,3-triylidene)tris(2-(p-cyanotetrafluorophenyl)acetonitrile) was vacuum deposited on the first electrode, to form a HIL having a thickness of 10 nm. Biphenyl-4-yl(9,9-diphenyl-9H-fluoren-2-yl)-[4-(9-phenyl-9H-carbazol-3-yl)phenyl]-amine was vacuum deposited on the HIL, to form a HTL having a thickness of 121 nm (Examples 13 to 20) or 118 nm (Example 21). 97 vol.-% H09 (Sun Fine Chemicals) as a host and 3 vol.-% BD200 (Sun Fine Chemicals) as a fluorescent blue emitting dopant were deposited on the HTL, to form a blue-emitting EML with a thickness of 20 nm. 2,4-diphenyl-6-(4',5',6'-triphenyl-[1,1':2',1''':3'',1''''':3''',1''''-quinquephenyl]-3''''-yl)-1,3,5-triazine was deposited directly on the EML to form a hole blocking layer (HBL) with a thickness of 5 nm.

The electron transport layer (ETL) is formed directly on the HBL. In examples 13, 15, 17, 19 and 21, the ETL is formed by deposing compound of formula 1 directly on the EML. In examples 14, 16, 18 and 20, the electron transport layer is formed by deposing the compound of formula 1 from a first deposition source and the alkali organic complex from a second deposition source directly on the EML. The alkali organic complex is LI-1 (Lithium tetra(1H-pyrazol-1-yl)borate). The composition and thickness of the ETL can be seen in Table 8.

In examples 13 and 14 the cathode electrode layer is formed directly on the ETL.

In examples 15 to 21, an electron injection layer (EIL) is formed directly on the ETL, followed by the cathode electrode layer. The composition of the material loaded into the VTE sources and the thickness of the deposited layer can be seen in Table 8. Zn:Na alloy is evaporated from one VTE source, see examples 17 to 20. Yb and KI are evaporated from two VTE sources, see example 21

The cathode electrode layer is formed by evaporating the cathode material at ultra-high vacuum of $10^{-7}$ bar and deposing the cathode layer directly on the ETL or EIL. A thermal single co-evaporation or sputtering process of one or several metals is performed with a rate of 0, 1 to 10 nm/s (0.01 to 1 Å/s) in order to generate a homogeneous cathode electrode. In examples 13 to 20, the cathode electrode is formed from 11 nm Ag:Mg (85:15 vol.-%). In example 21, the cathode electrode is formed from 11 nm Ag. Biphenyl-4-yl(9,9-diphenyl-9H-fluoren-2-yl)-[4-(9-phenyl-9H-carbazol-3-yl)phenyl]-amine was vacuum deposited on the cathode electrode, to form a capping layer having a thickness of 60 nm (Examples 13 to 21) or 75 nm (Example 21).

The device is protected from ambient conditions by encapsulation of the device with a glass slide. Thereby, a cavity is formed, which comprises a getter material for further protection.

To assess the performance of the inventive examples compared to the prior art, the current efficiency is measured under ambient conditions (20° C.). Current voltage measurements are performed using a Keithley 2400 source meter, and recorded in V. At 10 mA/cm$^2$ for bottom emission and 10 mA/cm$^2$ for top emission devices, a calibrated spectrometer CAS140 from Instrument Systems is used for measurement of CIE coordinates and brightness in Candela. Lifetime LT of bottom emission device is measured at ambient conditions (20° C.) and 10 mA/cm$^2$, using a Keithley 2400 source meter, and recorded in hours. Lifetime LT of top emission device is measured at ambient conditions (20° C.) and 8 mA/cm$^2$. The brightness of the device is measured using a calibrated photo diode. The lifetime LT is defined as the time till the brightness of the device is reduced to 97% of its initial value.

In pn junction devices, the operating voltage is determined at 10 mA/cm$^2$ as described for OLEDs above.

Technical Effect of the Invention

In Table 5 are shown the dipole moment, glass transition temperature Tg, rate onset temperature $T_{RO}$ of compound of formula 1 (examples 1 to 4) and of comparative example 1. Additionally, the operating voltage of electron-only devices at 10 mA/cm$^2$ comprising an organic semiconductor layer consisting of compound of formula 1 is shown. Operating voltage in electron-only devices provides an indirect indication of conductivity. The lower the operating voltage the higher the conductivity.

In comparative example 1, MX1 has a dipole moment of 3.52 Debye and a rate onset temperature of 308° C. The operating voltage is high at 2.4 V.

In example 1, the dipole moment is 0.24 Debye, the rate onset temperature is reduced at 279° C. and the operating voltage is reduced significantly to 0.1 V.

In examples 2 to 4, the dipole moment is between 0.01 and 0.1 Debye, the rate onset temperature is between 286 and 354° C. and the operating voltage is very low in all examples.

In summary, compound of formula 1 may have very high conductivity and a significant reduction in operating voltage may be achieved. The glass transition temperature and rate onset temperature are within the range acceptable for mass production of organic semiconductor layers.

TABLE 5

Dipole moment (calculated with B3LYP_Gaussian/6-31G), glass transition temperature, rate onset temperature and operating voltage in electron-only devices

| | Name | Formula | Dipole moment [Debye] | Tg [° C.] | $T_{RO}$ [° C.] | Operating voltage at 10 mA/cm$^2$ [V] |
|---|---|---|---|---|---|---|
| Comp. example 1 | MX1 | | 3.52 | — | 308 | 2.4 |

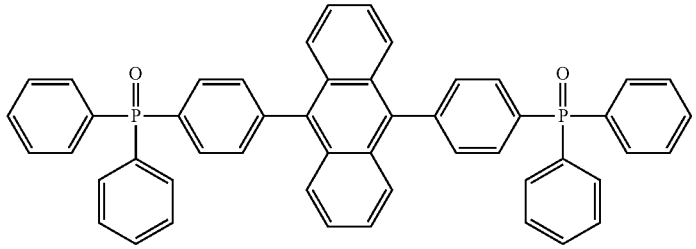 [SMILES: O=P(c1ccccc1)(c1ccccc1)c1ccc(-c2c3ccccc3c(-c3ccc(P(=O)(c4ccccc4)c4ccccc4)cc3)c3ccccc23)cc1]

TABLE 5-continued

Dipole moment (calculated with B3LYP_Gaussian/6-31G), glass transition temperature, rate onset temperature and operating voltage in electron-only devices

| Name | Formula | Dipole moment [Debye] | Tg [° C.] | $T_{RO}$ [° C.] | Operating voltage at 10 mA/cm² [V] |
|---|---|---|---|---|---|
| Example 1 | MX2 | 0.24 | — | 279 | 0.1 |
| Example 2 | MX3 | 0.01 | — | 286 | 0.6 |
| Example 3 | MX4 | 0.10 | 201 | 354 | 0.3 |
| Example 4 | MX5 | 0.08 | 141 | 298 | 0.5 |

In Table 6 are shown operating voltages of an organic semiconductor layer comprising a compound of formula 1 (examples 5 to 8) and alkali organic complex. The alkali organic complex is LI-1 (Lithium tetra(1H-pyrazol-1-yl) borate).

In comparative example 2, the operating voltage is very high at 0.95 V. In examples 5 to 8, the operating voltage is reduced significantly to 0.3 to 0.5 V. Thereby, the beneficial effect of high conductivity of compound of formula 1 is observed also in an organic semiconductor layer comprising further an alkali organic complex.

TABLE 6

Electron-only devices of an organic semiconductor layer comprising a compound of formula 1 and an alkali organic complex

| | Compound of formula 1 | vol.-% compound of formula 1 | Alkali organic complex | vol.-% alkali organic complex | Operating voltage at 10 mA/cm$^2$ (V) |
|---|---|---|---|---|---|
| Comparative example 2 | MX1 | 70 | LI-1 | 30 | 0.95 |
| Example 5 | MX2 | 70 | LI-1 | 30 | 0.3 |
| Example 6 | MX3 | 70 | LI-1 | 30 | 0.3 |
| Example 7 | MX4 | 70 | LI-1 | 30 | 0.5 |
| Example 8 | MX5 | 70 | LI-1 | 30 | 0.3 |

In Table 7, see below, data for bottom emission OLEDs are shown. In examples 9 to 12, the first electron transport layer comprises compound of formula 1 and alkali organic complex LI-1. In comparative example 3, the first electron transport layer comprises MX1 and alkali organic complex LI-1. As can be seen in Table 7, the operating voltage is reduced significantly in examples 9 to 12 compared to comparative example 3. Additionally, in example 10 to 12, the cd/A efficiency is improved.

In summary, a beneficial effect of compound of formula ion operating voltage is observed when used in the first or second electron transport layer.

In Table 8, data for top emission OLEDs are shown. In example 13 and 14, the electron transport layer comprises a compound of formula 1. The operating voltage is low at 3.7 and 4.05 V, respectively, and the cd/A efficiency is very high at 9.5 and 7.3 cd/A, respectively.

The operating voltage is reduced further when an EIL is arranged between the electron transport layer comprising compound of formula 1 and the cathode electrode, see examples 15 to 21. Particularly low operating voltage can be achieved when a metal composition comprising Na and Zn is evaporated from one VTE source to form an EIL, see examples 17 to 21. A similar beneficial effect can be achieved, when Yb and KI are evaporated together from two VTE sources to form an EIL, see Example 21.

TABLE 7

Bottom emission OLED performance of a first electron transport layer comprising a compound of formula 1 and an alkali organic complex

| | Compound of formula 1 | vol.-% compound of formula 1 | Alkali organic complex | vol.-% alkali organic complex | Thickness ETL1 / nm | Operating voltage at 10 mA/cm$^2$ (V) | cd/A efficiency at 10 mA/cm$^2$ (cd/A) |
|---|---|---|---|---|---|---|---|
| Comparative example 3 | MX1 | 70 | LI-1 | 30 | 36 | 4.25 | 5.9 |
| Example 9 | MX2 | 70 | LI-1 | 30 | 36 | 3.6 | 5.85 |
| Example 10 | MX3 | 70 | LI-1 | 30 | 36 | 3.6 | 6.1 |
| Example 11 | MX4 | 70 | LI-1 | 30 | 36 | 3.9 | 6.3 |
| Example 12 | MX5 | 70 | LI-1 | 30 | 36 | 3.6 | 6.25 |

TABLE 8

Top emission OLED performance of an electron transport layer comprising a compound of formula 1

| | Compound of formula 1 | vol.-% compound of formula 1 | Dopant | vol.-% Dopant | Thickness ETL/nm | EIL1 | Thickness EIL1/nm | EIL2 | Thickness EIL2 | Operating voltage at 10 mA/cm$^2$ (V) | cd/A efficiency at 10 mA/cm$^2$ (cd/A) |
|---|---|---|---|---|---|---|---|---|---|---|---|
| Example 13 | MX2 | 100 | — | 0 | 31 | — | 0 | — | 0 | 3.7 | 9.5 |
| Example 14 | MX2 | 70 | LI-1 | 30 | 31 | — | 0 | — | 0 | 4.05 | 7.3 |
| Example 15 | MX2 | 100 | — | 0 | 31 | Yb | 2 | — | 0 | 4 | 7.2 |
| Example 16 | MX2 | 70 | LI-1 | 30 | 31 | Yb | 2 | — | 0 | 3.6 | 9.1 |
| Example 17 | MX2 | 100 | — | 0 | 31 | Zn:Na (97.4:2.6 wt.- %) | 3 | Yb | 2 | 3.4 | 8.5 |
| Example 18 | MX2 | 70 | LI-1 | 30 | 31 | Zn:Na (97.4:2.6 wt.- %) | 3 | Yb | 2 | 3.4 | 8.9 |
| Example 19 | MX2 | 100 | — | 0 | 31 | Zn:Na (97.4:2.6 wt.- %) | 3 | — | 0 | 3.4 | 9.0 |
| Example 20 | MX2 | 70 | LI-1 | 30 | 31 | Zn:Na (97.4:2.6 wt.- %) | 3 | — | 0 | 3.4 | 8.7 |
| Example 21 | MX2 | 100 | — | 0 | 31 | Yb:KI (50:50 vol.- %) | 2 | — | 0 | 3.45 | 6.9 |

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. Organic electronic device comprising an organic semiconductor layer, wherein at least one organic semiconductor layer comprises a compound of formula 1:

$$L^1\text{-}Ar^1\text{-}[L^2]_n \quad (1),$$

wherein
$L^1$ has the formula 2:

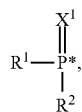

(2)

and
$L^2$ has the formula 3:

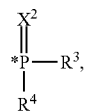

(3)

wherein
$L^1$ and $L^2$ are bonded at "*" via a single bond independently to the same or different arylene groups or heteroarylene groups of $Ar^1$; and wherein
$X^1$, $X^2$ are independently selected from O, S and Se;
$Ar^1$ is selected from substituted or unsubstituted $C_{20}$ to $C_{52}$ arylene or $C_{14}$ to $C_{64}$ heteroarylene, wherein the substituent of the substituted $C_{20}$ to $C_{52}$ arylene or $C_{14}$ to $C_{64}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl;
$R^1$, $R^2$ are independently selected from substituted or unsubstituted $C_1$ to $C_{16}$ alkyl, wherein the substituent of substituted $C_1$ to $C_{16}$ alkyl is selected from $C_6$ to $C_{18}$ arylene or $C_2$ to $C_{12}$ heteroarylene;
$R^3$, $R^4$ are independently selected from substituted or unsubstituted $C_1$ to $C_{16}$ alkyl, substituted or unsubstituted $C_6$ to $C_{18}$ arylene, $C_2$ to $C_{20}$ heteroarylene,
wherein the substituent of substituted $C_1$ to $C_{16}$ alkyl, the substituent of the substituted $C_6$ to $C_{18}$ arylene, $C_2$ to $C_{20}$ heteroarylene are independently selected from $C_6$ to $C_{18}$ arylene or $C_2$ to $C_{12}$ heteroarylene;
n is selected from 1 to 5, wherein n is an integer number.

2. The organic electronic device according to claim 1, wherein the compound of formula 1 is represented by formula 4:

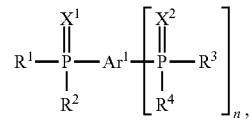

(4)

wherein
$X^1$, $X^2$ are independently selected from O, S and Se;
$Ar^1$ is selected from substituted or unsubstituted $C_{20}$ to $C_{52}$ arylene or $C_{14}$ to $C_{64}$ heteroarylene, wherein the substituent of the substituted $C_{20}$ to $C_{52}$ arylene or $C_{14}$ to $C_{64}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl;
$R^1$, $R^2$ are independently selected from substituted or unsubstituted $C_1$ to $C_{16}$ alkyl,
wherein the substituent of substituted $C_1$ to $C_{16}$ alkyl is selected from $C_6$ to $C_{18}$ arylene or $C_2$ to $C_{12}$ heteroarylene;
$R^3$, $R^4$ are independently selected from substituted or unsubstituted $C_6$ to $C_{18}$ arylene, $C_2$ to $C_{20}$ heteroarylene and $C_1$ to $C_{16}$ alkyl,
wherein the substituent of the substituted $C_6$ to $C_{18}$ arylene, $C_2$ to $C_{20}$ heteroarylene and $C_1$ to $C_{16}$ alkyl is selected from $C_6$ to $C_{18}$ arylene or $C_2$ to $C_{12}$ heteroarylene;
n is selected from 1 to 5, wherein n is an integer number;
wherein the compound of formula 4 comprises at least about 4 of $C_6$ arylene rings.

3. The organic electronic device according to claim 1, wherein the compound of formula 1 comprises about 4 of $C_6$ arylene groups to about 12 of $C_6$ arylene groups.

4. The organic electronic device according to claim 1, wherein the compound of formula 1 has a dipole moment of about ≥0 and about ≤3 Debye.

5. The organic electronic device according to claim 1, wherein $Ar^1$ has the formula 5:

(5)

wherein
$L^3$ and $L^4$ are bonded at "*" via a single bond to $L^1$ and $L^2$,
$Ar^2$ is selected from $C_{10}$ to $C_{42}$ arylene or $C_2$ to $C_{54}$ heteroarylene,
$L^3$, $L^4$ are independently selected from phenylene, biphenylene, fluoren-di-yl or a direct bond,
m is selected from 1 to 5, wherein m is an integer number.

6. The organic electronic device according to claim 1, wherein $Ar^1$ has the formula 6:

(6)

wherein
$Ar^3$ is bonded at "*" via a single bond to $L^1$ and $L^2$,
$Ar^3$ is selected from $C_6$ to $C_{25}$ arylene or 9-phenylcarbazol-di-yl, Ar⁴ is selected from substituted or unsubstituted $C_{10}$ to $C_{24}$ arylene or $C_2$ to $C_{28}$ heteroarylene, wherein the substituents on $C_{10}$ to $C_{24}$ arylene or $C_2$ to $C_{28}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl.

7. The organic electronic device according to claim 1, wherein
n is selected from about 1 to about 3, wherein n is an integer number.

8. The organic electronic device according to claim 1, wherein
$R^1$, $R^2$ are selected from $C_1$ to $C_{16}$ alkyl, and
$R^3$, $R^4$ are selected from $C_6$ to $C_{18}$ aryl.

9. The organic electronic device according to claim 1, wherein
$X^1$ and $X^2$ are selected the same, or $X^1$ and $X^2$ are O.

10. The organic electronic device according to claim 1, wherein
$R^1$, $R^2$, $R^3$ and $R^4$ are independently selected from $C_1$ to $C_{16}$ alkyl, or $R^1$, $R^2$, $R^3$ and $R^4$ are selected the same.

11. The organic electronic device according to claim 1, wherein
$X^1$, $X^2$ are O;
$Ar^1$ is selected from unsubstituted $C_{20}$ to $C_{52}$ arylene or unsubstituted $C_{14}$ to $C_{64}$ heteroarylene;
$R^1$, $R^2$, $R^3$, $R^4$ are independently selected from unsubstituted $C_1$ to $C_6$ alkyl;
n is selected from 1 to 3, wherein n is an integer number.

12. The organic electronic device according to claim 1, wherein the compound of formula 1 is free of heteroarylene groups or comprises at least about 1 to about 3 heteroarylene groups.

13. The organic electronic device according to claim 1, wherein $Ar^1$, $R^1$, $R^2$, $R^3$, $R^4$, or a combination thereof comprises at least one heteroarylene group selected from the group consisting of triazine, quinazoline, quinoline, benzimidazole, benzothiazole, benzo[4,5]thieno[3,2-d]pyrimidine, pyrimidine, and pyridine.

14. The organic electronic device according to claim 1, wherein $L^1$ and $L^2$ are bonded at "*" via a single bond to the same arylene group or different arylene groups of $Ar^1$.

15. The organic electronic device according to claim 1, wherein the compound of formula 1 is selected from the group of K1 to K42:

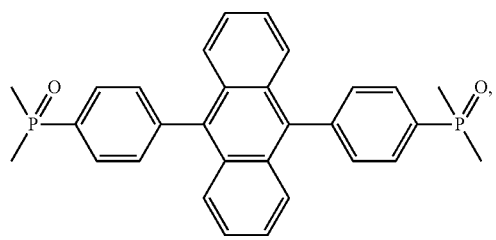
(K1)

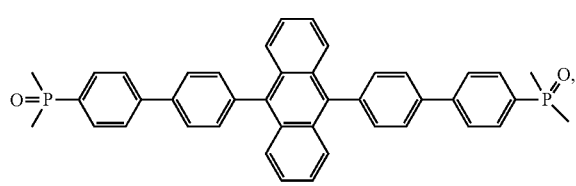
(K2)

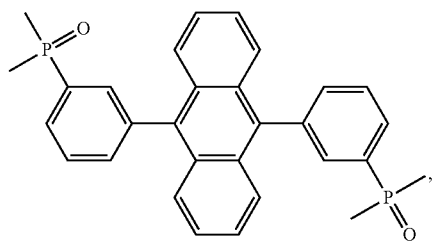
(K3)

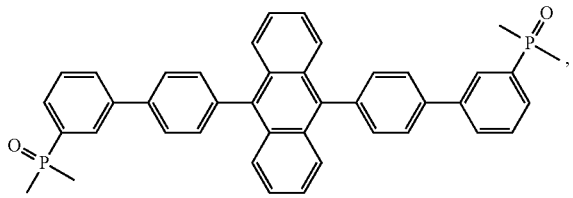
(K4)

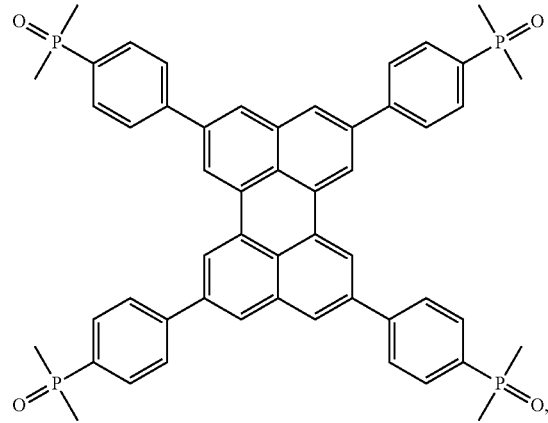
(K5)

(K6)

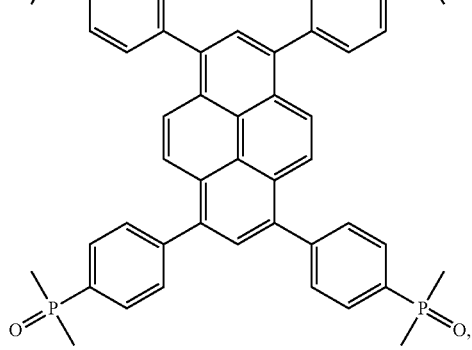

(K7)
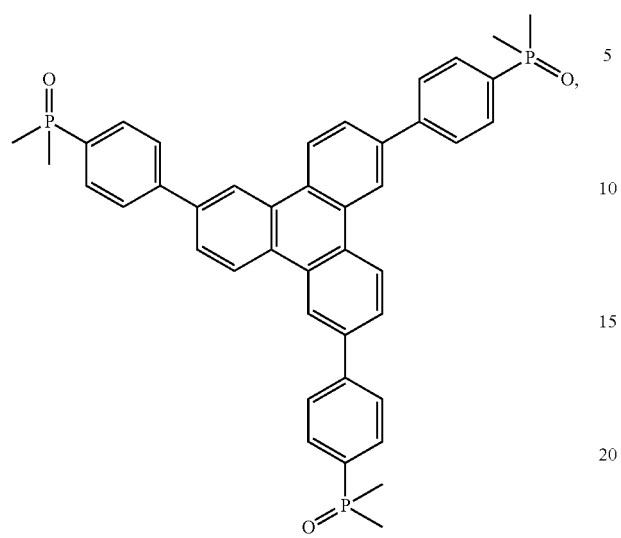
(K8)
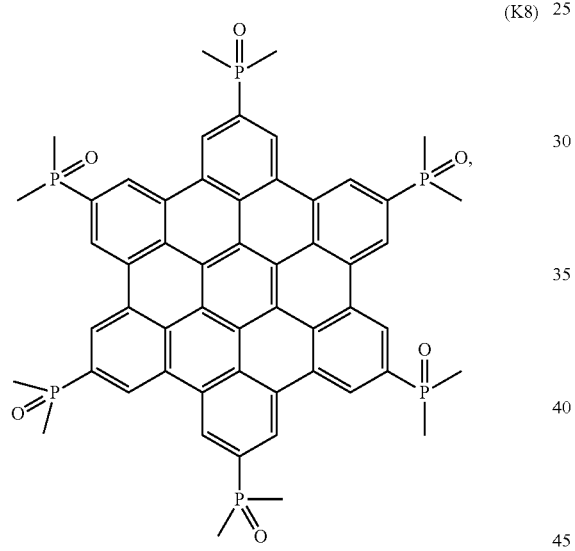
(K9)
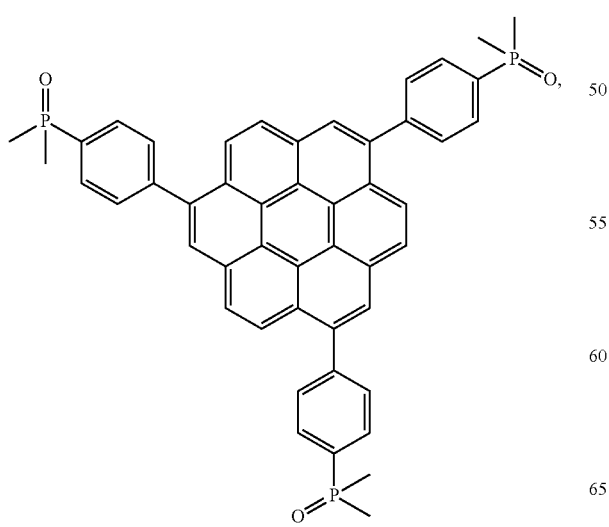
(K10)
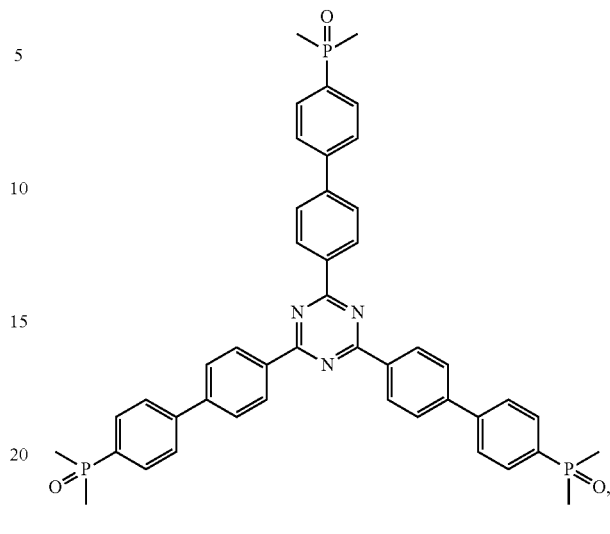
(K11)
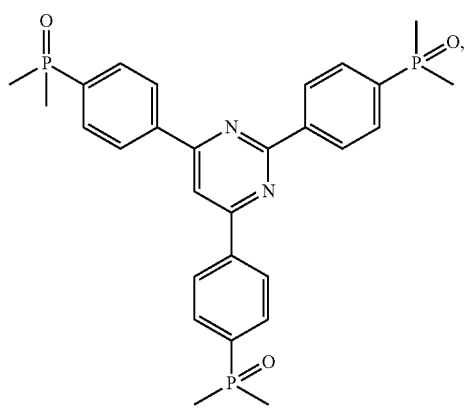
(K12)
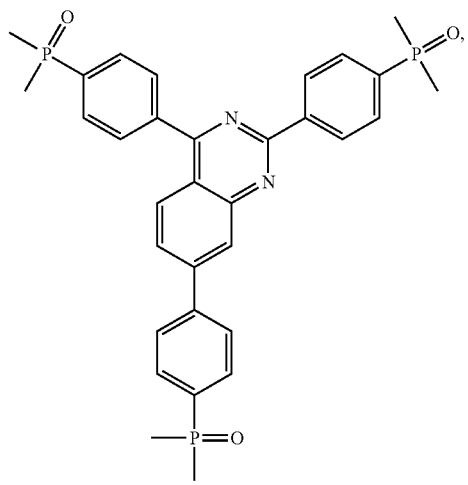

-continued
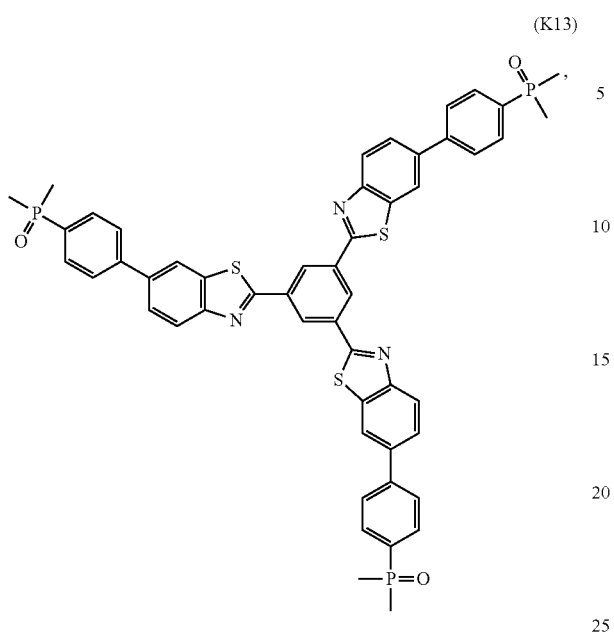
(K13)
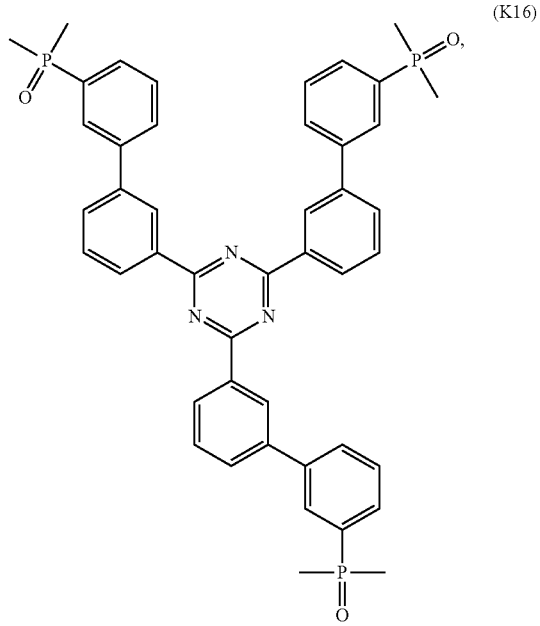
(K16)
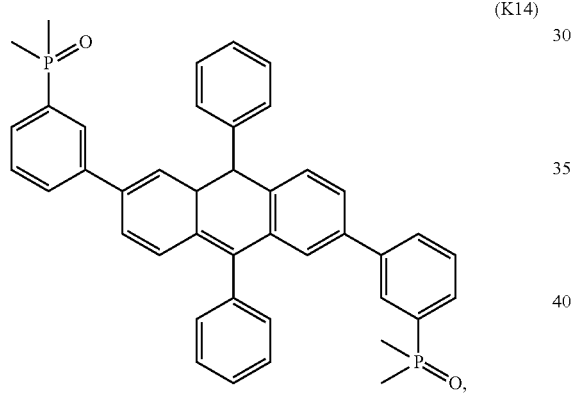
(K14)
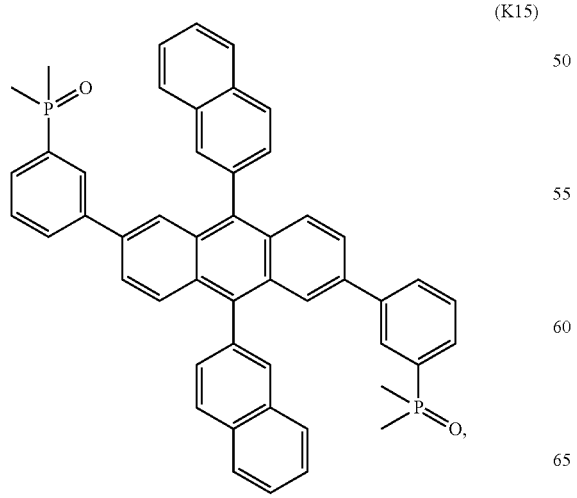
(K15)
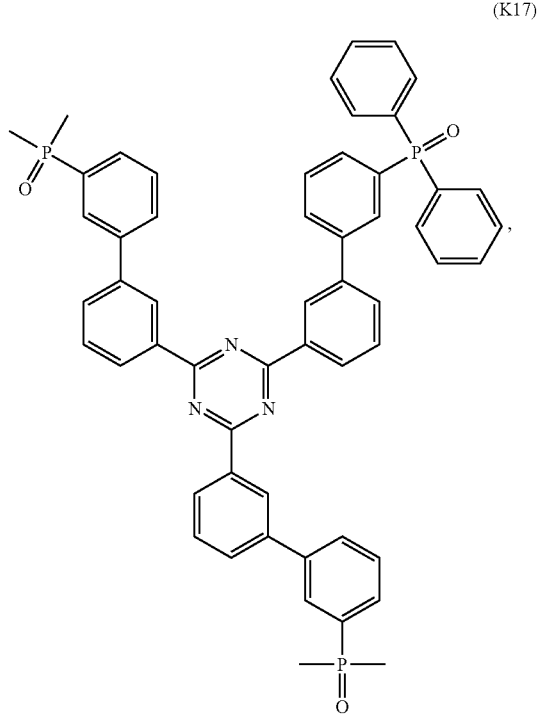
(K17)

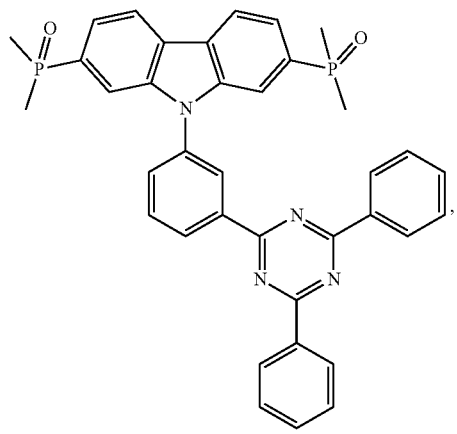
(K18)
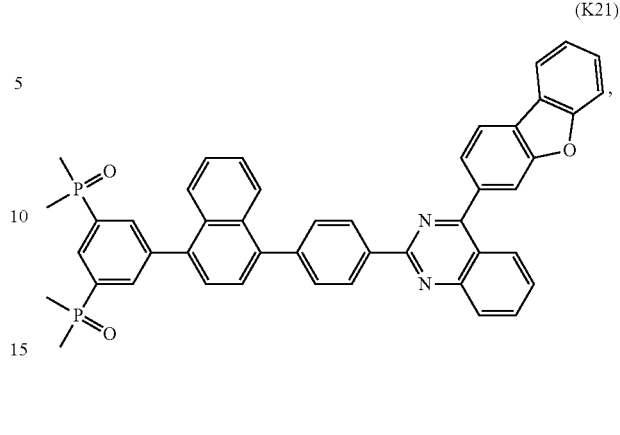
(K21)
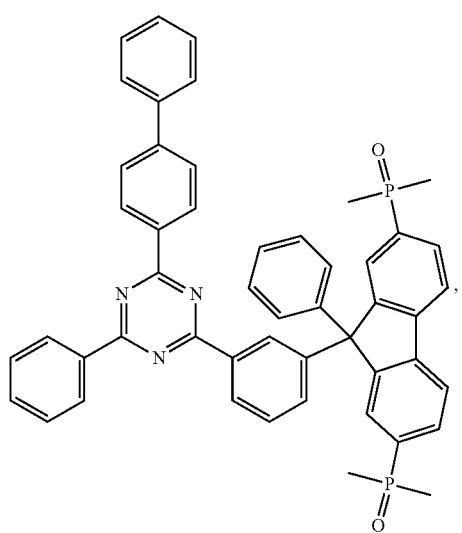
(K19)
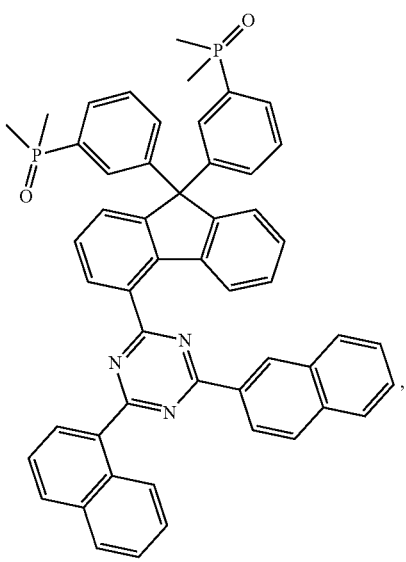
(K22)
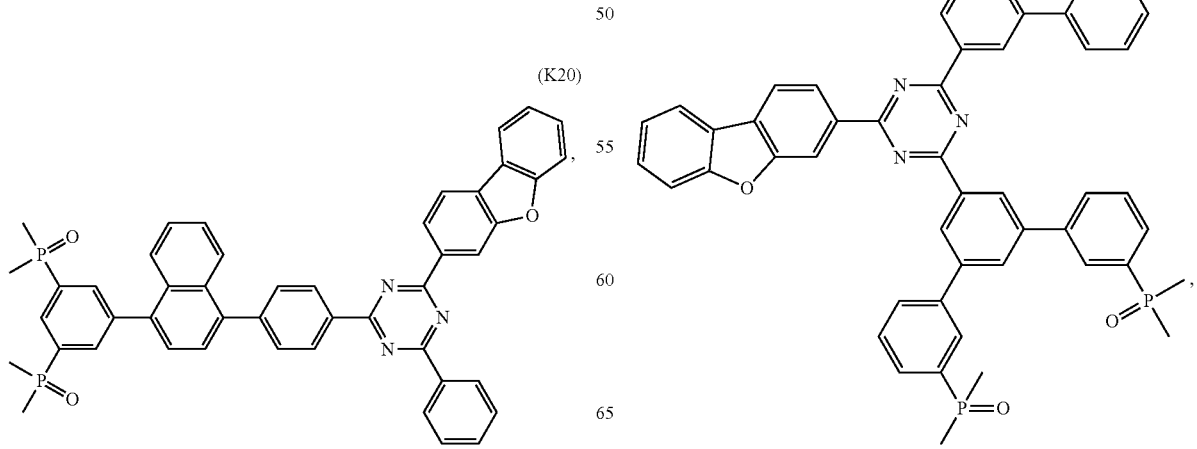
(K20), (K23)

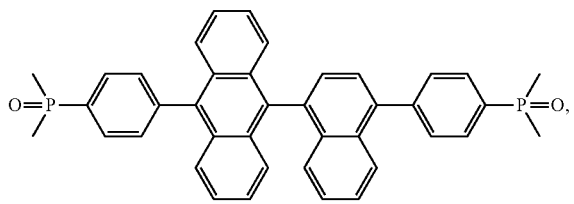
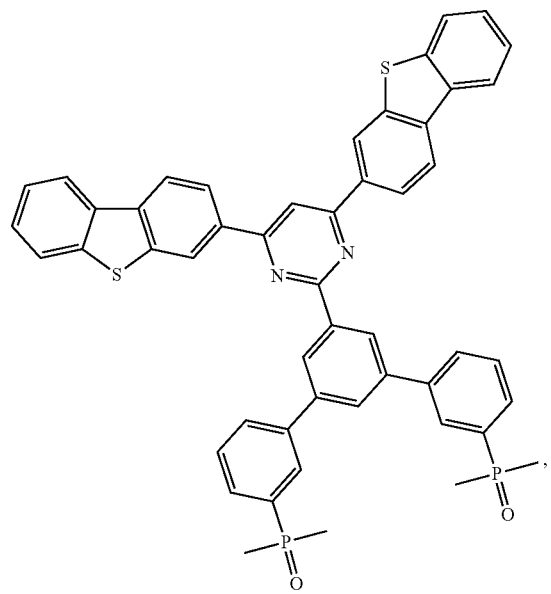

(K34)
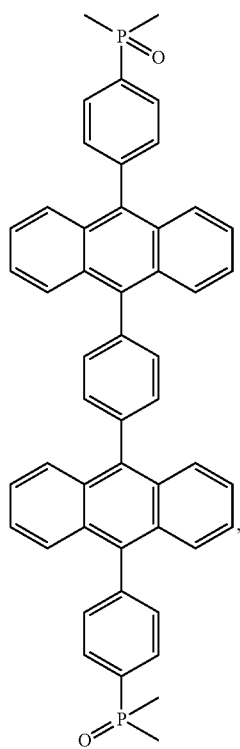
(K36)
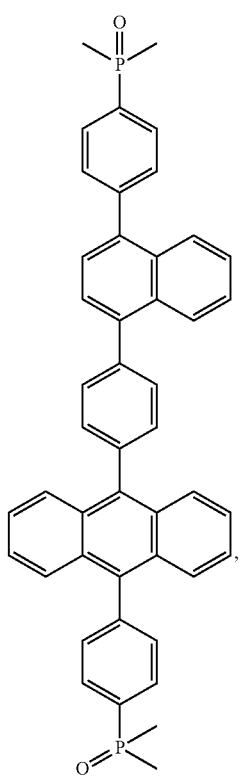
(K35)
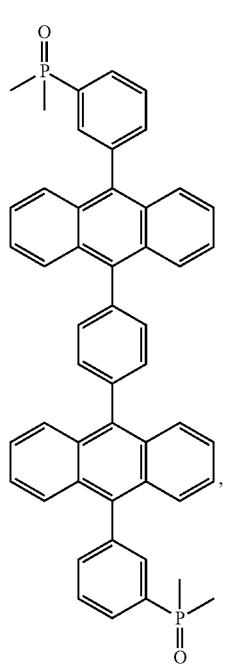
(K37)

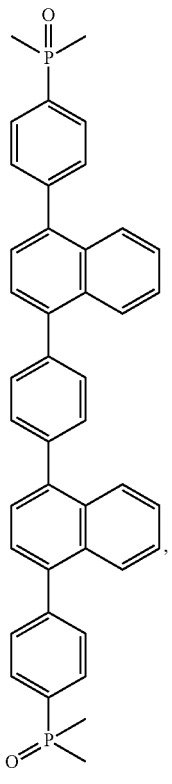

(K38)

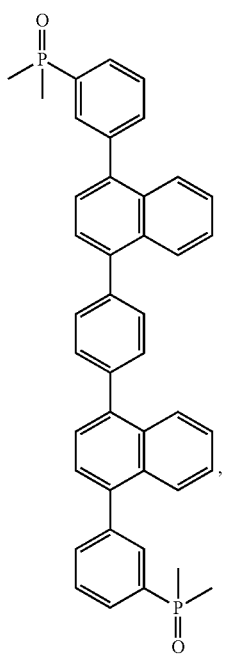

(K39)

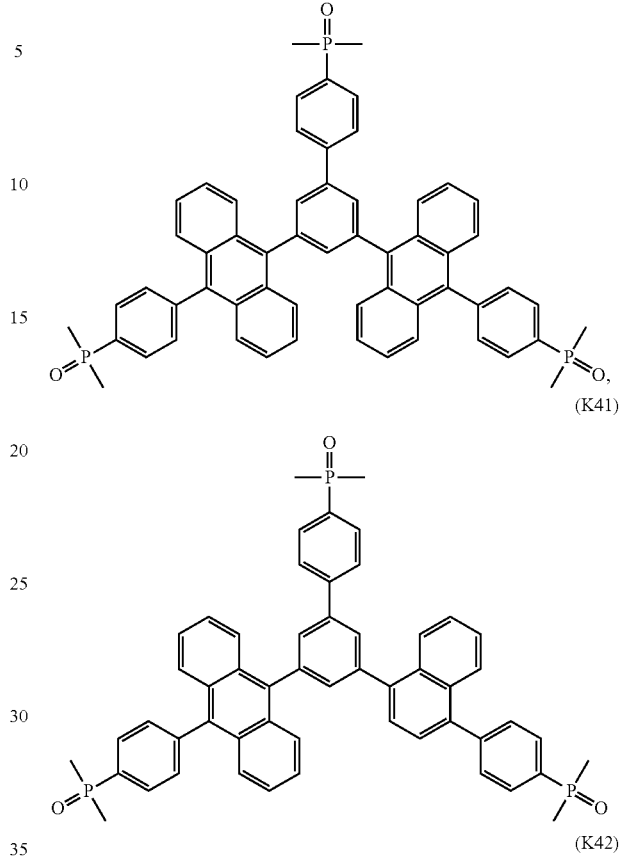

(K40)

(K41)

(K42)

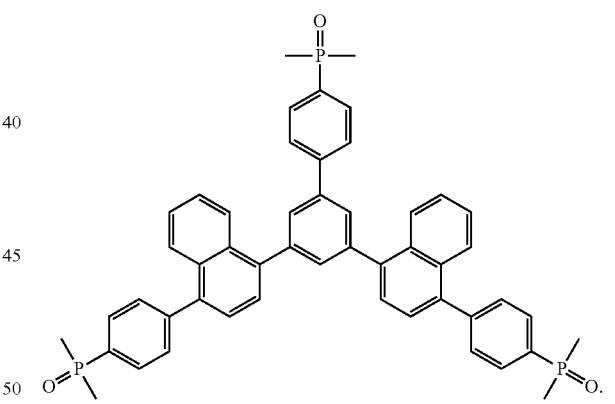

16. The organic electronic device according to claim 1, wherein the organic semiconductor layer is arranged between a photoactive layer and a cathode layer, or the organic semiconductor layer is an electron transport layer.

17. The organic electronic device according to claim 1, wherein the at least one organic semiconductor layer further comprises at least one alkali halide or alkali organic complex.

18. The organic electronic device according to claim 1, (i) wherein the organic electronic device further comprises at least one anode layer, at least one cathode layer and at least one emission layer, or (ii) wherein the organic electronic device further comprises at least one emission layer and at least one cathode layer, wherein the at least one organic semiconductor layer is arranged between the at least one emission layer and the at least one cathode layer.

19. The organic electronic device according to claim 1, further comprising an electron injection layer and a cathode layer, wherein the electron injection layer is arranged between the at least one organic semiconductor layer and the cathode layer, wherein the electron injection layer comprises at least one metal and/or a metal halide or metal organic complex.

20. A process of preparing an organic electronic device according to claim 1, wherein an electron injection layer is formed by
   (i) a step of transferring into the gas phase a metal composition comprising a first metal selected from an alkali metal and a second metal selected from Mg, Zn, Hg, Cd and Te and a step of depositing the alkali metal on the at least one organic semiconductor layer according; or
   (ii) a step of transferring into the gas phase a rare earth metal and an alkali metal halide and a step of depositing the rare earth metal and alkali halide on the at least one organic semiconductor layer.

21. The organic electronic device according to claim 1, wherein the organic electronic device is a thin film transistor, a battery, a display device, a photovoltaic cell, or a light emitting device.

22. A compound having the formula 1:

  (1), wherein
$L^1$ has the formula 2:

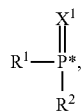  (2)

and
$L^2$ has the formula 3:

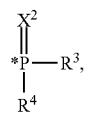  (3)

wherein
$L^1$ and $L^2$ are bonded at "*" via a single bond independently to the same or different arylene groups or heteroarylenes group of $Ar^1$; and
wherein
$X^1$, $X^2$ are independently selected from O, S and Se;
$Ar^1$ is selected from substituted or unsubstituted $C_{20}$ to $C_{52}$ arylene or $C_{14}$ to $C_{64}$ heteroarylene, wherein the substituent of the substituted $C_{20}$ to $C_{52}$ arylene or $C_{14}$ to $C_{64}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl;
$R_1$, $R^2$ are independently selected from substituted or unsubstituted $C_1$ to $C_{16}$ alkyl, wherein the substituent of substituted $C_1$ to $C_{16}$ alkyl is selected from $C_6$ to $C_{18}$ arylene or $C_2$ to $C_{12}$ heteroarylene;
$R^3$, $R^4$ are independently selected from substituted or unsubstituted $C_1$ to $C_{16}$ alkyl, substituted or unsubstituted $C_6$ to $C_{18}$ arylene, $C_2$ to $C_{20}$ heteroarylene, wherein the substituent of substituted $C_1$ to $C_{16}$ alkyl, the substituent of the substituted $C_6$ to $C_{18}$ arylene, $C_2$ to $C_{20}$ heteroarylene are independently selected from $C_6$ to $C_{18}$ arylene or $C_2$ to $C_{12}$ heteroarylene;
n is selected from 1 to 5, wherein n is an integer number;
wherein when $Ar^1$ is the substituted or unsubstituted $C_{14}$ to $C_{64}$ heteroarylene, (i) the substituted or unsubstituted $C_{14}$ to $C_{64}$ heteroarylene includes at least one heteroatom selected from the group consisting of N, O, B, Si, P, and Se, or (ii) n is selected from 2 to 5.

23. An organic semiconductor layer comprising a compound of formula 1:

  (1), wherein
$L^1$ has the formula 2:

  (2)

and
$L^2$ has the formula 3:

  (3)

wherein
$L^1$ and $L^2$ are bonded at "*" via a single bond independently to the same or different arylene groups or heteroarylene groups of $Ar^1$; and
wherein
$X^1$, $X^2$ are independently selected from O, S and Se;
$Ar^1$ is selected from substituted or unsubstituted $C_{20}$ to $C_{52}$ arylene or $C_{14}$ to $C_{64}$ heteroarylene, wherein the substituent of the substituted $C_{20}$ to $C_{52}$ arylene or $C_{14}$ to $C_{64}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl;
$R^1$, $R^2$ are independently selected from substituted or unsubstituted $C_1$ to $C_{16}$ alkyl, wherein the substituent of substituted $C_1$ to $C_{16}$ alkyl is selected from $C_6$ to $C_{18}$ arylene or $C_2$ to $C_{12}$ heteroarylene;
$R^3$, $R^4$ are independently selected from substituted or unsubstituted $C_1$ to $C_{16}$ alkyl, substituted or unsubstituted $C_6$ to $C_{18}$ arylene, $C_2$ to $C_{20}$ heteroarylene,
wherein the substituent of substituted $C_1$ to $C_{16}$ alkyl, the substituent of the substituted $C_6$ to $C_{18}$ arylene, $C_2$ to $C_{20}$ heteroarylene are independently selected from $C_6$ to $C_{18}$ arylene or $C_2$ to $C_{12}$ heteroarylene;
n is selected from 1 to 5, wherein n is an integer number.

24. An organic semiconductor layer comprising a compound of formula 4:

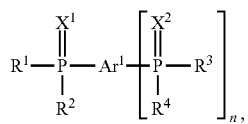

(4)

wherein $X^1$, $X^2$ are independently selected from O, S and Se;

$Ar^1$ is selected from substituted or unsubstituted $C_{20}$ to $C_{52}$ arylene or $C_{14}$ to $C_{64}$ heteroarylene, wherein the substituent of the substituted $C_{20}$ to $C_{52}$ arylene or $C_{14}$ to $C_{64}$ heteroarylene are independently selected from $C_1$ to $C_{12}$ alkyl, $C_1$ to $C_{12}$ alkoxy, CN, halogen, OH, $C_6$ to $C_{25}$ aryl and $C_2$ to $C_{21}$ heteroaryl;

$R^1$, $R^2$ are independently selected from substituted or unsubstituted $C_1$ to $C_{16}$ alkyl, wherein the substituent of substituted $C_1$ to $C_{16}$ alkyl is selected from $C_6$ to $C_{18}$ arylene or $C_2$ to $C_{12}$ heteroarylene;

$R^3$, $R^4$ are independently selected from substituted or unsubstituted $C_6$ to $C_{18}$ arylene, $C_2$ to $C_{20}$ heteroarylene and $C_1$ to $C_{16}$ alkyl, wherein the substituent of the substituted $C_6$ to $C_{18}$ arylene, $C_2$ to $C_{ao}$ heteroarylene and $C_1$ to $C_{16}$ alkyl is selected from $C_6$ to $C_{is}$ arylene or $C_2$ to $C_{12}$ heteroarylene;

n is selected from 1 to 5, wherein n is an integer number; wherein the compound of formula 4 comprises at least about 4 of $C_6$ arylene rings.

25. The organic electronic device according to claim 1, wherein $Ar^1$, $R^1$, $R^2$, $R^3$, $R^4$, or a combination thereof comprises at least one heteroarylene group selected from triazine or pyrimidine.

* * * * *